US012622823B2

(12) United States Patent
Bewick-Sonntag et al.

(10) Patent No.: US 12,622,823 B2
(45) Date of Patent: May 12, 2026

(54) ABSORBENT ARTICLE HAVING FLEX BOND CHANNEL REGIONS

(71) Applicant: The Procter & Gamble Company, Cincinnati, OH (US)

(72) Inventors: Christopher Philip Bewick-Sonntag, Cincinnati, OH (US); Rong Deng, Mason, OH (US); John David Norcom, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 492 days.

(21) Appl. No.: 18/198,308

(22) Filed: May 17, 2023

(65) Prior Publication Data

US 2023/0381035 A1 Nov. 30, 2023

Related U.S. Application Data

(60) Provisional application No. 63/480,335, filed on Jan. 18, 2023, provisional application No. 63/413,634, (Continued)

(51) Int. Cl.
*A61F 13/535* (2006.01)
*A61F 13/537* (2006.01)
*A61F 13/531* (2006.01)

(52) U.S. Cl.
CPC ...... *A61F 13/53752* (2013.01); *A61F 13/535* (2013.01); *A61F 2013/5315* (2013.01); *A61F 2013/53791* (2013.01)

(58) Field of Classification Search
CPC ............ A61F 13/535; A61F 2013/5315; A61F 13/53752; A61F 2013/53791; A61F 13/475; A61F 13/4756
See application file for complete search history.

(56) References Cited

U.S. PATENT DOCUMENTS

H163 H 11/1986 Spraker et al.
4,938,754 A 7/1990 Mesek
(Continued)

FOREIGN PATENT DOCUMENTS

CA 2182570 C 8/2000
CA 2239516 C 5/2002
(Continued)

OTHER PUBLICATIONS

PCT Search Report and Written Opinion for PCT/US2023/022455 dated Aug. 7, 2023, 11 pages.
(Continued)

*Primary Examiner* — Susan S Su
(74) *Attorney, Agent, or Firm* — Anna E. Haller; Amanda Herman Berghauer

(57) ABSTRACT

A disposable absorbent article having a front end region, a back end region, and a middle region disposed between the front and back end regions. The absorbent article includes a topsheet; a backsheet; an absorbent core structure disposed between the topsheet and backsheet; and a flex bond channel region formed in at least the middle region. The absorbent core structure includes an upper nonwoven layer having polymer fibers; a lower nonwoven layer having polymer fibers; and an inner core layer disposed between the upper and lower nonwoven layers. The flex bond channel region has a dry channel depth of at least 1.0 mm and a channel width of from about 1.0 mm to about 3.0 mm. The flex bond channel region has a CD Bending Resistance Index of from about 1.1 to about 3.0, and a Dry MD Bending Resistance of less than about 0.04 N/mm.

18 Claims, 15 Drawing Sheets

Related U.S. Application Data filed on Oct. 6, 2022, provisional application No. 63/413,638, filed on Oct. 6, 2022, provisional application No. 63/345,582, filed on May 25, 2022.

(56) References Cited

U.S. PATENT DOCUMENTS

| | | | |
|---|---|---|---|
| 5,275,591 | A | 1/1994 | Mavinkurve |
| 5,458,592 | A | 10/1995 | Abuto et al. |
| 5,567,260 | A | 10/1996 | Mcfall |
| 5,591,148 | A | 1/1997 | Mcfall et al. |
| 5,756,039 | A | 5/1998 | Mcfall |
| 5,810,800 | A | 9/1998 | Hunter et al. |
| 5,928,452 | A | 7/1999 | Mcfall et al. |
| D413,669 | S | 9/1999 | Mcfall et al. |
| 5,964,689 | A | 10/1999 | Mcfall et al. |
| 6,045,544 | A | 4/2000 | Hershberger et al. |
| 6,183,587 | B1 | 2/2001 | Mcfall et al. |
| 6,203,654 | B1 | 3/2001 | Mcfall et al. |
| 6,261,277 | B1 | 7/2001 | Osborn, III et al. |
| 6,316,688 | B1 | 11/2001 | Hammons |
| 6,425,890 | B1 | 7/2002 | Samuelsson et al. |
| 6,432,096 | B1 | 8/2002 | Mcfall et al. |
| 6,437,214 | B1 | 8/2002 | Everett et al. |
| 6,447,496 | B1 | 9/2002 | Mizutani |
| 6,475,199 | B1 | 11/2002 | Gann et al. |
| 6,482,193 | B1 | 11/2002 | Samuelsson |
| 6,570,058 | B1 | 5/2003 | Fuchs et al. |
| 6,575,952 | B2 | 6/2003 | Kirk |
| 6,582,411 | B1 | 6/2003 | Carstens et al. |
| 6,692,603 | B1 | 2/2004 | Lindsay |
| 6,702,796 | B2 | 3/2004 | Mcfall et al. |
| 6,899,701 | B2 | 5/2005 | Carstens et al. |
| 7,056,404 | B2 | 6/2006 | Mcfall et al. |
| 7,696,402 | B2 | 4/2010 | Nishikawa |
| 7,704,241 | B2 | 4/2010 | Rosenfeld et al. |
| 7,969,402 | B2 | 6/2011 | Lee |
| 8,398,915 | B2 | 3/2013 | Alkmin |
| 8,480,387 | B2 | 7/2013 | Alkmin |
| 8,512,305 | B2 | 8/2013 | Dziezok et al. |
| 8,715,258 | B2 | 5/2014 | Munakata |
| 8,911,418 | B2 | 12/2014 | Van Den Bogart |
| 8,979,815 | B2 | 3/2015 | Roe et al. |
| 9,060,904 | B2 | 6/2015 | Hundorf et al. |
| 9,259,363 | B2 | 2/2016 | Dziezok et al. |
| 9,406,478 | B2 | 8/2016 | Birnbach et al. |
| 9,492,333 | B2 | 11/2016 | Uda et al. |
| 9,889,049 | B2 | 2/2018 | Hörle |
| 10,772,772 | B2 | 9/2020 | Michiels et al. |
| 10,786,403 | B2 | 9/2020 | Bianchi |
| 10,940,053 | B2 | 3/2021 | Hood |
| 11,464,385 | B2 | 10/2022 | Davis et al. |
| 2001/0029359 | A1 | 10/2001 | Carlucci |
| 2003/0200991 | A1 | 10/2003 | Keck |
| 2004/0147895 | A1 | 7/2004 | Mizutani |
| 2006/0229579 | A1* | 10/2006 | Wahlstrom ........ A61F 13/53747 604/366 |
| 2007/0044903 | A1 | 3/2007 | Wisneski et al. |
| 2007/0087169 | A1 | 4/2007 | Mcfall |
| 2008/0167634 | A1 | 7/2008 | Kouta et al. |
| 2009/0004435 | A1* | 1/2009 | Hanao .................... A61F 13/53 428/156 |
| 2010/0280479 | A1 | 11/2010 | Lindqvist et al. |
| 2010/0312206 | A1 | 12/2010 | Fujioka |
| 2011/0137276 | A1 | 6/2011 | Yoshikawa |
| 2011/0251575 | A1* | 10/2011 | Kuroda ............... A61F 13/4756 604/380 |
| 2013/0066290 | A1 | 3/2013 | Kawakami et al. |
| 2013/0231622 | A1 | 9/2013 | Dieringer |
| 2016/0120711 | A1 | 5/2016 | Zamudio Ahumada |
| 2016/0310330 | A1 | 10/2016 | Knos et al. |
| 2019/0374396 | A1 | 12/2019 | Hood |
| 2020/0315859 | A1 | 10/2020 | Denti et al. |
| 2020/0315871 | A1 | 10/2020 | Viens et al. |
| 2020/0315873 | A1 | 10/2020 | Viens et al. |
| 2021/0292973 | A1 | 9/2021 | Rouse et al. |
| 2021/0401631 | A1 | 12/2021 | Kalentun |
| 2021/0401632 | A1 | 12/2021 | Kalentun |
| 2022/0104973 | A1 | 4/2022 | Viens et al. |
| 2022/0168158 | A1 | 6/2022 | Miller et al. |
| 2022/0387227 | A1 | 12/2022 | Kreisel et al. |
| 2023/0149224 | A1* | 5/2023 | Van Sande .......... A61F 13/4756 604/378 |
| 2023/0277392 | A1 | 9/2023 | Aviles et al. |

FOREIGN PATENT DOCUMENTS

| | | | |
|---|---|---|---|
| DE | 202017006014 | U1 | 1/2018 |
| EP | 0834297 | A1 | 4/1998 |
| EP | 0812171 | B1 | 5/2000 |
| EP | 1075244 | B1 | 6/2003 |
| EP | 1504741 | A1 | 2/2005 |
| EP | 1688111 | A1 | 8/2006 |
| EP | 2133052 | A1 | 12/2009 |
| EP | 2371333 | A1 | 10/2011 |
| EP | 2740450 | A1 | 6/2014 |
| EP | 2572687 | B1 | 4/2016 |
| EP | 2630939 | B1 | 5/2020 |
| EP | 3799848 | A1 | 4/2021 |
| JP | 2003265519 | A | 9/2003 |
| JP | 2008161564 | A | 7/2008 |
| JP | 2008229032 | A | 10/2008 |
| JP | 2009112864 | A | 5/2009 |
| JP | 2009207598 | A | 9/2009 |
| JP | 5099769 | B2 | 10/2012 |
| JP | 2020171688 | A | 10/2020 |
| JP | 2021083542 | A | 6/2021 |
| WO | 9625903 | A1 | 8/1996 |
| WO | 9955272 | A1 | 11/1999 |
| WO | 2001097736 | A1 | 12/2001 |
| WO | 0236059 | A1 | 5/2002 |
| WO | 2012118235 | A1 | 9/2012 |
| WO | 200641507 | A1 | 7/2017 |
| WO | 2017115541 | A1 | 7/2017 |
| WO | 2017207135 | A1 | 12/2017 |
| WO | 2018139962 | A1 | 8/2018 |
| WO | 2020137428 | A1 | 7/2020 |
| WO | 2020205946 | A1 | 10/2020 |

OTHER PUBLICATIONS

All Office Actions; U.S. Appl. No. 18/804,459, filed on Aug. 14, 2024.

U.S. Appl. No. 18/804,459, filed on Aug. 14, 2024, to Christopher Philip Bewick-Sonntag et al.

* cited by examiner

ABSORBENT ARTICLE HAVING FLEX BOND CHANNEL REGIONS

CROSS REFERENCE TO RELATED APPLICATIONS

This application claims the benefit of U.S. Provisional Application No. 63/413,638, filed Oct. 6, 2022, and U.S. Provisional Application No. 63/345,582, filed May 25, 2022, U.S. Provisional Application No. 63/413,634, filed Oct. 6, 2022, and U.S. Provisional Application No. 63/480,335, filed Jan. 18, 2023, the entire disclosures of which are fully incorporated by reference herein.

FIELD OF THE INVENTION

The present disclosure relates to an absorbent article having flex bond channel regions. More particularly, to an absorbent article having flex bond channel regions yet is still flexible and conforms closely to the body.

BACKGROUND OF THE INVENTION

Absorbent articles are widely used among consumers, e.g., diapers, training pants, feminine pads, adult inconti-nence pads, etc. Generally, absorbent articles such as these comprise a topsheet and a backsheet, with an absorbent core structure disposed therebetween. These absorbent articles are designed to absorb and retain liquids and other dis-charges from the human body to prevent body and garment soiling.

To absorb body fluid effectively without leakage, the absorbent article should conform closely to the wearer's body such that the absorbent article can catch body fluid in an intended place of the absorbent article (e.g., the center of the absorbent core structure). Historically, for menstrual applications, channels created by embossing have been leveraged to create bending lines in thicker and/or stiffer products to provide specific in-use pad shapes and to help improve the fit to the body. In traditional cellulose based absorbent core structures, channels are formed by applying a high compressive force in order to densify the cellulose to a point where the cellulose is irreversibly compressed. While such channels may provide a preferential bending location within the absorbent article, the high compression force (i.e., densification) needed to create the channel (and keep the channel in place) creates stiffness that can hinder the ability of the absorbent article to conform to the wearer's body in both the longitudinal and lateral directions. As such, these products are not believed to conform or fit to the body of the wearer as closely as possible, particularly at the portions that are adjacent to the discharge portion of body fluids in use, and thus, leakage is possible. To effectively conform to the body, it is desired that an absorbent article can bend at preferential locations in both a longitudinal and lateral direction.

There is a need for an absorbent article that comprises channels yet can still be conformable to the body and flexible in both the longitudinal and lateral direction.

SUMMARY OF THE INVENTION

The present disclosure solves the problem of absorbent articles having channels that are stiff and nonconformable by providing an absorbent core structure that can sandwich a liquid-absorbent material between two nonwoven layers that can plastically deform to form a flex bond channel region without high densification of the absorbent core structure and/or inner core layer. As described herein, the flex bond channel region may be flexible in both the longitudinal and lateral directions, thus allowing the absorbent article to conform closely to the body.

An absorbent article comprises a front end region, a back end region, and a middle region disposed between the front end and back end regions; a topsheet; a backsheet; an absorbent core structure disposed between the topsheet and the backsheet, wherein the absorbent core structure com-prises: (a) an upper nonwoven layer comprising polymer fibers; (b) a lower nonwoven layer comprising polymer fibers; and (c) an inner core layer disposed between the upper nonwoven layer and the lower nonwoven layer, wherein the inner core layer comprises cellulosic fibers and superabsorbent particles; and a flex bond channel region formed in at least the middle region, wherein the flex bond channel region has a dry channel depth of at least 1.0 mm and a width of from about 1.0 mm to about 3.0 mm; and wherein the flex bond channel region has a CD Bending Resistance Index of from about 1.1 to about 3.0, and a Dry MD Bending Resistance of less than about 0.04 N/mm as measured according to Flex Bond Channel MD Bending Resistance Method.

A disposable absorbent article comprises a topsheet; a backsheet; an absorbent core structure disposed between the topsheet and the backsheet; wherein the topsheet forms a wearer facing surface of the absorbent article and the back-sheet forms an outward facing surface of the absorbent article; wherein the absorbent core structure comprises: (a) an upper nonwoven layer comprising polymer fibers; (b) a lower nonwoven layer comprising polymer fibers; and (c) an inner core layer disposed between the upper nonwoven layer and the lower nonwoven layer; wherein the inner core layer comprises cellulosic fibers and superabsorbent particles; wherein the inner core layer comprises from about 125 to about 400 gsm cellulosic fibers; wherein the wearer facing surface of the absorbent article comprises a flex bond channel region having a Dry MD Bending Resistance of less than about 0.04 N/mm as measured according to Flex Bond Channel MD Bending Resistance Method and a density of from about 0.05 g/cm3 to about 0.3 g/cm3.

A disposable absorbent article comprises a topsheet; a backsheet; an absorbent core structure disposed between the topsheet and the backsheet, wherein the absorbent core structure comprises an upper nonwoven layer comprising polymer fibers and an inner core layer comprising from about 125 gsm to about 400 gsm cellulosic fibers; wherein the inner core layer has a wearer facing surface and an outward facing surface and the upper nonwoven layer is in direct contact with the wearer facing surface of the inner core layer; and a flex bond channel region comprising one or more flex bond embossments having an embossment length of from about 1.0 mm to about 4.0 mm; wherein the flex bond channel region has a channel depth of at least 1.0 mm and a width of from about 1.0 mm to about 3.0 mm; wherein the flex bond channel region has a Dry MD Bending Resistance of less than about 0.04 N/mm as measured according to Flex Bond Channel MD Bending Resistance Method.

DETAILED DESCRIPTION OF THE INVENTION

Figure 1:
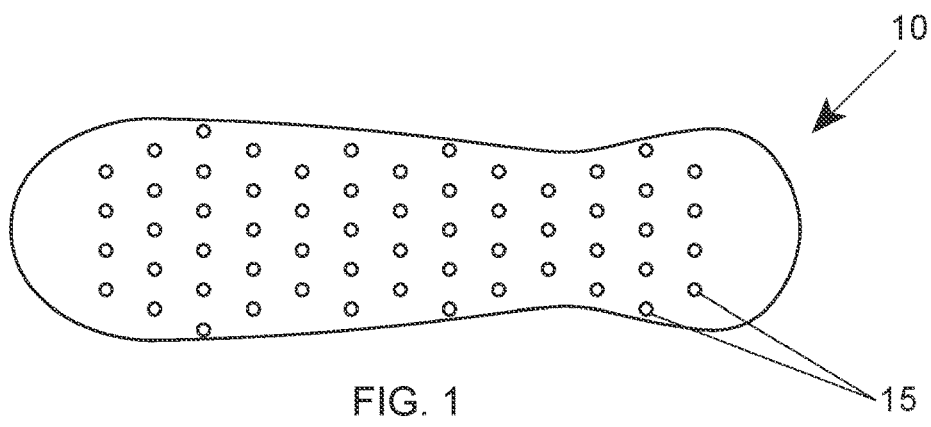
FIG. 1 is a representation of an absorbent core structure in accordance with the present disclosure.

As used herein "disposable absorbent article" or "absorbent article" shall be used in reference to articles such as diapers, training pants, diaper pants, refastenable pants, adult incontinence pads, adult incontinence pants, feminine hygiene pads, cleaning pads, and the like, each of which are intended to be discarded after use.

As used herein "absorbent core structure" shall be used in reference to the upper nonwoven layer, the lower nonwoven layer, and the inner core layer disposed between the upper nonwoven layer and the lower nonwoven layer.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein, "machine direction" refers to the direction in which a web flows through an absorbent article converting process. For the sake of brevity, may be referred to as "MD".

As used herein, "cross machine direction" refers to the direction which is perpendicular to the MD. For the sake of brevity, may be referred to as "CD".

As used herein, "resilient" refers to a material that tends to retain its shape both in the dry and wet states and when subjected to a compression force tends to recover its original, pre-compression shape when such force is removed. In some aspects, the upper and/or lower nonwoven layers described herein may be resilient.

As used herein, "wearer-facing" (sometimes referred to herein as body-facing) and "outward-facing" (sometimes referred to herein as garment-facing) refer respectively to the relative location of an element or a surface of an element or group of elements. "Wearer-facing" implies the element or surface is nearer to the wearer during wear than some other element or surface. "Outward-facing" implies the element or surface is more remote from the wearer during wear than some other element or surface (i.e., element or surface is proximate to the wearer's garments that may be worn over the absorbent article).

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The disposable absorbent articles described herein may comprise a topsheet, a backsheet, and an absorbent core structure disposed therebetween. The absorbent core structure may comprise an upper nonwoven layer and lower nonwoven layer, with an inner core layer disposed between the upper nonwoven layer and lower nonwoven layer. The inner core layer may be contained within the nonwoven layers by substantially sealing at least a left side region and a right side region of the upper and lower nonwoven layers at a perimeter seal. In some configurations, the upper and lower nonwoven layers may be joined at a perimeter seal which extends around the entire perimeter of the inner core layer. The absorbent article may further comprise one or more flex bond channel regions comprising closely spaced flex bond embossments.

As used herein, "flex bond channel region" refers to a generally elongated depression formed in at least a portion of an absorbent article, partially or entirely extending through the z-direction thickness of the absorbent article. Flex bond channel regions can reduce the thickness of the absorbent article in the z-direction and can act as preferential bending lines in the absorbent article, allowing the article to bend in particular directions so as to fit more closely to the wearer's body. Flex bond channel regions may also act as fluid wicking or fluid transport barriers that can reduce the potential for fluid to migrate to the absorbent article perimeter and cause a leak.

In some aspects, the disposable absorbent article may comprise the following structure (from a wearer-facing surface to an outward-facing surface): a topsheet, an upper nonwoven layer, an inner core layer, a lower nonwoven layer, and a backsheet. In some aspects, the topsheet may be in direct contact with the upper nonwoven layer, the upper nonwoven layer may be in direct contact with the inner core layer, and/or the inner core layer may be in direct contact with the lower nonwoven layer. By "direct contact", it is meant that there is no further intermediate component layer between the respective layer in direct contact thereto. It is however not excluded that an adhesive material may be disposed between at least a portion of the layers described above.

Figure 3:
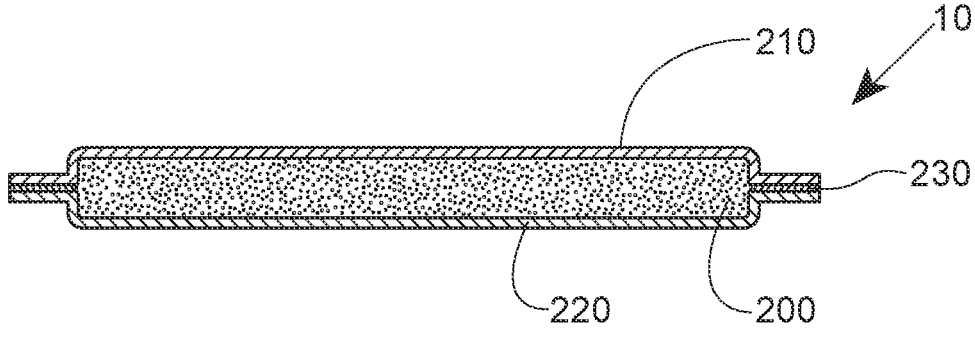
FIG. 3 is a cross section of the absorbent core structure.

Referring to FIGS. 1 and 3, an absorbent core structure 10 may comprise an upper nonwoven layer 210 and a lower nonwoven layer 220 (also referred to herein collectively as upper and lower nonwoven layers or upper and lower nonwovens) and an inner core layer 200 disposed between the upper nonwoven layer 210 and the lower nonwoven layer 220. The absorbent core structure may comprise inner core layer 200 comprising a liquid absorbent material. Without being limited by theory, it is believed that the absorbent core structure may recover its shape dry or wet across a range of bodily movements and compressions. The liquid absorbent material may comprise a matrix comprising cellulosic fibers and superabsorbent particles, sometimes referred to herein as "fluff/AGM". The upper and lower nonwoven layers 210, 220 may be joined together at a perimeter seal 230 with glue or other conventional bonding methods including, but not limited to, ultrasonic bonding, fusion bonding, crimping, and combinations thereof.

The upper and lower nonwoven layers 210, 220 may extend outwardly from an inner core layer perimeter and may be joined together to form the perimeter seal 230. In some configurations, the entire inner core layer 200 may be located inboard of the perimeter seal 230. The perimeter seal 230 may help to seal the absorbent material of the inner core layer 200 inside the upper and lower nonwoven layers 210, 220. In some configurations, the perimeter seal 230 may extend around the entire inner core layer perimeter 200a. In some configurations, the perimeter seal 230 may extend partially around the inner core layer perimeter.

In some configurations, the upper and lower nonwoven layers 210, 220 may be discrete materials that can be cut to approximately the size and shape of the inner core layer 200 so as to fit between the topsheet and backsheet but may not extend substantially into either the front end or the back end region of the absorbent article. In some configurations, the upper and/or lower nonwoven layers 210, 220 may extend from the front end region of the absorbent article to the back end region of the absorbent article.

The flexibility and/or resiliency of the absorbent core structure results in an absorbent article that comfortably conforms to the wearer's anatomical geometry while efficiently managing the fluid as it exits the body. This can, unexpectedly, be achieved without typical densification stiffening (for wet integrity) by leveraging resilient upper and lower nonwoven layers composed of resilient polymers located above and below the loosely packed fluff/AGM matrix of the inner core layer. This absorbent core structure is able to carry the structural load and recover shape without physically being stiff or losing the desired structural properties when the absorbent core structure becomes wet.

It is believed that wet integrity/shape stability in a cellulose rich absorbent core structure without substantial densification and stiffening results when select resilient upper and lower nonwovens 210, 220 are positioned above and below the fluff/AGM matrix of the inner core layer and specially joined to and around the fluff/AGM matrix. The upper and lower nonwovens require sufficient recovery force to carry the fluff/AGM matrix back to the original state or a stable fiber orientation state following compression. Wrapping or encapsulating a cellulose rich fluff core with a simple cellulose tissue or less resilient nonwoven material may not exhibit sufficient recovery energy to recover shape in-use and particularly when wetted. Structural, wet resilient nonwovens detailed herein may exhibit recovery energies following compression that are sufficient to recover the cellulose rich fiber matrix and are chosen to deliver high compression recovery, with relatively low stiffness, in both dry and wet states.

It was further found that an absorbent article comprising flex bond channel regions could be created while maintaining flexibility of the absorbent article in both the lateral and longitudinal direction, allowing the absorbent article to better conform to the body. Without being limited by theory, it is believed that the upper nonwoven can plastically deform and maintain the channel structure without the need to permanently compress (densify) the fluff/AGM of the inner core layer.

Suitable upper nonwoven layers may have a basis weight of from about 30 gsm to about 85 gsm, or from about 35 gsm to about 70 gsm, or from about 40 to about 60 gsm. The upper nonwoven layer may have a Tensile Stiffness of from about 0.3 N/mm to about 1.6 N/mm. The upper nonwoven layer may have a Strain to Break of greater than about 10%, or from about 10% to about 50%, or from about 20% to about 40%. The upper nonwoven layer may have a Permanent Strain of about 0.005 to about 0.013 mm/mm, or from 0.005 to about 0.0090 mm/mm.

Suitable lower nonwoven layers may have a basis weight of from about 10 to about 40 gsm, or from about 15 to about 20 gsm. The lower nonwoven layer may have a Tensile Stiffness of from about 0.2 N/mm to about 1.6 N/mm. The lower nonwoven layer may have a Strain to Break of greater than about 10%, or from about 10% to about 50%, or from about 20% to about 40%. The lower nonwoven layer may have a Permanent Strain of about 0.005 to about 0.013 mm/mm.

The upper and lower nonwoven layers may comprise polymer fibers. Suitable upper and lower nonwoven fibers may be selected from PET (polyethylene terephthalate), PP (polypropylene), a BiCo (Bicomponent fiber) selected from PE/PP (PE sheath and PP core) and/or PE/PET (PE sheath PET core), PLA (polylactic acid), and combinations thereof.

Suitable upper nonwoven layers may comprise from about 60 to about 100%, or from about 70% to about 100% synthetic fibers, and from about 0 to about 40%, or from about 0 to about 30% regenerated cellulosic fibers, such as rayon and/or viscose.

The upper nonwoven layer may comprise fibers having a staple length of greater than about 10 mm, or greater than about 25 mm, or from about 10 mm to about 100 mm, or from about 20 mm to about 75 mm, or from about 25 mm to about 50 mm. The upper nonwoven layer may comprise fibers having a fiber diameter of from about 1.3 DTex to about 10 DTex, or from about 1.3 DTex to about 6.0 DTex, or from about 2.0 DTex to about 5.0 DTex. In some configurations, the upper nonwoven layer may comprise fibers, wherein the fibers are a blend of staple fibers having a fiber diameter of from about 2.0 DTex to about 10 DTex.

The lower nonwoven layer may comprise fibers having a length of greater than about 10 mm, or greater than about 25 mm, or from about 10 mm to about 100 mm, or from about 20 mm to about 75 mm, or from about 25 mm to about 50 mm. In some configurations, the lower nonwoven layer may comprise continuous fibers. The lower nonwoven layer may comprise fibers having a fiber diameter of from about 1.3 DTex to about 5.0 DTex, or from about 1.3 DTex to about 3.3 DTex, alternatively from about 1.3 DTex to about 2.2 DTex, or from about 2.0 DTex to about 10 DTex. In some configurations, the lower nonwoven layer may comprise fibers, wherein the fibers are a blend of fibers having a fiber diameter of from about 0.1 DTex to about 6.0 DTex.

In some configurations, suitable fiber combinations may include upper nonwoven polymer fibers having a diameter of from about 2.0 DTex to about 10 DTex and lower nonwoven polymer fibers having a diameter of from about 1.7 DTex to about 5 DTex. In some configurations, suitable fiber combinations may include upper nonwoven polymer fibers having a diameter of from about 1.3 DTex to about 2.2 DTex and lower nonwoven polymer fibers having a diameter of from about 1.7 DTex to about 5 DTex.

Nonwoven layers comprising polymer fibers are able to hold their shape and resist plasticizing when wet and are attached to the fluff/AGM matrix through the application of a core construction adhesive that is applied either directly to the fluff/AGM matrix or the resilient nonwoven via a conventional spray coating application chosen to achieve a bond but not disrupt the flow of fluid to the fluff/AGM matrix. Additionally, the upper and lower nonwoven layers may have at least a partial perimeter seal to better connect the upper and lower nonwoven layers with the inner core layer contained within the upper and lower nonwoven layer. This perimeter seal is typically containing at least a middle region of the absorbent article in the area located between the wearer's inner thighs. The presence of the perimeter seal, external to the fluff/AGM matrix, where the upper and lower nonwoven layers are bonded by conventional means (e.g., adhesives, polymer welding, and/or strong physical entanglement) helps to ensure the upper and lower nonwovens maintain their structural function during physical deformations without separating, helping to limit any potential integrity and bunching issues. Creating a perimeter seal that substantially contains the inner core layer may allow for any excess material to be removed to enable an absorbent core structure to be shaped to conform to inner thigh geometry.

Suitable upper and lower nonwoven layer materials may bend and recover their original shape following the bending force Flimsy or highly flexible materials readily bend at low peak force (load) and with low bending energy. Unsuitable materials, while readily bending, do not have sufficient recovery energy and so retain a deformed, bent state because of insufficient recovery energy. Suitable materials have sufficient energy to recover their initial pre-bent state. The materials with sufficient bending recovery energy may be considered resilient upper and lower nonwoven layers.

As noted above, the upper and lower nonwovens may include polymer fibers. Polymer fibers may be included to help provide structural integrity to the upper and lower nonwovens. The polymer fibers may help increase structural integrity of the upper and lower nonwovens in both a machine direction (MD) and in a cross-machine direction (CD), which may facilitate web manipulation during processing of the upper and lower nonwovens for incorporation into a pad.

Polymer fibers of any suitable composition may be selected. Some examples of suitable polymer fibers may include bi-component fibers comprising polyethylene (PE) and polyethylene terephthalate (PET) components or polyethylene terephthalate and co-polyethylene terephthalate components. The components of the bi-component fiber may be arranged in a sheath-core configuration, a side-by-side configuration, an eccentric sheath-core configuration, a trilobal arrangement, or any other desired configuration. In some configurations, the polymer fibers may include bi-component fibers having PE/PET components arranged in a concentric, sheath-core configuration, wherein the polyethylene component forms the sheath.

While other materials may be useful in creating a resilient structure, it is believed that the stiffness of a PET core component in a sheath-core fiber configuration is useful for imparting resilience to the upper and lower nonwovens. In synergistic combination, a PE sheath component, having a lower melting temperature than the PET core component, may be utilized to provide inter-fiber melt/fusion bonding, effected via heat treatment of the precursor batt. This can help provide tensile strength to the web in both the MD and CD. Such inter-fiber bonds may serve to reduce fiber-to-fiber sliding, and thereby further contribute to imparting shape stability and resiliency to the material even when it is wetted.

Where a relatively higher weight fraction of polymer fibers is included, more connections within the structure may be created via heat treatment. However, too many connection points can impart greater stiffness to the upper and lower nonwovens than may be desirable. For this reason, selecting the weight fraction of the polymer fibers may involve prioritizing and balancing competing needs for stiffness and softness in the upper and lower nonwovens.

As noted above, the upper and lower nonwovens may additionally include polymer fibers which increase resiliency of the upper and lower nonwovens. The resilient polymer fibers may help the upper and lower nonwovens maintain permeability and compression recovery. In another configuration, the upper and lower nonwovens may comprise resilient polymer fibers having varying cross sections, e.g., round and hollow spiral, and/or may comprise resilient fibers having varying sizes.

The polymer fibers may be resilient and may be spun from any suitable thermoplastic resin, such as polypropylene (PP), polyethylene terephthalate (PET), or other suitable thermoplastics known in the art. The average staple length of the resilient polymer fibers may be selected to be in the range of greater than about 10 mm, from about 20 mm to about 100 mm, or about 30 mm to about 50 mm, or about 35 mm to about 50 mm. The resilient polymer fibers may have any suitable structure or shape. For example, the resilient polymer fibers may be round or have other shapes, such as spiral, scalloped oval, trilobal, scalloped ribbon, and so forth. Further, the resilient polymer fibers may be solid, hollow, or multi-hollow. The resilient polymer fibers may be solid and round in shape. In other suitable examples, resilient polymer fibers may include polyester/co-extruded polyester fibers. Other suitable examples of resilient polymer fibers may include bi-component fibers such as polyethylene/polypropylene, polyethylene/polyethylene terephthalate, polypropylene/polyethylene terephthalate bicomponent fibers. These bi-component fibers may have a sheath/core configuration.

The resilient polymer fibers may also be polyethylene terephthalate (PET) fibers, or other suitable non-cellulosic fibers known in the art. PET fibers may be imparted with any suitable structure or shape. For example, the PET fibers may be round or have other shapes, such as spiral, scalloped oval, trilobal, scalloped ribbon, hollow spiral, and so forth. The PET fibers may be solid, hollow or multi-hollow. In one particular example, PET fibers may be hollow in cross section and have a curl or spiral configuration along their lengths. Optionally, the resilient polymer fibers may be spiral-crimped or flat-crimped. The resilient polymer fibers may have an average crimp count of about 4 to about 12 crimps per inch (cpi), or about 4 to about 8 cpi, or about 5 to about 7 cpi, or about 9 to about 10 cpi. Particular non-limiting examples of resilient polymer fibers may be obtained from Wellman, Inc. (Ireland) under the trade designations H1311 and T5974. Other examples of suitable resilient polymer fibers are disclosed in U.S. Pat. No. 7,767,598.

The stiffening polymer fibers and resilient polymer fibers should be carefully selected. For example, while the constituent polymers forming the stiffening polymer fibers and the resilient polymer fibers may have similarities, resilient polymer fiber composition should be selected such that their constituents' melting temperature(s) is/are higher than that of the bondable components of the stiffening polymer fibers. Otherwise, during heat treatment, resilient polymer fibers could bond to stiffening polymer fibers and vice versa, and thereby an overly rigid structure. To avoid this risk where the stiffening polymer fibers include bicomponent fibers, e.g., core-sheath configuration fibers with a sheath component of relatively lower melting temperature at which fusion bonding will occur, the resilient polymer fibers may comprise the constituent chemistry of only the core, which may be a polymer having a relatively higher melting temperature.

Nonwoven performance can be impacted by a combination of the nonwoven fiber polymer choice, fiber properties and how the fibers are arranged or connected. Nonwoven selection can impact the absorbent article's ability to recover its shape following compression, bending and extension (stretching) forces present in-use with body motion. If the fibers are short fibers (less than about 10 mm), then they are likely to irreversibly rearrange under extension and compressive forces. The rearranging (changing their orientation/ state) of fibers in a fiber matrix dissipates the tensile (elongation) or compressive forces so that the energy used to affect the deformation is no longer available for recovery to the original shape. Longer fiber networks (typically greater than about 10 mm but less than about 100 mm) can dissipate the tensile/compressive forces typical of bodily motions along the fiber length and across the structure. As a result, the imparted forces are available to recover the structure to its original state. Longer fiber networks composed of finer fibers (less than about 15 to about 20 microns and about 2.0 Dtex) more readily elongate and compress. As a result, the fluff/AGM structure can deform more readily (and to a higher degree) but the energy associated with these deformations is relatively small and insufficient to carry the structure back to its original state. Thicker fiber, such as greater than about 2.0 Dtex to about 10 Dtex, are both flexible under bodily forces but provide sufficient fiber and web recovery energy to return the structure to its original state.

The fiber arrangement in a long fiber network from a structural standpoint can impact the performance of the absorbent articles containing these nonwovens. Long fiber webs of thicker fibers are typically loftier than a conventional thin spunbond nonwoven web composed of continuous fine fibers that are closely spaced and physically bonded together. Creating a web of thicker fibers arranged in a more randomized orientation such as those that can be achieved via carding, hydro-entangling and needling are able to elongate and compress, whereby the fibers only temporary adjust their arrangement (space between the fibers exist for these arrangements) and are able to carry/store the deformation forces and this energy is available for recovering the structural shape.

Additionally, finer (less than about 2.0 Dtex) synthetic fibers such as BiCo and PP fibers commonly found in spunbond are closely spaced, relatively parallel aligned and closely bonded together. The bonded fibers within these spunbond webs are so interconnected (with closely spaced point bonds) that in tensile (elongation) the fibers at the polymer level are forced to stretch this results in polymer chains within the fiber permanently rearranging and as a result the fibers themselves potentially remaining permanently elongated (permanently strained) and no longer able to recover to their initial state.

In some configurations, the polymer fibers in the upper nonwoven layer and the polymer fibers of the lower nonwoven layer may be different. In some configurations, the polymer fibers of the upper nonwoven layer and the polymer fibers of the lower nonwoven layer may be the same.

Suitable nonwoven materials examples include, but are not limited to, the following materials: (i) a 40 gsm carded resilient nonwoven material produced by Yanjan China (material code; ATB Z87G-40-90) which is a carded nonwoven composed of a blend of 60% 2 Dtex and 40% 4 Dtex BiCo (PE/PET) fibers. The fibers are bonded (ATB=Through 'hot' Air Bonded) to create a wet resilient network. The material basis weight is 40 gsm and has a caliper (under 7 Kpa) of about 0.9 mm. Without being limited by theory, it is believed that because of the presence of the 4 Dtex BiCo fibers and the fiber-to-fiber bonded BiCo network, the material has a low Permanent Strain (less than about 0.013 mm/mm) and a sufficient Dry Recovery Energy (greater than about 0.03 N*mm) in the Wet and Dry CD Ultra Sensitive 3 Point Bending Method; (ii) a 55 gsm resilient spunlace material produced by Sandler Germany (material code: 53FC041001), which is a hydro-entangled nonwoven that is produced via a carding step (like the nonwoven described above) followed by hydro-entangling with an elevated drying step (as described in US Patent Publication No. 2020/0315873A1) that creates both an entangled and BiCo bonded resilient network. It comprises a fiber blend of 30% 10 DTex HS-PET, 50% 2.2 Dtex BiCo (PE/PET), and 20% 1.3 Dtex rayon. As such the material has a low Permanent Strain (less than about 0.013 mm/mm) and a sufficient Dry Recovery Energy (greater than about 0.03 N*mm) in the Wet and Dry CD Ultra Sensitive 3 Point Bending Method; and (iii) a 50 gsm resilient spunlace material produced by Sandler Germany (material code: 53FC041005 opt82), which is a hydro-entangled nonwoven that is produced via a carding step (like the nonwoven described above) followed by hydro-entangling with an elevated drying step (as described in US Patent Publication No. 2020 0315873A1) that creates both an entangled and BiCo bonded resilient network. It comprises a fiber blend of 60% 5.8 Dtex BiCo (PE/PET), 20% 3.3 Dtex tri-lobal 'structural' rayon, and 20% 1.3 Dtex rayon. As such, the material has a low Permanent Strain (less than about 0.013 mm/mm) and a sufficient Dry Recovery Energy (greater than about 0.03 N*mm) in the Wet and Dry CD Ultra Sensitive 3 Point Bending Method. While this material has 40% rayon that can soften when wet, the use of structural tri-lobal rayon fibers may help structural stability in the wet state.

In combination with adjustment of pore size, volume, and number via selection of appropriate fiber size, basis weight, and extent of consolidation, the manufacturer may wish to select fiber constituents for having particular surface chemistry(ies), e.g., fibers with hydrophobic surfaces, hydrophilic surfaces, or a blend of differing fibers and/or z-direction stratification or gradient thereof. Fibers having hydrophilic surfaces will tend to attract and move aqueous components of menstrual fluid there along in a manner conducive to wicking and rapid fluid acquisition following discharge. At the same time, however, a predominance of hydrophilic fibers surfaces within the topsheet may increase a tendency of the topsheet to reacquire fluid from absorbent components beneath (rewet), which can cause an undesirable wet feel for the user. On the other hand, fibers having hydrophobic surfaces will tend to repel aqueous components of menstrual fluid and/or resist movement of fluid along their surfaces, thereby tending to resist wicking—but also to resist rewetting. The manufacturer may wish to seek an appropriate balance in selecting constituent fibers having hydrophilic surfaces, fibers having hydrophobic surfaces, or a blend and/or z-direction stratification thereof, in combination with fiber size, fiber consolidation level, and resulting topsheet pore size, volume and number, for any particular product design.

As shown in FIG. 3, the inner core layer 200 is disposed between the upper nonwoven layer 210 and the lower nonwoven layer 220. The inner core layer 200 is produced in an airlaying process. Streams of cellulose fiber and AGM are carried on a fast moving airstream and deposited into a three dimensionally shaped pocket on a rotating forming drum with a vacuum below to draw the cellulose and AGM into the pocket in a laydown station. This shaped pocket provides the actual physical shape of the absorbent core structure. The upper or lower nonwoven may be first introduced onto the forming drum and under the vacuum they are drawn into the 3 dimensional pocket shape. In this case, the cellulose and AGM material stream is deposited on the upper (or lower nonwoven material) directly in the forming station. Prior to entering the forming station, the nonwoven is coated with an adhesive to provide a stronger connection of the cellulose and AGM to the nonwoven layer. On exiting the laydown section, the second remaining nonwoven layer is combined with the nonwoven carrying the cellulose and AGM layer exiting the laydown section. This second remaining nonwoven (either upper or lower nonwoven depending on what nonwoven is run through the laydown section) is precoated with adhesive to enable a perimeter seal and to better integrate the cellulose and AGM without hindering the flow of liquid into the cellulose and AGM matrix. In another approach, a nonwoven is not first introduced into the forming station and the cellulose and AGM mass is held on the forming drum under vacuum until it is ejected onto either the upper or lower nonwoven layer that has an adhesive applied as detailed above and then sealed with the second remaining nonwoven to create the absorbent core structure. The width of the upper and lower nonwoven webs are chosen to be wider than the maximum width of the shaped cellulose and AGM matrix so as to enable an effective perimeter seal where the two nonwovens connect, at least on the left and right most sides of the absorbent core structure.

The inner core layer may comprise any of a wide variety of liquid absorbent materials commonly used in absorbent articles, such as comminuted wood pulp, which is generally referred to as airfelt. One suitable absorbent core material is an airfelt material which is available from Weyerhaeuser Company, Washington, USA, under Code No. FR516. Examples of other suitable liquid absorbent materials for use in the absorbent core may include creped cellulose wadding; meltblown polymers including coform; chemically stiffened, modified or cross-linked cellulosic fibers; synthetic fibers such as crimped polyester fibers; peat moss; cotton, bamboo; absorbent polymer materials; or any equivalent material or combinations of materials, or mixtures of these.

Absorbent polymer materials for use in absorbent articles typically comprise water-insoluble, water-swellable, hydrogel-forming crosslinked absorbent polymers which are capable of absorbing large quantities of liquids and of retaining such absorbed liquids under moderate pressure.

The absorbent polymer material for the absorbent cores according to the present disclosure may comprise superabsorbent particles, also known as "superabsorbent materials" or as "absorbent gelling materials". Absorbent polymer materials, typically in particle form, may be selected among polyacrylates and polyacrylate based materials, such as for example partially neutralized, crosslinked polyacrylates. The term "particles" refers to granules, fibers, flakes, spheres, powders, platelets and other shapes and forms known to persons skilled in the art of superabsorbent particles. In some aspects, the superabsorbent particles may be in the shape of fibers, i.e., elongated, acicular superabsorbent particles.

In some configurations, the inner core layer may comprise cellulosic fibers and superabsorbent particles. The inner core layer may comprise from about 50% to about 85% cellulosic fibers, or from about 55% to about 80%, or from about 60% to about 75%, all by weight of the inner core layer. The inner core layer may comprise from about 15% to about 50% superabsorbent particles, or from about 20% to about 40%, or from about 25% to about 35% all by weight of the inner core layer. Preferably, the inner core layer may comprise from about 125 gsm to about 400 gsm cellulosic fibers.

In some configurations, the inner core layer may comprise from about 50% to about 85% cellulosic fibers and from about 15% to about 50% superabsorbent particles. The resulting absorbent core structure may have an average density of between about 0.045 $g/cm^3$ and about 3, and/or between 0.045 $g/cm^3$ and 0.12 $g/cm^3$. The absorbent article may have an average density of between about 0.045 $g/cm^3$ and about 0.16 $g/cm^3$.

The absorbent core structures may compress and recover their original shape following the compression step. Suitable absorbent core structures require a low force to compress (less resistance) and the structure is able to recover its shape as the user, in a cyclic fashion, compresses and releases the compressive force with various body movements. To achieve this the structure sustains sufficient recovery energy following multiple cyclic compressions. Without sufficient recovery energy the structure remains in a compressed bunched state with insufficient force (stored energy) to recover.

As shown in FIGS. 1, 2A, 2B, 4, and 5 the absorbent core structure may comprise a plurality of structural bond sites 15. The structural bond sites 15 may be symmetric and/or asymmetrical and may be any shape including, but not limited to, circles, ovals, hearts, diamonds, triangles, squares, stars, and/or X shaped. The structural bond sites 15 can be on the absorbent article and/or on the absorbent core structure. In some configurations, the structural bond sites can have a bond area of from about 2 mm$^2$ to about 5 mm$^2$. In some configurations, the total structural bond area can be from about 0.5% to about 5%, or from about 0.75% to about 4.5%, or from 1% to about 4% of the absorbent core structure, as measured according to the Structural Bond Sites Pattern Spacing and Area Measurement Method. In some configurations, the total structural bond area may be from about 1% to about 4% of the absorbent article as measured according to the Structural Bond Sites Pattern Spacing and Area Measurement Method. The average distance between the structural bond sites may be from about 10 mm to about 32 mm. In some configurations, the average distance between the structural bond sites may be greater than about 20 mm. In some configurations, the structural bond sites may have a maximum width of from about 1 mm to about 6 mm, or from about 1.5 mm to about 5 mm, or from about 2 mm to about 4 mm. Without being limited by theory, it is believed that the average distance between structural bond sites and/or the size of the structural bond sites may help to maintain the structural integrity of the absorbent core structure without creating an undesirable stiffness that may inhibit the ability of the absorbent article to conform to the body.

In some configurations, the structural bond sites may be distributed across the absorbent article and/or absorbent core structure or they may be clustered in regions of the absorbent article and/or absorbent core structure. In some configurations, the structural bond sites may be clustered in the middle region of the absorbent article and/or absorbent core structure. In some configurations, the middle region of the absorbent article and/or absorbent core structure may be free from structural bond sites and can be surrounded by an area of structural bond sites and/or embossing.

In some configurations, the structural bond sites 15 may join the topsheet 110, the upper nonwoven layer 210, the absorbent core structure 10, and the lower nonwoven layer 220. In some configurations, the structural bond sites 15 may join the upper nonwoven layer 210, the absorbent core structure 10, and the lower nonwoven layer 220.

Suitable absorbent articles and/or absorbent core structures may comprise an upper nonwoven layer and lower nonwoven layer that are closer together in the Z direction at the structural bond sites but are not melted together. Since these structural bond sites are not melted together, they may not permanent in nature and rather may intermingle the materials within the structural bond site. In some configurations, the structural bond sites may be substantially free of fusion bonds.

While the shape of the structural bond sites can be any shape, suitable shapes may be more detailed shapes such as asymmetrical shapes (versus simple dots).

The absorbent article 20 may be resilient and conformable and may deliver a superior in use experience without bunching and/or compressing. The absorbent article may be exposed to bodily forces and can recover to its original state. The absorbent article may have a CD Dry Modulus of between about 0.07 and 0.30 N/mm$^2$ as measured in the Wet and Dry CD and MD 3 Point Bend Method, or from about 0.10 to about 0.25 N/mm$^2$, or from about 0.10 to about 0.20 N/mm$^2$.

The absorbent article may have a of Dry Caliper between about 2.0 mm and about 6.0 mm, or from about 2.0 mm and about 4.5 mm as measured according to the Wet and Dry CD and MD 3-Point Method, or from about 2.50 mm to about 4.0 mm, or from about 2.75 mm to about 3.5 mm. In some configurations, the absorbent article may have a CD Dry Modulus of between about 0.07 and 0.30 N/mm$^2$ and a Dry Caliper between about 2.0 mm and about 4.5 mm as measured according to the Wet and Dry CD and MD 3-Point Method, or a CD Dry Modulus of between from about 0.10 to about 0.25 N/mm$^2$ and a Dry Caliper of from about 2.50 mm to about 4.0 mm, or a CD Dry Modulus of between about from about 0.10 to about 0.20 N/mm$^2$ and a Dry Caliper of from about 2.75 mm to about 3.5 mm. The absorbent article may have a CD Dry Bending Stiffness of between about 10.0 to about 30.0 N*mm$^2$ as measured in the Wet and Dry CD and MD 3 Point Bend Method, or about 10.0 and about 25.0 N*mm$^2$, or about 10 to about 20 N*mm$^2$, or about 13 to about 20 N*mm$^2$. Particularly suitable absorbent articles include those having a CD Dry Bending Stiffness of between about 10.0 and about 30.0 N*mm$^2$ and a Dry Caliper of from about 2.5 mm to about 4.0 mm as measured according to the Wet and Dry CD and MD 3-Point Method, or a CD Dry Bending Stiffness of about 10 to about 25 N*mm$^2$ and a Dry Caliper of between about 2.5 and 4.0 mm, or a CD Dry Bending Stiffness about 13 to about 30 N*mm$^2$ and a Dry Caliper of from about 2.75 mm to about 3.5 mm.

The absorbent article may have a 5$^{th}$ Cycle Wet Energy of Recovery of from about 1.0 to about 3.5 N*mm, or about 1.5 to about 3.0 N*mm, or about 1.5 to about 2.8 N*mm. Particularly suitable absorbent articles may have a 5$^{th}$ Cycle Wet Energy of Recovery of between about 1.0 and 3.5 N*mm and a 5$^{th}$ Cycle Wet % Recovery of from about 29% to about 40%, or a 5$^{th}$ Cycle Wet Energy of Recovery of from about 1.5 to about 3.0 N*mm and a 5$^{th}$ Cycle Wet % Recovery of from about 29% to about 40%, or a 5$^{th}$ Cycle Wet Energy of Recovery from about 1.5 to about 2.75 N*mm and a 5$^{th}$ Cycle Wet % Recovery of from about 29% to about 40%.

Absorbent articles composed of the absorbent core structures as disclosed within may also need to deliver a dry touch to the consumer following the addition of fluid as measured by the light touch rewet method. Absorbent core structures and absorbent articles meeting the above characteristics are designed to comfortably and gently conform more closely and more completely to the wearer's complex anatomical genital shape. Such absorbent articles therefore may also need to be dry to the touch following discharge so as not to irritate the sensitive genital tissues. As such absorbent articles described herein may also maintain a Light Touch Rewet value of less than about 0.15 grams, or less about 0.12 grams, or from about 0 to about 0.15 grams, or from about 0 to about 0.12 grams.

Figure 2A:
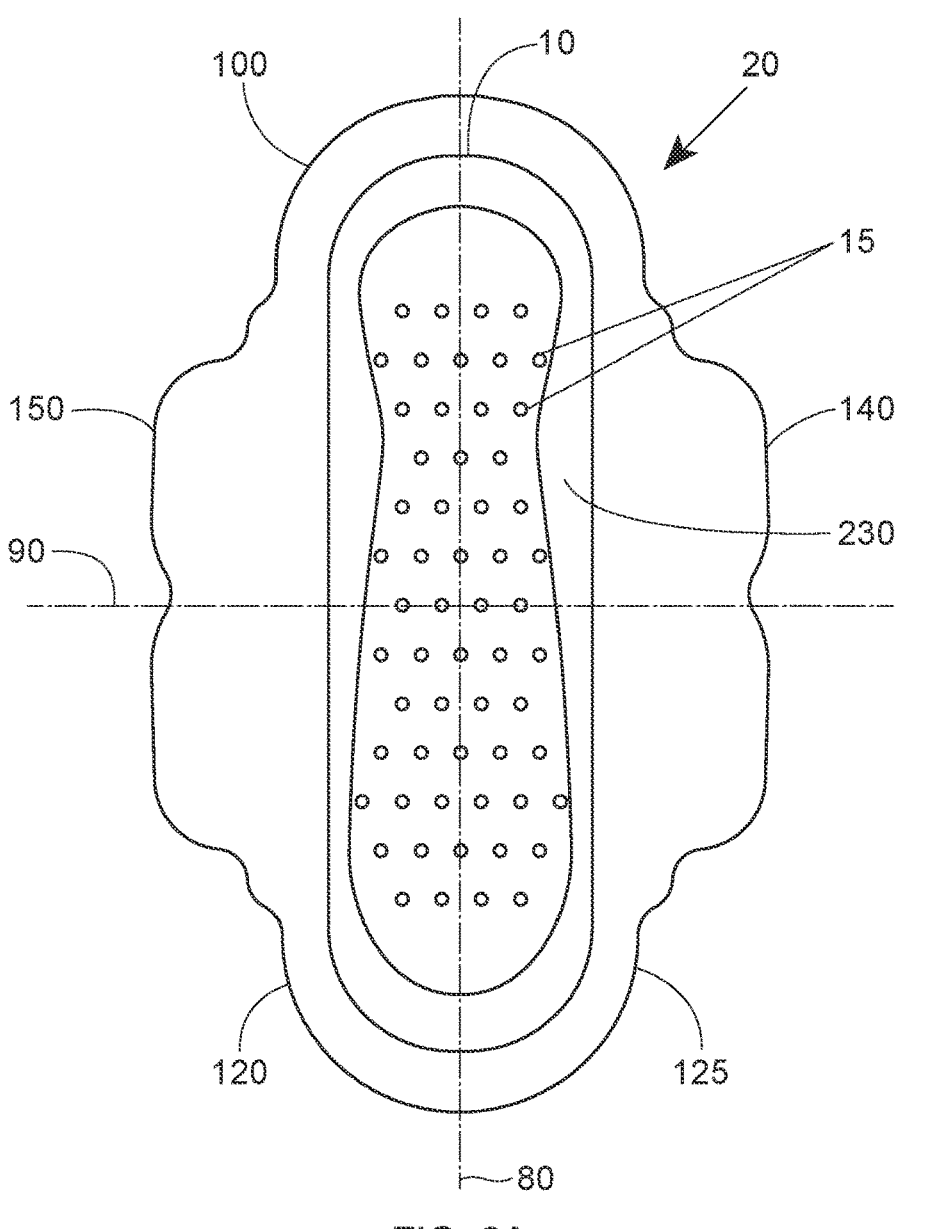
FIG. 2A is a representation of an absorbent article in accordance with the present disclosure.
Figure 2B:
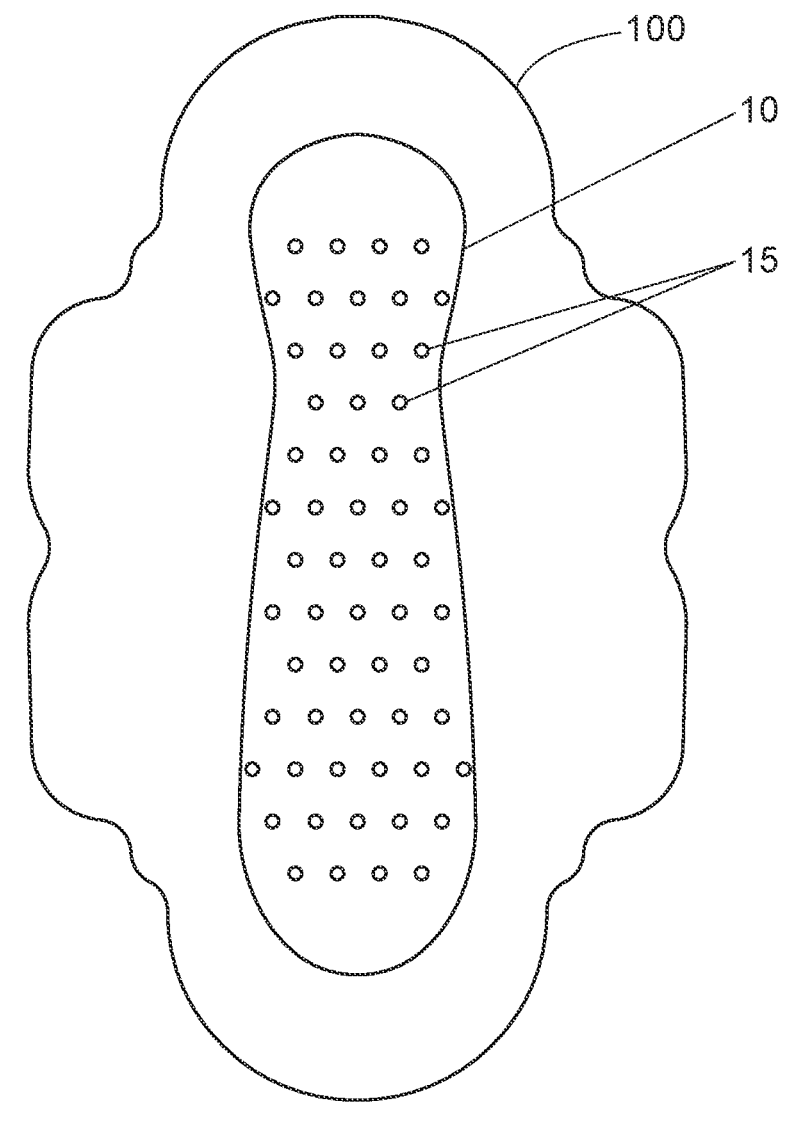
FIG. 2B is another representation of an absorbent article in accordance with the present disclosure.

As shown in FIGS. 2A and 2B, the absorbent article 20 further comprises a chassis 100 comprising an absorbent core structure 10. The absorbent core structure 10 and/or inner core layer 200 may comprise a generally hourglass shape. However, any suitable shape may be utilized. Some examples include offset hourglass (one end is wider than an opposite end and a narrowed mid-section between the ends), bicycle seat shape (one end and central portion are narrower than second end), etc. Side edges 120 and 125 may follow the general contour of the absorbent core structure. So where, the absorbent core structure has an hourglass shape the side edges of the absorbent article 120, 125 may be arranged in an hourglass shape as well. However, forms are contemplated where the side edges 120 and 125 are generally straight or slightly curved such that they do not follow the contour of the absorbent core structure. Additional details are discussed hereafter. The absorbent article 20 may be symmetric about the longitudinal centerline 80 or asymmetric about the longitudinal centerline 80. Similarly, the absorbent article 20 may be symmetric about the lateral centerline 90 or asymmetric about the lateral centerline 90.

Figure 6:
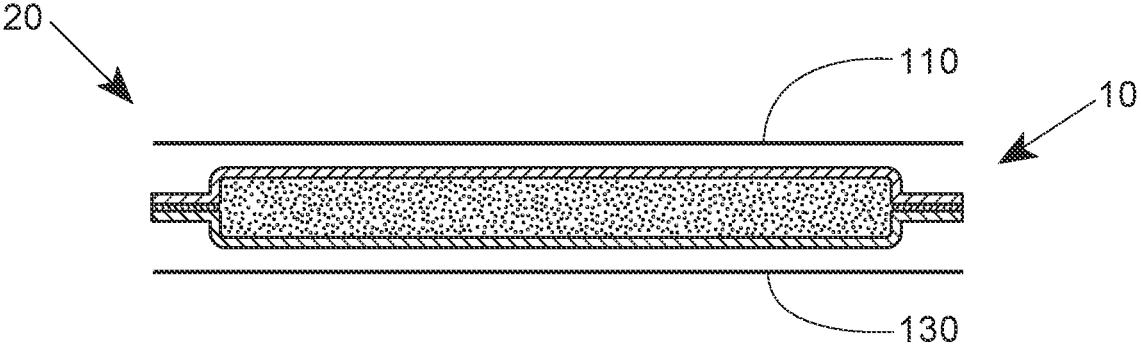
FIG. 6 is a cross section of an absorbent article in accordance with the present disclosure.
Figure 7A:
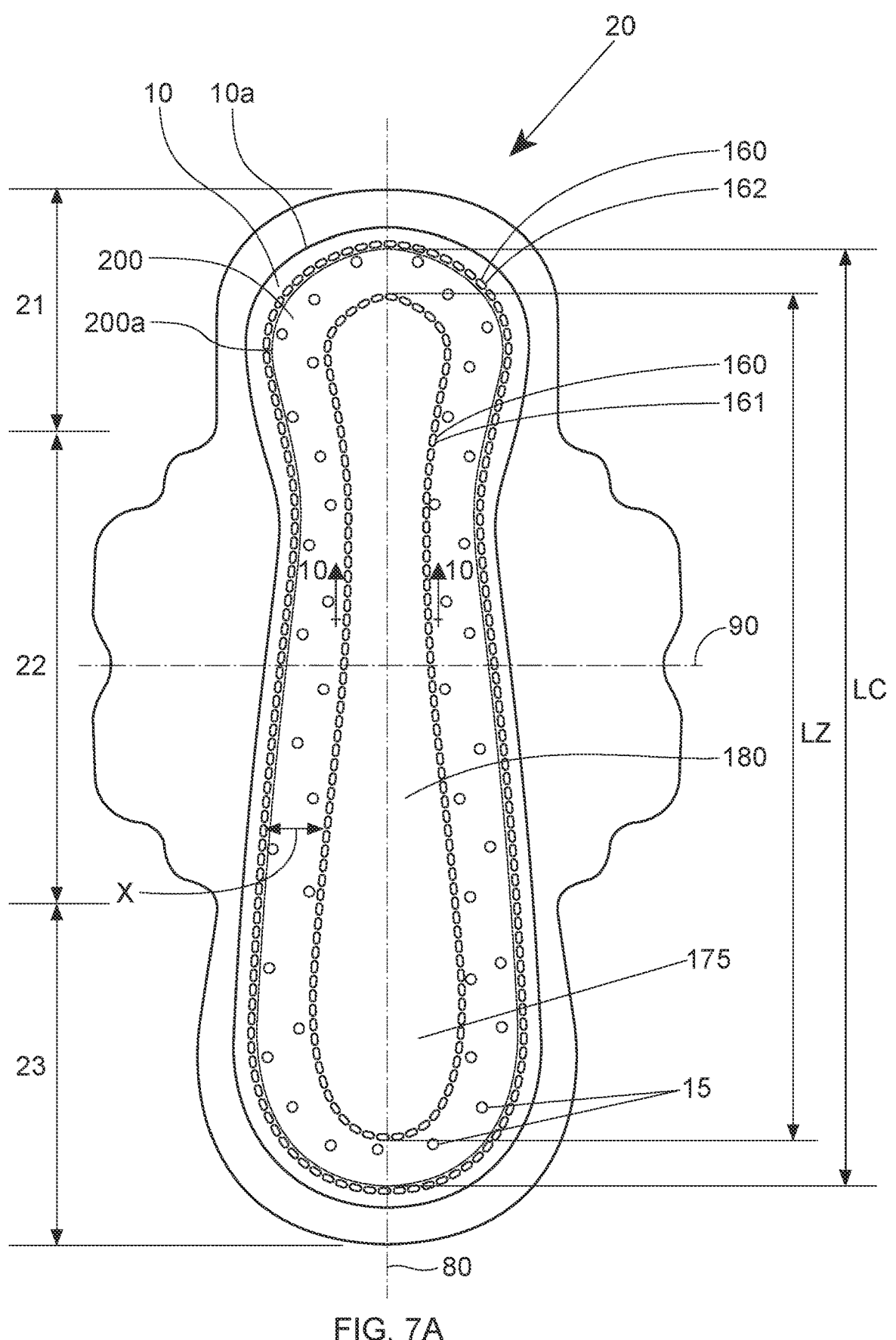
FIG. 7A is a top view of a representation of an absorbent article with flex bond channel regions in accordance with the present disclosure.
Figure 7B:
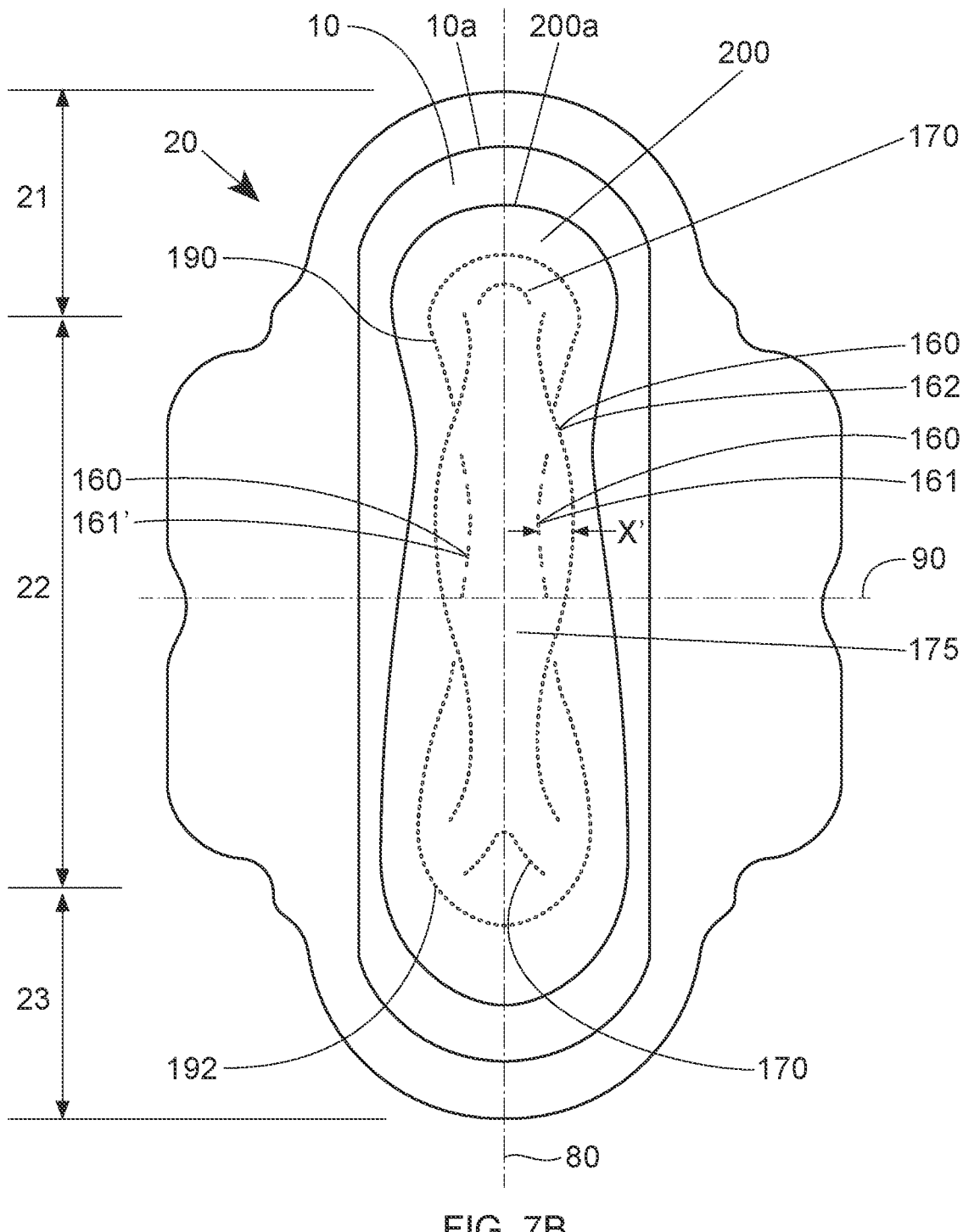
FIG. 7B is a top view of another representation of an absorbent article with flex bond channel regions in accordance with the present disclosure.
Figure 8:
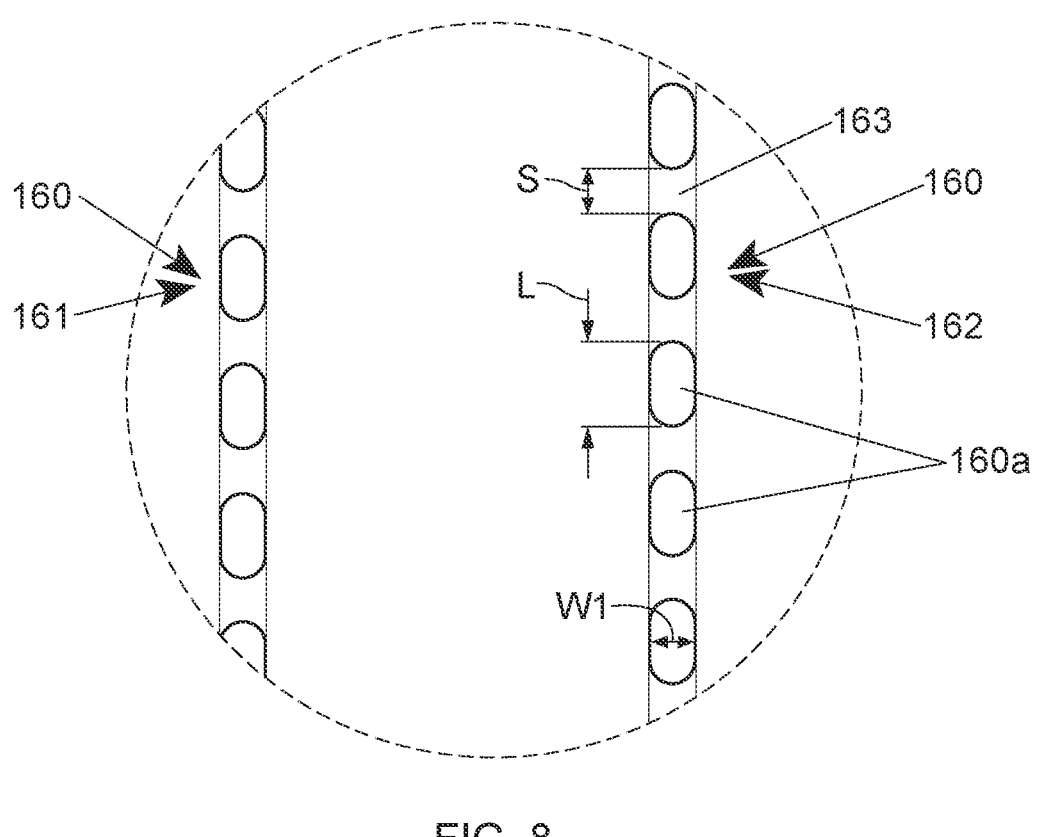
FIG. 8 is an enlarged top view illustration of the surface of an absorbent article that includes flex bond channel regions.
Figure 9:
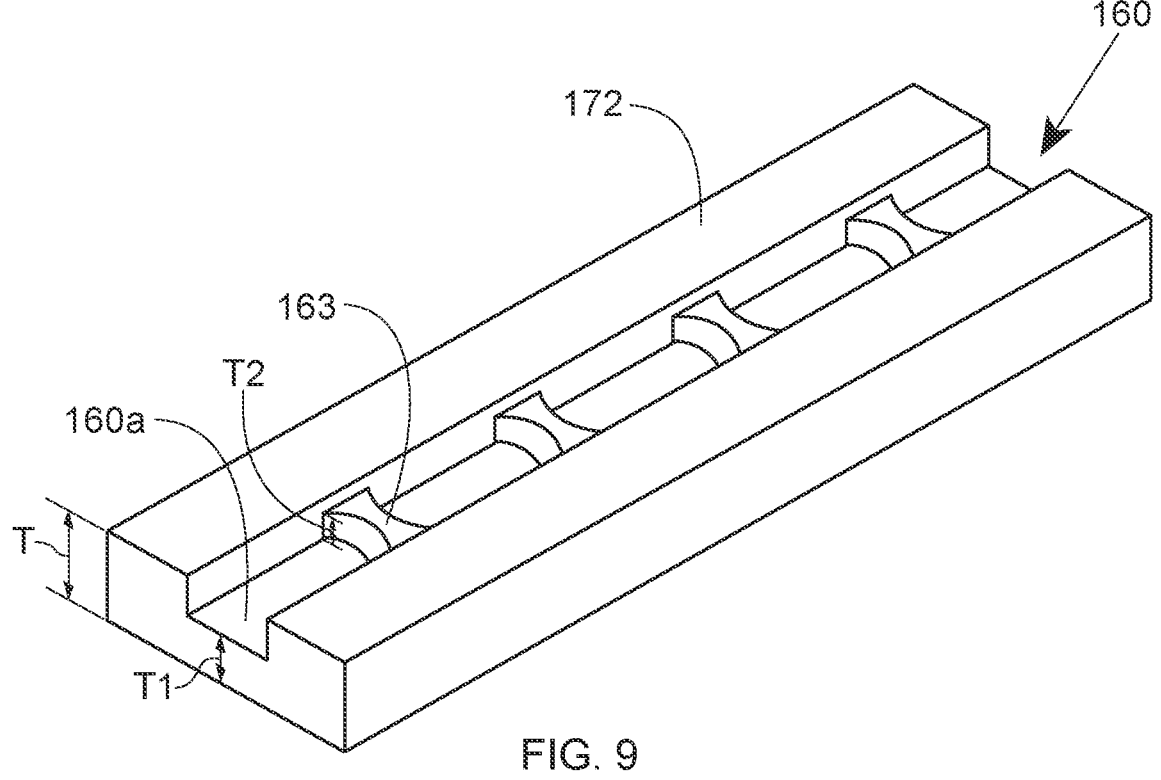
FIG. 9 is a perspective view illustration of a flex bond channel region in an absorbent article in accordance with the present disclosure.
Figures 10A, 10B:
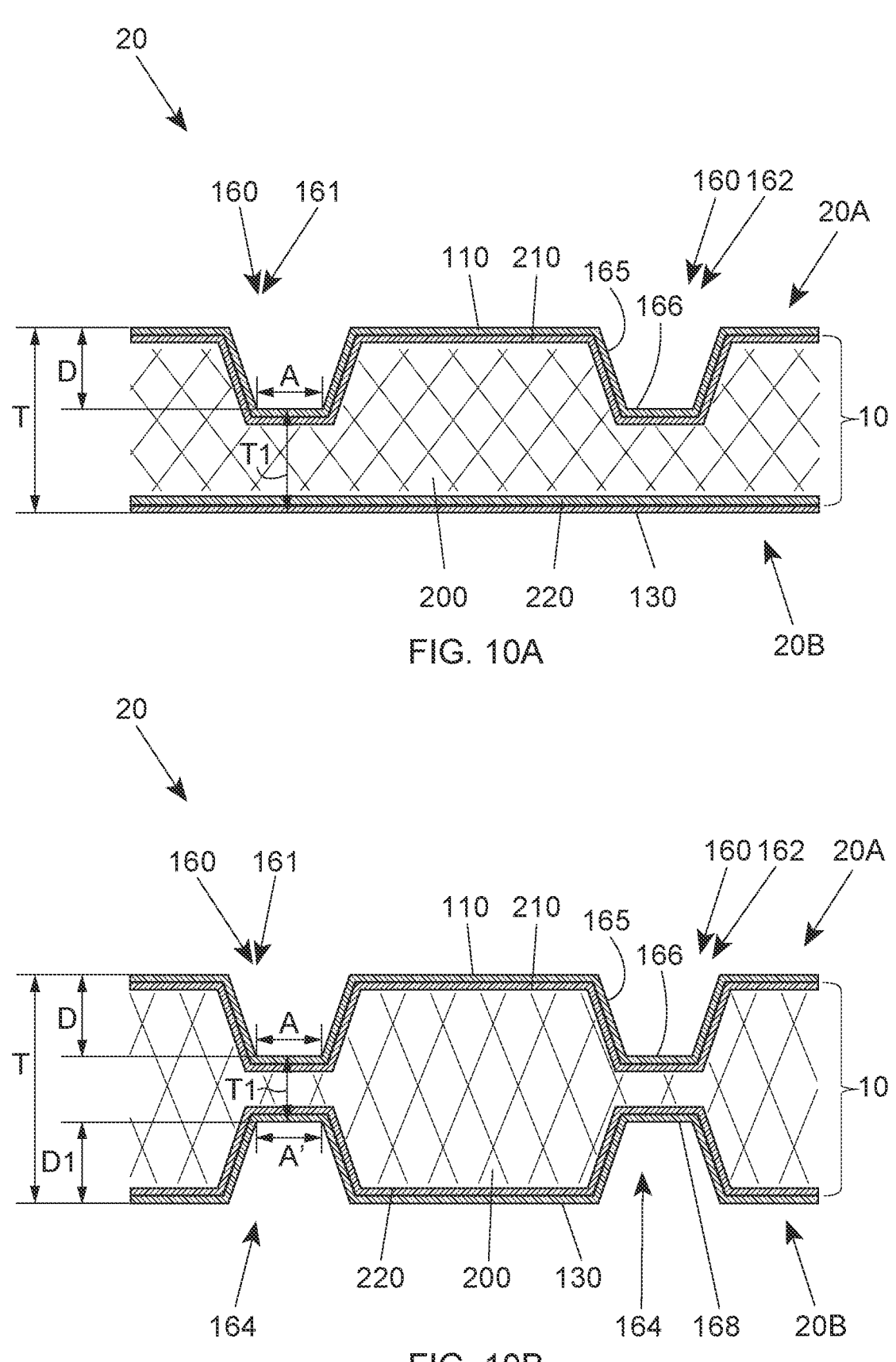
FIGS. 10A and 10B are partial cross-sectional views of an absorbent article comprising flex bond channel regions in accordance with various non-limiting configurations of the present disclosure, taken about line 10-10 of FIG. 7A.

FIG. 6 is a cross-section view of an absorbent article 20 according to the present disclosure. FIGS. 7A and 7B are top views of absorbent articles 20 according to the present disclosure. FIG. 8 is an enlarged top view illustration of the flex bond channel regions shown in FIG. 7A. FIG. 9 is a perspective view illustration of a flex bond channel region formed in an absorbent article. FIGS. 10A and 10B are partial cross-sectional views of absorbent articles comprising flex bond channel regions in accordance with various non-limiting embodiments of the present disclosure, taken about line 10-10 of FIG. 7A.

As mentioned above, and shown in FIG. 6, absorbent article 20 may comprise a topsheet 110, a backsheet 130, and an absorbent core structure 10 positioned between the topsheet 110 and the backsheet 130. As shown in FIG. 7A, the absorbent article 20 may also comprise one or more flex bond channel regions 160. At least some or all of the flex bond channel regions 160 may be permanent channels, meaning their integrity is at least partially maintained both in the dry state and in the wet state. The flex bond channel regions 160 may be a continuous depression and/or may comprise a series of individually compressed, closely spaced flex bond embossments.

The flex bond channel regions 160 may have any configuration, e.g., one or more straight line-like shape extending along the longitudinal centerline 80, one or more curved shape generally along the longitudinal centerline 80, an oval shape, a rectangle shape, a triangle shape, a polygonal shape, or any other shape. In some configurations, the flex bond channel regions 160 may extend substantially longitudinally, which means that each flex bond channel region extends more in the longitudinal direction than in the lateral direction, or at least twice as much in the longitudinal direction than in the lateral direction (as measured after projection on the respective axis). In some configurations, the flex bond channel regions 160 may extend substantially laterally, which means that each flex bond channel region extends more in the lateral direction than in the longitudinal direction, or at least twice as much in the lateral direction than in the longitudinal direction (as measured after projection on the respective axis).

In some configurations, the absorbent article 20 may comprise an inner flex bond channel region 161 and an outer flex bond channel region 162. The inner and outer flex bond channel regions 161, 162 may serve as a hinge structure in the absorbent article, which may help enable the absorbent article to flex both longitudinally and laterally and thereby better conform to the wearer's anatomy. The inner and outer flex bond channel regions 161, 162 may also serve as a visual signal of a fluid barrier.

The inner flex bond channel region 161 may be curved and/or arcuate, and may run substantially parallel to the longitudinal centerline 80 of the absorbent article. In other configurations, the inner flex bond channel region 161 may be substantially straight. In some configurations, the inner flex bond channel region 161 may be concave towards the longitudinal centerline 80, as, for example, represented in FIG. 7B for the pair of inner flex bond channel regions 161, 161', such that they bend towards the longitudinal centerline 80. The inner flex bond channel region 161 may also be convex, such that they bend away from the longitudinal centerline 80, or have any other suitable arrangement.

The absorbent article 20 and the absorbent core structure 10 each include a front end region 21, a back end region 23, and a middle region 22 disposed intermediate the front end and the back end regions. The middle region 22 may comprise a central usage area 175. The inner flex bond channel region 161 may be present in the middle region 22, or part thereof, and part of the front end region 21 and/or back end region 23. In some configurations, the inner flex bond channel region 161 may extend longitudinally from the front end region 21 to the back end region 23. The absorbent article 20 may comprise one or more inner flex bond channel regions 161, such as two, three, four, five or six.

In some configurations, the inner flex bond channel region 161 may be positioned in at least the middle region 22 and may form a closed loop substantially surrounding the central usage area 175, as for example, represented in FIG. 7A. In some configurations, the absorbent article may comprise a pair of inner flex bond channel regions 161, 161' with at least a portion of the central usage area 175 disposed between the pair of inner flex bond channel regions. When present as symmetrical pairs relative to the longitudinal centerline 80, inner flex bond channel regions 161, 161' may be spaced apart from one another over their whole longitudinal dimension (for example, as shown in FIG. 7B). In some configurations, inner flex bond channel regions 161 may be spaced apart a distance of at least about 10 mm so as not to impart a localized stiffness in the spaces between the inner flex bond channel regions. In some configuration, the distance between inner flex bond channel regions may be from about 10 mm to about 45 mm, or from about 12 mm to about 30 mm, or from about 15 mm to about 25 mm, as measured in a direction parallel to the lateral centerline 90 from the inner edge of one inner flex bond channel region to the inner edge of the opposing inner flex bond channel region.

The absorbent article may comprise structural bond sites 15 and flex bond channel regions 160. In some configurations, the central usage area 175 may be substantially free from structural bond sites 15 and may be at least partially surrounded by an area of structural bond sites and/or flex bond channel regions, such as shown in FIG. 7A. It is to be understood that the absorbent article shown in FIG. 7B may also comprise structural bond sites 15 as described above.

As shown in FIGS. 7A and 7B, the absorbent article 20 may comprise an outer flex bond channel region 162 to further increase the flexibility and fit of the absorbent article and/or to help provide a visual signal of a fluid barrier. The above description of flex bond channel regions 160 and/or inner flex bond channel regions 161 may equally apply to the outer flex bond channel region 162. In some configurations, in order to reduce the risk of fluid leakages, the outer flex bond channel region 162 may be positioned between an absorbent core structure perimeter 10a and an inner core layer perimeter 200a, as shown for example in FIG. 7A. The outer flex bond channel region 162 may be positioned outboard of the inner core layer perimeter 200a and may at least partially surround the inner core layer 200. In such a configuration, the outer flex bond channel region 162 may compress the topsheet and upper nonwoven layer towards the lower nonwoven layer without the presence of the inner core layer therebetween. In some configurations, the distance between the outer edge of the outer flex bond channel region 162 and the absorbent core structure perimeter 10a may be at least 3 mm, or from about 3 mm to about 8 mm, or from about 5 mm to about 6 mm. In other configurations, as shown for example in FIG. 7B, the outer flex bond channel region 162 may be positioned inboard of the inner core layer perimeter 200a, and may compress the topsheet, the upper nonwoven layer, and the inner core layer towards the lower nonwoven layer.

In some configurations, the outer flex bond channel region 162 may comprise a closed loop surrounding the inner flex bond channel region 161. In such a configuration, as shown in FIG. 7A, the distance "X" between the inner flex bond channel region 161 and outer flex bond channel region 162 may from about 10 mm to about 30 mm, or from about 12 mm to about 25 mm, or from about 15 mm to about 20 mm, as measured in a direction parallel to the lateral centerline 90 from the inner edge of the outer flex bond channel region 162 to the outer edge of the inner flex bond channel region 161. In other configurations, the outer flex bond channel region 162 may comprise a pair of outer flex bond channel regions positioned outboard of the inner flex bond channel region 161. In such a configuration, the distance between the inner flex bond channel region 161 and the outer flex bond channel region 162 may vary along the longitudinal length of the inner and outer flex bond channel regions 161, 162 with a maximum distance X' between the inner flex bond region 161 and the outer flex bond channel region 162 of from about 4 mm to about 15 mm, or from about 6 mm to about 12 mm, or from about 8 mm to about 10 mm, as measured in a direction parallel to the lateral centerline 90 from the outer edge of the outer flex bond channel region 162 to the outer edge of the inner flex bond channel region 161. In some configurations, the inner flex bond channel region 161 may be concave and the outer flex bond channel region 162 may be convex, which may help to improve the fit of the absorbent article by allowing the middle region to come up close to the wearer's anatomy.

As shown in FIG. 7B, the absorbent article may comprise one or more lateral secondary flex bond channel regions 170. Lateral secondary flex bond channel regions 170 may have their longer dimensions oriented predominately in the lateral direction, or even be substantially perpendicular to the longitudinal centerline 80 of absorbent article 20. Lateral secondary flex bond channel regions 170 may serve as a lateral hinge structure that can enable the absorbent article to flex laterally and thereby conform to the wearer's anatomy and/or may serve as visual barrier features. The description of flex bond channel regions 160 provided herein may equally apply to the lateral secondary flex bond channel regions 170. Lateral secondary flex bond channel regions 170 may be disposed in the front end region 21, middle region 22, and/or back end region 23. Lateral secondary flex bond channel regions 170 may have any configuration, e.g., one or more straight line-like shape extending along the lateral centerline 90, one or more curved shape generally along the lateral centerline 90, an oval shape, a rectangle shape, a triangle shape, a polygonal shape, an inverted V-shape, or any other shape. In some configurations, the lateral secondary flex bond channel regions 170 may be positioned longitudinally outboard of the outer flex bond channel regions 162 and/or the inner flex bond channel region 161. The lateral secondary flex bond channel regions 170 may have a length of from about 10 mm to about 60 mm, or from about 15 mm to about 40 mm, or from about 25 mm to about 35 mm, as measured from a first end of the secondary flex bond channel region to a second end of the secondary flex bond channel region following the curve of the secondary flex bond channel region. In some configurations, the lateral secondary flex bond channel regions 170 may be distinct and separate from the inner and outer flex bond channel regions 161, 162, as suggested in FIG. 7B.

Still referring to FIG. 7B, the absorbent article 20 may comprise a front flex bond channel region 190 positioned in the front end region 21, and/or a back flex bond channel region 192 formed in the back end region 23. The description of flex bond channel regions 160 provided herein may equally apply to the front and/or back flex bond channel regions 190, 192. The front flex bond channel region 190 and the back flex bond channel region 192 may generally u-shaped and may be positioned outboard of the inner flex bond channel regions 161, the outer flex bond channel regions 162, and/or the lateral secondary flex bond channel regions 170. In some configurations, the front flex bond channel region 190 may extend from the front end region 21 to a position adjacent to the outer flex bond channel region 162 in the middle region 22. In some configurations, the back flex bond channel region 192 may extend from the back end region 23 to a position adjacent to the outer flex bond channel region 162 in the middle region 22. As shown, front flex bond channel region 190 and back flex bond channel region 192 may be discontinuous, e.g., discrete, and may not be joined the outer or inner flex bond channel regions 162, 161. It is believed that the front flex bond channel region 190 and the back flex bond channel region 192 may help provide comfort and conformance to the absorbent article 20 in the front end region 21 and the back end region 23.

The flex bond channel region 160 may be continuous or discontinuous. Herein, "discontinuous" means the flex bond channel region can be separated by a non-channel region (i.e., a region where no channel is formed). The distance between the two succeeding flex bond channel regions (i.e., the length of the non-channel portion) may be changed depending on the product design. Without being limited by theory, it is believed that by having a non-channel region between, for example, the ends of the front flex bond channel region 190 and the outer flex bond channel 162 or between the inner flex bond channel region 161 and the outer flex bond channel region 162 may help to avoid creating an undesirable stiffness and may help to provide improved flexibility and fit of the absorbent article.

In some configurations, the inner flex bond channel region 161 and/or the outer flex bond channel region 162 may be continuous. In some configurations, the inner flex bond channel region 161 may be discontinuous and the outer flex bond channel region 162 may be continuous. Flex bond channel region 160 may have a minimum channel length of about 50 mm, as measured from a first end of the flex bond channel region to a second end of the flex bond channel region following the curve of the flex bond channel region. Without being limited by theory, it is believed that if the flex bond channel region is less than about 50 mm there may be insufficient length in the flex bond channel region to provide sufficient multi-direction flexibility to create a desired bend in the absorbent article to allow the absorbent article to fit closely to the body. It is believed that a flex bond channel region having a channel length of at least 50 mm can sufficiently affect adjacent non-channeled regions such that the absorbent article may conform and fit closely to the body. Flex bond channel region 160 may have a length of from about 50 mm to about 400 mm, or from about 60 mm to about 350 mm, or from about 75 mm to about 300 mm, or from about 100 mm to about 200 mm.

In some configurations, the inner flex bond channel region 161 may form a closed loop defining a central channel zone 180, as shown, for example, in FIG. 7A. Central channel zone 180 may have a longitudinal length "LZ", as measured in a direction parallel to the longitudinal axis from a first outermost point of the inner flex bond channel region 161 to a longitudinally opposing second outermost point of the inner flex bond channel region 161. The longitudinal length "LZ" of the central channel zone may be from about 50% to about 90% of the inner core longitudinal length "LC", or from about 60% to about 75% of the inner core longitudinal length "LC".

In some configurations, the flex bond channel regions 160 may have a channel area of from about 10 to about 20% of the inner core layer area.

Referring to FIG. 8, the flex bond channel region 160 may comprise a plurality of closely spaced flex bond embossments 160a. Flex bond land areas 163 are disposed between adjacent flex bond embossments 160a. Flex bond embossment 160a may have an embossment length "L" of from about 1.0 mm to about 4.0 mm, or from about 1.5 to about 3.75 mm, or from about 2.0 to about 3.5 mm, as measured according to the Flex Bond Embossment Length Method. Flex bond channel embossment 160a may have a width "W1" at the top surface of the topsheet of between about 1.0 to about 3.0 mm, or from about 1.25 to about 2.5 mm, or from about 1.5 to about 2.0 mm. The length "S" of flex bond land area 163 between adjacent flex bond embossments 160a may be from about 0.5 mm to about 4 mm, or from about 1.0 mm to about 3 mm, or from about 1.5 mm to about 2.5 mm, as measured according to the Flex Bond Land Area Length Method. Without being limited by theory, it is believed that the combination of the flex bond embossment length and width and/or the flex bond land area length "S" between the flex bond embossments can allow the flex bond channel region to bend/flex in multi-directions and provide a consumer preferred visual barrier while still preserving the overall flexibility and conformability of the absorbent article.

In some configurations, the flex bond embossments 160a may extend substantially parallel to the longitudinal centerline 80 of the absorbent article. In other configurations, the flex bond embossments 160a may extend substantially parallel to the lateral centerline 90 of the absorbent article.

In some configurations, the flex bond embossments 160a may be evenly spaced. In some configurations, at least a portion of the flex bond embossments 160a may be grouped in clusters of two, three, or four or more flex bond embossments, such as shown in FIG. 7B, and may have a spacing between the clusters of from about 2 mm to about 8 mm, or from about 3 mm to about 6 mm. Without being limited by theory, it is believed that such clusters of flex bond embossments may help to provide the flex bond channel region with increased flexibility in both the lateral and longitudinal direction and/or may help to improve fluid handling as fluid may be able to flow through the spacing between the clusters to other areas of the absorbent core structure.

FIG. 9 shows a perspective view of an illustration of the flex bond channel region 160 in an absorbent article, wherein the flex bond channel region 160 comprises a plurality of flex bond embossments 160a. The thickness "T2" of flex bond land areas 163 may be between about 50% to about 70% of the absorbent article thickness "T". Without being limited by theory, it is believed that reducing the thickness of the absorbent article in the z-direction along the length of the flex bond channel region (including in the flex bond land areas) can help to create an effective preferential bending line that allows the absorbent article to closely conform to the body at preferred locations and/or helps to create an effective visual barrier feature that is easily seen by the user. Non-channeled regions 172 are located adjacent to the flex bond channel region 160. The flex bond embossment 160a may have an embossment area of between about 22% to about 65% of the flex bond channel region area.

In contrast to the flex bond channel regions described herein, current absorbent articles for menstrual applications may comprise a series of point-like depressions whereby the material between the z-direction depression points recovers to a predominant degree to the uncompressed thickness of the non-channeled areas. In such structures, the channel depth between the depression points may be less than about 10% to about 25% of the channel depth at emboss points. Without being limited by theory, it is believed that such point-like depressions may not create an effective bending line to allow the article to conform closely to the body. Other current absorbent articles may comprise small physical bonding points with relatively large spacings between the bonding points. Without being limited by theory, it is believed that if the physical bonding points are relatively small (e.g., width less than about 0.5 mm) and spaced well apart (e.g., greater than about 1-4 mm), these physical bonding points will be insufficient to reproducibly drive a fit/bending direction of the absorbent article. To establish a reproducible, effective fit/bending direction, it is believed that sufficient mass should be displaced into the z-direction and there should be consistent thinning through a substantial portion of the channel region to effectively drive a preferred and consistent bending feature.

Typically, flex bond channel regions 160 may be formed by applying a compressive force to the topsheet 110, upper nonwoven layer 210, inner core layer 200, and lower nonwoven layer 220. The topsheet at the flex bond channel region is pushed down into the absorbent core structure, and the materials of the topsheet and the absorbent core structure are compressed at and below the bottom of the flex bond channel region. By this operation (which is often called "embossing process"), the flex bond channel region of the absorbent article has a relatively higher density than the non-channeled regions. As a result of compression, a flex bond channel region 160 may be formed to have an elongated depression such as a modified gutter-like shape having a pair of opposing side walls 165 and a bottom surface 166 as shown in FIGS. 10A and 10B.

In some configurations, the compressive force is applied to the topsheet 110, upper nonwoven layer 210, and lower nonwoven layer 220, creating a flex bond channel region 160 in an area with no inner core layer. The flex bond channel regions of the present disclosure can be formed by any structures and processes known in the art.

The flex bond channel regions 160 may be formed by applying a uniform (or a single level of) compression force. In some configurations, the flex bond channel region 160 can be formed by applying two or more levels of compression forces, thereby forming a stage channel structure, as disclosed for example in U.S. Pat. No. 6,563,013. In a stage channel configuration, the flex bond channel region may comprise opposing sidewalls, a first portion forming a first bottom surface and a second portion forming a second bottom surface, wherein the second bottom surface is subjacent the first bottom surface, and the second portion may be discrete and may be surrounded by the first portion.

Referring to FIGS. 10A and 10B, the wearer-facing surface 20A of absorbent article 20 may comprise flex bond channel region 160 having a dry channel depth "D" as measured according to the Flex Bond Channel Depth Method. The dry channel depth "D" of the flex bond channel region 160 may be from about 1.0 mm and about 4.0 mm, or from about 1.5 mm to about 3.5 mm, or from about 2.0 to about 3.0 mm. The flex bond channel region may have a channel depth of at least 1.0 mm. In some configurations, the dry channel depth "D" of the flex bond channel region 160 may be between about 20% to about 80% of the absorbent article thickness "T", or from about 25% to about 70% of the absorbent article thickness "T". The absorbent article thickness is measured according to the Flex Bond Channel Depth Method. Without being limited by theory, it is believed that flex bond channel regions 160 having a dry channel depth as described herein can provide improved body fit, good fluid barrier, and/or aesthetic visual barrier effects.

Referring to FIG. 10B, in some configurations, the outward-facing surface 20B of the absorbent article 20 may have a flex bond depression region 164 having a dry channel depth "D1" as measured from the surrounding area of the outward-facing surface 20B to the flex bond depression bottom wall 168. The dry channel depth "D1" of the flex bond depression region 164 may be from about 1.0 mm and about 4.0 mm, or from about 1.5 mm to about 3.5 mm, or from about 2.0 to about 3 mm. In certain configurations, the dry channel depth "D 1" of the flex bond depression region 164 in the outward-facing surface 20B may be between about 15% to about 80% of the absorbent article thickness "T", or from about 25% to about 70% of the absorbent article thickness "T". While the outward-facing surface 20B of the absorbent article 20 may not be directly contacted by the embossing device during embossing, a flex bond depression region 164 may be produced. While not being limited to theory, it is thought that the flex bond depression region 164 in the outward-facing surface 20B may be formed from the tensioning of the topsheet and the absorbent core structure. Following embossment and the removal of the embossing device, the recovery of the materials forming the topsheet and absorbent core structure can draw or pull the materials back up towards the wearer-facing surface 20A.

Flex bond channel region 160 may have a channel thickness "T1" of less than about 2.5 mm, or from about 0.5 mm to about 2.5 mm, or from about 1.0 mm to about 2.0 mm.

Flex bond channel region 160 may have a channel width "A" at the base of the channel, as measured according to the Flex Bond Channel Width Method, of between about 1.0 mm to about 3.0 mm, or from about 1.25 to about 2.5 mm, or from about 1.5 to about 2.0 mm. Flex bond depression regions 164 may have a lateral channel width "A'" at the base of the depression of between about 1.0 mm to about 3.0 mm, or from about 1.25 to about 2.5 mm, or from about 1.5 to about 2.0 mm.

In some configurations, the maximum width of structural bond site 15 may be greater than the channel width "A" of flex bond channel region 160. Without being limited by theory, it is believed that if the channel width "A" of the flex bond channel region 160 is greater than the maximum width of structural bond site 15 it may create a stiffness that may hinder the ability of the absorbent core structure and/or absorbent article to closely conform to the body.

Flex bond channel region 160 may have a channel density of less than about 0.3 g/cm$^3$, or from about 0.05 g/cm$^3$ to about 0.3 g/cm$^3$, or from about 0.1 g/cm$^3$ to about 0.25 g/cm$^3$. Without being limited by theory, it is believed that a channel density of less than about 0.3 g/cm$^3$ plastically deforms the inner core layer such that the flex bond channel region stays in a compressed state yet still allows the flex bond channel region to bend in both the lateral and longitudinal direction.

Flex bond channel region 160 may have a Dry MD Bending Resistance of less than about 0.04 N/mm as measured according to the Flex Bond Channel MD Bending Resistance Method, or from about 0.005 to about 0.035 N/mm, or from about 0.1 to about 0.030 N/mm. Without being limited by theory, it is believed that a flex bond channel region having a Dry MD Bending Resistance of greater than about 0.04 N/mm may create a stiffness that may hinder the ability of the absorbent core structure and/or absorbent article to closely conform to the body in both the longitudinal and lateral directions simultaneously.

The flex bond channel region 160 may have a Dry Flex Bond CD Bending Resistance of from about 0.005 N/mm to about 0.30 N/mm, or from about 0.01 N/mm to about 0.25 N/mm. The flex bond channel region may have a CD Bending Resistance Index of from about 1.1 to about 3.0, or from about 1.2 to about 2.5, or from about 1.5 to about 2.0.

Topsheet

Topsheet 110 may be formed of any suitable nonwoven web or formed film material. Referring back to the figures, the topsheet 110 is positioned adjacent a wearer-facing surface 20A of the absorbent article 20 and may be joined thereto and to the backsheet 130 by any suitable attachment or bonding method. The topsheet 110 and the backsheet 130 may be joined directly to each other in the peripheral regions outside the perimeter of the absorbent core structure and may be indirectly joined by directly joining them respectively to wearer-facing and outward-facing surfaces of the absorbent article or additional optional layers included with the absorbent article.

The absorbent article 20 may have any known or otherwise effective topsheet 110, such as one which is compliant, soft feeling, and non-irritating to the wearer's skin. A suitable topsheet material will include a liquid pervious material that is comfortable when in contact with the wearer's skin and permits discharged menstrual fluid to rapidly penetrate through it. Some suitable examples of topsheet materials include films, nonwovens, laminate structures including film/nonwoven layers, film/film layers, and nonwoven/nonwoven layers.

Nonlimiting examples of nonwoven web materials that may be suitable for use to form the topsheet 110 include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

The topsheet 110 may be compliant, soft feeling, and non-irritating to the wearer's skin. Further, the topsheet 110 may be liquid pervious permitting liquids (e.g., urine, menses) to readily penetrate through its thickness. Some suitable examples of topsheet materials include films, nonwovens, laminate structures including film/nonwoven layers, film/film layers, and nonwoven/nonwoven layers. Other exemplary topsheet materials and designs are disclosed in U.S. Patent Application Publication Nos. 2016/0129661, 2016/0167334, and 2016/0278986.

In some examples, the topsheet 110 may include tufts as described in U.S. Pat. Nos. 8,728,049; 7,553,532; 7,172,801; 8,440,286; 7,648,752; and 7,410,683. The topsheet 20 may have a pattern of discrete hair-like fibrils as described in U.S. Pat. No. 7,655,176 or 7,402,723. Additional examples of suitable topsheet materials include those described in U.S. Pat. Nos. 8,614,365; 8,704,036; 6,025,535; and US Patent Publication No. 2015/041640. Another suitable topsheet may be formed from a three-dimensional substrate as detailed in US 2017/0258647. The topsheet may have one or more layers, as described in US Patent Publication Nos. 2016/0167334; US 2016/0166443; and US 2017/0258651.

In some examples a topsheet 110 may be formed of a nonwoven web material of a spunbond web including single-component continuous fibers, or alternatively, bi-component or multi-component fibers, or a blend of single-component fibers spun of differing polymer resins, or any combination thereof. The topsheet may also be a formed nonwoven topsheet as disclosed in US Patent Publication No. 2019/0380887.

In order to ensure that fluid contacting the top (wearer-facing) surface of a topsheet will move suitably rapidly in a z-direction to the bottom (outward-facing) surface of the topsheet where it can be drawn into the absorbent article, it may be important to ensure that the nonwoven web material forming the topsheet has an appropriate weight/volume density, reflecting suitable presence of interstitial passageways (sometimes known as "pores") among and between the constituent fibers, through which fluid may move within the nonwoven material. In some circumstances a nonwoven material with fibers that are consolidated too densely may have insufficient numbers and/or volumes and/or sizes of pores, and the nonwoven will obstruct rather than facilitate rapid downward z-direction fluid movement. On the other hand, a nonwoven with fibers that are too large and/or not consolidated enough to provide a certain level of opacity (for purposes of concealing absorbed fluid in the layers beneath) and a substantial appearance may be negatively perceived by users.

The caliper of the topsheet material may be controlled, to balance competing needs for opacity and loft (which call for a higher caliper) vs. a limitation on the z-direction distance that discharged fluid travels through the topsheet from the wearer-facing surface to the outward-facing surface, to reach the absorbent core components below. Thus, it may be desired that the manufacture of the topsheet material be controlled to produce a topsheet material having a caliper of from about 0.20 mm to about 1.0 mm, or from about 0.25 mm to about 0.80 mm, or from about 0.30 mm to about 0.60 mm.

Secondary Topsheet (STS)

An STS layer may be included, in some circumstances, between the topsheet and the absorbent core structure to enable the absorbent core structure to readily receive a sudden discharge of fluid, and after receipt, to wick it along x- and y-directions to distribute it across the underlying absorbent core structure.

If included, an STS may be a nonwoven fibrous structure which may include cellulosic fibers, non-cellulosic fibers (e.g., fibers spun from polymer resin(s)), or a blend thereof. To accommodate the folding and lateral gathering of the absorbent article 20, and of the absorbent core structure 10, as described herein, the STS may be formed of a material that is relatively pliable (i.e., has relatively low bending stiffness).

A number of particular examples of suitable STS compositions and structures, as well as combinations thereof with suitable topsheet compositions and structures, are further described in U.S. application Ser. Nos. 16/831,862; 16/831,854; 16/832,270; 16/831,865; 16/831,868; 16/831,870; and Ser. No. 16/831,879; and U.S. Provisional Apps. Ser. Nos. 63/086,610 and 63/086,701. Additional suitable examples are described in U.S. Pat. No. 9,504,613; WO 2012/040315; and US 2019/0021917.

In some configurations, the absorbent article may be free of a secondary topsheet.

Backsheet

The backsheet 130 may be positioned beneath or subjacent an outward-facing surface of the absorbent core structure 10 and may be joined thereto by any suitable attachment methods. For example, the backsheet 130 may be secured to the absorbent core structure 10 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent core structure 10 is not joined directly to the backsheet 130.

The backsheet 130 may be impermeable or substantially impermeable by aqueous liquids (e.g., urine, menstrual fluid) and may be manufactured from a thin plastic film, although other flexible liquid impermeable materials may also be used. As used herein, the term "flexible" refers to materials which are compliant and will readily conform to the general shape and contours of the human body. The backsheet 130 may prevent, or at least substantially inhibit, fluids absorbed and contained within the absorbent core structure 10 from escaping and reaching articles of the wearer's clothing which may contact the absorbent article 20, such as underpants and outer clothing. However, in some instances, the backsheet 130 may be made and/or adapted to permit vapor to escape from the absorbent core structure 10 (i.e., the backsheet is made to be breathable), while in other instances the backsheet 130 may be made so as not to permit vapors to escape (i.e., it is made to be non-breathable). Thus, the backsheet 130 may comprise a polymeric film such as thermoplastic films of polyethylene or polypropylene. A suitable material for the backsheet 130 is a thermoplastic film having a thickness of from about 0.012 mm (0.5 mil) to about 0.051 mm (2.0 mils), for example. Any suitable backsheet known in the art may be utilized with the present invention.

Some suitable examples of materials suitable for forming a backsheet are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523; 3,989,867; 3,156,242; WO 97/24097; U.S. Pat. Nos. 6,623,464; 6,664,439; and 6,436,508.

The backsheet 130 may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881,489; 4,341,216; 4,713,068; 4,818,600; EP 203 821; EP 710 471; EP 710 472; and EP 0 793 952.

Other Features

In some configurations, the absorbent article 20 may be provided with adhesive deposits to provide a mechanism for the user to adhere the absorbent article to the inside of her underpants in the crotch region thereof. When the absorbent article 20 is packaged for shipping, handling and storage prior to use, adhesive deposits may be covered by one or more sheets of release film or paper (not shown) that covers/shields the adhesive deposits from contact with other surfaces until the user is ready to remove the release film or paper and place the absorbent article in her underpants for wear/use.

In some configurations, the absorbent article 20 may include opposing wing portions 140, 150 (FIG. 2A) on each side, extending laterally beyond longitudinal edges of the absorbent portions of the absorbent article by a comparatively greater width dimension than that of the forward and rearward portions of the absorbent article. Wings are currently commonly provided with feminine hygiene absorbent articles. As provided, they typically have deposits of adhesive applied to their outward-facing surfaces (surface are outward-facing prior to placement of the absorbent article within the user's underwear and application of the wings). The wing portions may also include deposits of adhesive as described above, which enable the user to wrap the wing portions through the leg openings of the underpants and around the inside edges thereof, and adhere the wing portions to the outward-facing surface/underside of the underpants in the crotch region, providing supplemental holding support for the absorbent article and helping guard the underpants proximate the leg edges thereof against soiling.

Test Methods

Layers of Interest

For any of the methods below in which all the component layers of an article will not be tested, the layers of interest may be separated using cryo-spray as needed from layers which will not be tested.

Strain to Break Method

The force versus displacement behavior of a sample is measured on a universal constant rate of extension test frame (a suitable instrument is the MTS Alliance using TestSuite Software, as available from MTS Systems Corp., Eden Prairie, MN, or equivalent) equipped with a load cell for which the forces measured are within 1% to 99% of the limit of the cell. The sample is subjected to tensile elongation at a constant rate (mm/sec) until it breaks, and the percent strain to break is measured. All testing is performed in a room controlled at 23° C.±3° C. and 50%±2% relative humidity and test samples are conditioned in this environment for at least 2 hours prior to testing.

The fixtures used to grip the test specimen are lightweight (<80 grams), vise action clamps with half cylinder steel versus rubber coated steel grip faces that are at least 40 mm wide. The fixtures are installed on the universal test frame and mounted such that they are horizontally and vertically aligned with one another.

The test specimen is prepared as follows. Obtain the test material by excising it from an absorbent article, if necessary. When excising the test material, do not impart any contamination or distortion to the material layer during the process. The test specimen is cut from an area on the test material that is free of any folds or wrinkles. The test specimen is 100 mm long (parallel to the lateral axis, or intended lateral axis of the article) and 25.4 mm wide (parallel to the longitudinal axis, or intended longitudinal axis of the article). In like fashion, five replicate test specimens are prepared.

Prepare the universal test frame as follows. Set the initial grip to grip separation distance to a nominal gage length of 80 mm, then zero the crosshead. Program the test frame to move the grips closer together by an intentional slack of 1 mm to ensure no pretension force exists on the test specimen at the onset of the test. (During this motion, the specimen will become slack between the grips). Next, the grips will move apart at a slack speed of 1 mm/s until the slack preload of 0.05 N is exceeded. (At this point, the crosshead position signal is used to compute the sample slack, the adjusted gage length, and the strain is defined at zero, 0.0). The grips will then move apart at a speed of 1 mm/s until the sample breaks or the extension limit of the instrument is exceeded.

The test is executed by inserting the test specimen into the grips such that the long axis of the specimen is parallel and centered with the motion of the crosshead. Start the test and continuously collect force ("load") and displacement data at a data acquisition rate of 100 Hz.

Construct a graph of load (N) versus displacement (mm). Determine the peak load from the curve, then determine the break sensitivity as follows. Determine the crosshead position at which the load signal decreases by 75% after the peak load is reached, and record as specimen final length (Lf) to the nearest 0.01 mm. The initial length of the specimen is defined by the crosshead position when the slack preload of 0.05 N is exceeded, and this value is recorded as specimen initial length (Li) to the nearest 0.01 mm. Calculate the percent strain to break as follows, and record to the nearest 1 percent.

$$\% \text{ Strain to Break} = ((Lf - Li)/Li) * 100$$

In like fashion, the procedure is repeated for all five replicate test specimens. The arithmetic mean of % strain to break among the five replicate test specimens is calculated and reported as % Strain to Break to the nearest 1 percent.

Wet and Dry CD and MD 3 Point Bend Method

The bending properties of an absorbent article test sample are measured on a universal constant rate of extension test frame (a suitable instrument is the MTS Alliance using TestSuite Software, as available from MTS Systems Corp., Eden Prairie, MN, or equivalent) equipped with a load cell for which the forces measured are within 1% to 99% of the limit of the cell. The test is executed on dry test specimens as well as wet test specimens. The intention of this method is to mimic deformation created in the x-y plane by a wearer of an absorbent article during normal use. All testing is performed in a room controlled at 23° C.±3° C. and 50%±2% relative humidity.

The bottom stationary fixture consists of two cylindrical bars 3.175 mm in diameter by 110 mm in length, made of polished stainless steel each mounted on each end with frictionless roller bearings. These 2 bars are mounted horizontally, aligned front to back and parallel to each other, with top radii of the bars vertically aligned and are free to rotate around the diameter of the cylinder by the frictionless bearings. Furthermore, the fixture allows for the two bars to be moved horizontally away from each other on a track so that a gap can be set between them while maintaining their orientation. The top fixture consists of a third cylinder bar also 3.175 mm in diameter by 110 mm in length, made of polished stainless steel mounted on each end with frictionless roller bearings. When in place the bar of the top fixture is parallel to and aligned front to back with the bars of the bottom fixture and is centered between the bars if the bottom fixture. Both fixtures include an integral adapter appropriate to fit the respective position on the universal test frame and lock into position such that the bars are orthogonal to the motion of the crossbeam of the test frame.

Set the gap ("Span") between the bars of the lower fixture to 25 mm±0.5 mm (center of bar to center of bar) with the upper bar centered at the midpoint between the lower bars. Set the gage (bottom of top bar to top of lower bars) to 1.0 cm.

The thickness ("caliper") of the test specimen is measured using a manually-operated micrometer equipped with a pressure foot capable of exerting a steady pressure of 0.1 psi±0.01 psi. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat circular moveable face with a diameter no greater than 25.4 mm. The test specimen is supported by a horizontal flat reference platform that is larger than and parallel to the surface of the pressure foot. Zero the micrometer against the horizontal flat reference platform. Place the test specimen onto the platform, centered beneath the pressure foot. The pressure foot is lowered by hand with a descent rate of 3±1 mm/s until the full weight of the pressure is exerted onto the specimen. After 5 seconds elapse, the thickness is recorded as caliper to the nearest 0.01 mm.

The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved.

The absorbent article samples are conditioned at 23° C.±3° C. and 50%±2% relative humidity two hours prior to testing. Dry test specimens are taken from an area of the sample that is free from any seams and residua of folds or wrinkles, and ideally from the center of absorbent article (intersection of longitudinal and lateral midlines). The dry specimens are prepared for MD (machine direction) bending by cutting them to a width of 50.8 mm along the CD (cross direction; parallel to the lateral axis of the sample) and a length of 50.8 mm along the MD (parallel to the longitudinal axis of the sample), maintaining their orientation after they are cut, and marking the body-facing surface (or the surface intended to face the body of a finished article). The dry specimens are prepared for CD (machine direction) bending by cutting them to a width of 50.8 mm along the MD (cross direction; parallel to the lateral axis of the sample) and a length of 50.8 mm along the CD (parallel to the longitudinal axis of the sample), maintaining their orientation after they are cut, and marking the body-facing surface (or the surface intended to face the body of a finished article). Measure the thickness of the test specimen, as described herein, and record as dry specimen caliper to the nearest 0.01 mm. Now measure the mass of the test specimen and record as dry mass to the nearest 0.001 grams. Calculate the basis weight of the specimen by dividing the mass (g) by the area (0.002581 m²) and record as dry specimen basis weight to the nearest 0.01 g/m². Calculate the bulk density of the specimen by dividing the specimen basis weight (g/m²) by the specimen thickness (mm), then dividing the quotient by 1000, and record as dry specimen density to the nearest 0.01 g/cm³. In like fashion, five replicate dry test specimens are prepared.

Wet test specimens are initially prepared in the exact manner as for the dry test specimen, followed by the addition of test fluid just prior to testing, as follows. First, the thickness and mass of the dry specimen is measured, as described herein, and recorded as initial thickness to the nearest 0.01 mm and initial mass to the nearest 0.001 g. Next, the dry specimen is fully submersed in the test fluid for 60 seconds. After 60 seconds elapse, the specimen is removed from the test fluid and oriented vertically for 30 seconds to allow any excess fluid to drip off. Now the thickness and mass of the wet specimen are measured, as described herein, and recorded as wet specimen caliper to the nearest 0.01 mm and wet specimen mass to the nearest 0.001 g. If desired, the mass of test fluid in the test specimen is calculated by subtracting the initial mass (g) from the wet specimen mass (g) and recording as test specimen fluid amount to the nearest 0.001 g. After the wet test specimen is removed from the test fluid, it must be tested within 10 minutes. In like fashion, five replicate wet test specimens are prepared.

Program the universal test frame for a flexural bend test, to move the crosshead such that the top fixture moves down with respect to the lower fixture at a rate of 1.0 mm/sec until the upper bar touches the top surface of the specimen with a nominal force of 0.02 N, then continue for an additional 12 mm. The crosshead is then immediately returned to the original gage at a rate of 1.0 mm/s. Force (N) and displacement (mm) data are continuously collected at 100 Hz throughout the test.

Load a dry test specimen such that it spans the two lower bars and is centered under the upper bar, with its sides parallel to the bars. For MD bending, the MD direction of the test specimen is perpendicular to the length of the 3 bars. Start the test and continuously collect force and displacement data.

Construct a graph of force (N) versus displacement (mm). From the graph, determine the maximum peak force and record as dry MD peak load to the nearest 0.01 N. Now calculate the maximum slope of the curve between initial force and maximum force (during the loading portion of the curve) and record to the nearest 0.1 unit. Calculate the modulus as follows, and record as dry MD modulus to the nearest 0.001 N/mm².

CD or MD Dry or Wet Bending Modulus $(N/mm^2)=$
(Slope×(Span³))/(4×specimen width×(specimen caliper³))

Calculate bending stiffness as follows, and record as dry MD bending stiffness to the nearest 0.1 N mm².

CD or MD Dry or Wet Bending Stiffness (N mm²)
=Modulus×Moment of Inertia where Moment of Inertia (mm⁴)=(specimen width×(specimen caliper³))/12

In like fashion, the procedure is repeated for all five replicates of the dry test specimens. The arithmetic mean among the five replicate dry test specimens is calculated for each of the parameters and reported as Dry Specimen 'Caliper' to the nearest 0.01 mm, Dry Specimen Basis Weight to the nearest 0.01 g/m², Dry Specimen Density to the nearest 0.001 g/cm³, Dry CD or MD Peak Load to the nearest 0.01 N, Dry CD or MD Bending Modulus to the nearest 0.001 N/mm², and Dry CD or MD Bending Stiffness to the nearest N mm².

The overall procedure is now repeated for all five replicates of the wet test specimens, reporting results as Wet CD or MD Peak Load to the nearest 0.01 N, Wet CD or MD Bending Modulus to the nearest 0.001 N/mm², and Wet CD or MD Bending Stiffness to the nearest N mm².

Wet and Dry CD Ultra Sensitive 3 Point Bending Method

The CD (cross-direction) bending properties of a test sample are measured using an ultra sensitive 3 point bend test on a universal constant rate of extension test frame (a suitable instrument is the MTS Alliance using TestSuite Software, as available from MTS Systems Corp., Eden Prairie, MN, or equivalent) equipped with a load cell appropriate for the forces being measured. The test is executed on dry test specimens as well as wet test specimens. The intention of this method is to mimic deformation created in the x-y plane by a wearer of an absorbent article during normal use. All testing is performed in a room controlled at 23° C.±3° C. and 50%±2% relative humidity.

The ultra sensitive 3 point bend method is designed to maximize the force signal to noise ratio when testing materials with very low bending forces. The force signal is maximized by using a high sensitivity load cell (e.g., 5N), using a small span (load is proportional to the span cubed) and using a wide specimen width (total measured load is directly proportional to width). The fixture is designed such that the bending measurement is performed in tension, allowing the fixture mass to be kept to a minimum. Noise in the force signal is minimized by holding the load cell stationary to reduce mechanical vibration and inertial effect and by making the mass of the fixture attached to the load cell as low as possible.

Figure 11A:
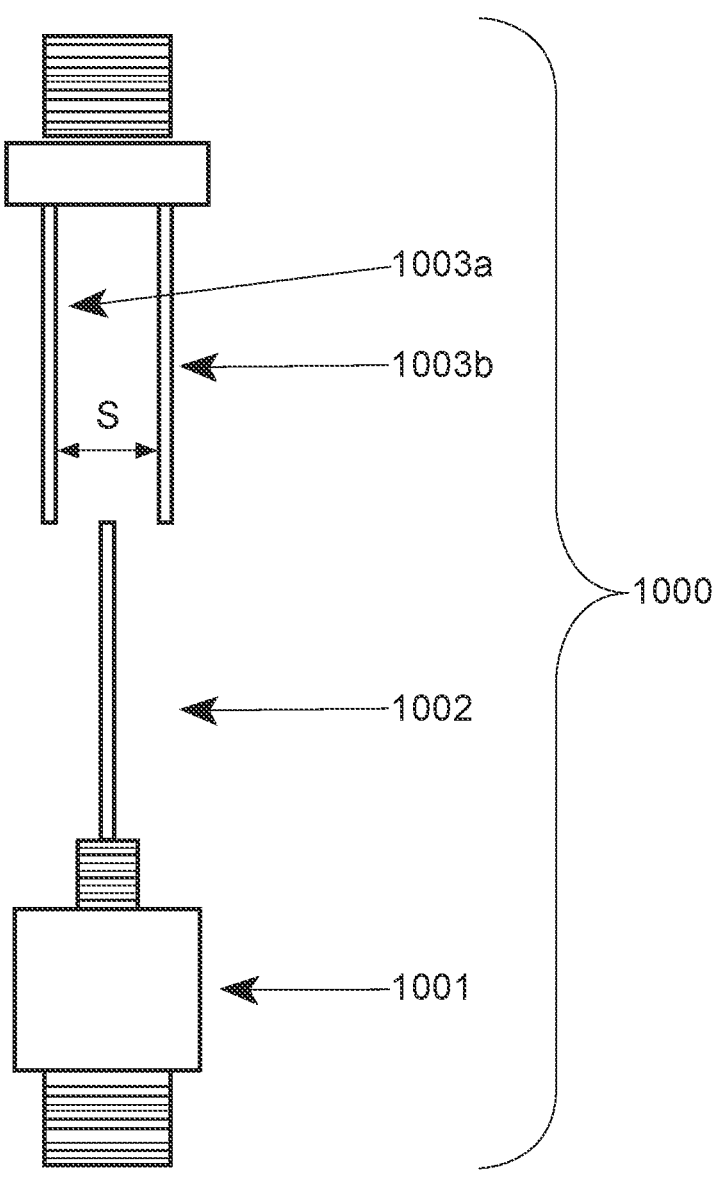
FIGS. 11A-C are a test method arrangement for the Wet and Dry CD Ultra Sensitive 3 Point Bending Method.
Figure 11B:
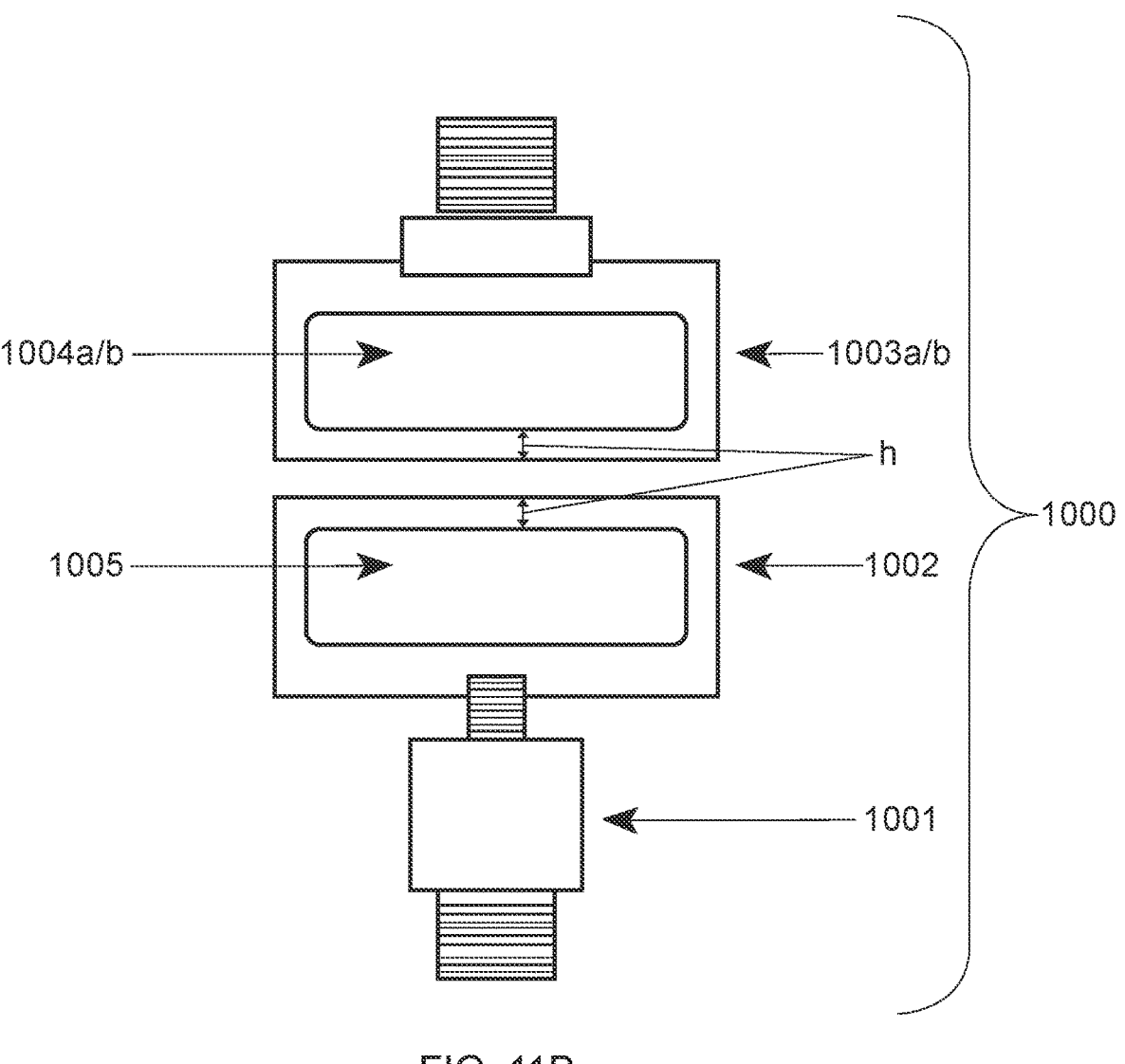
Figure 11C:
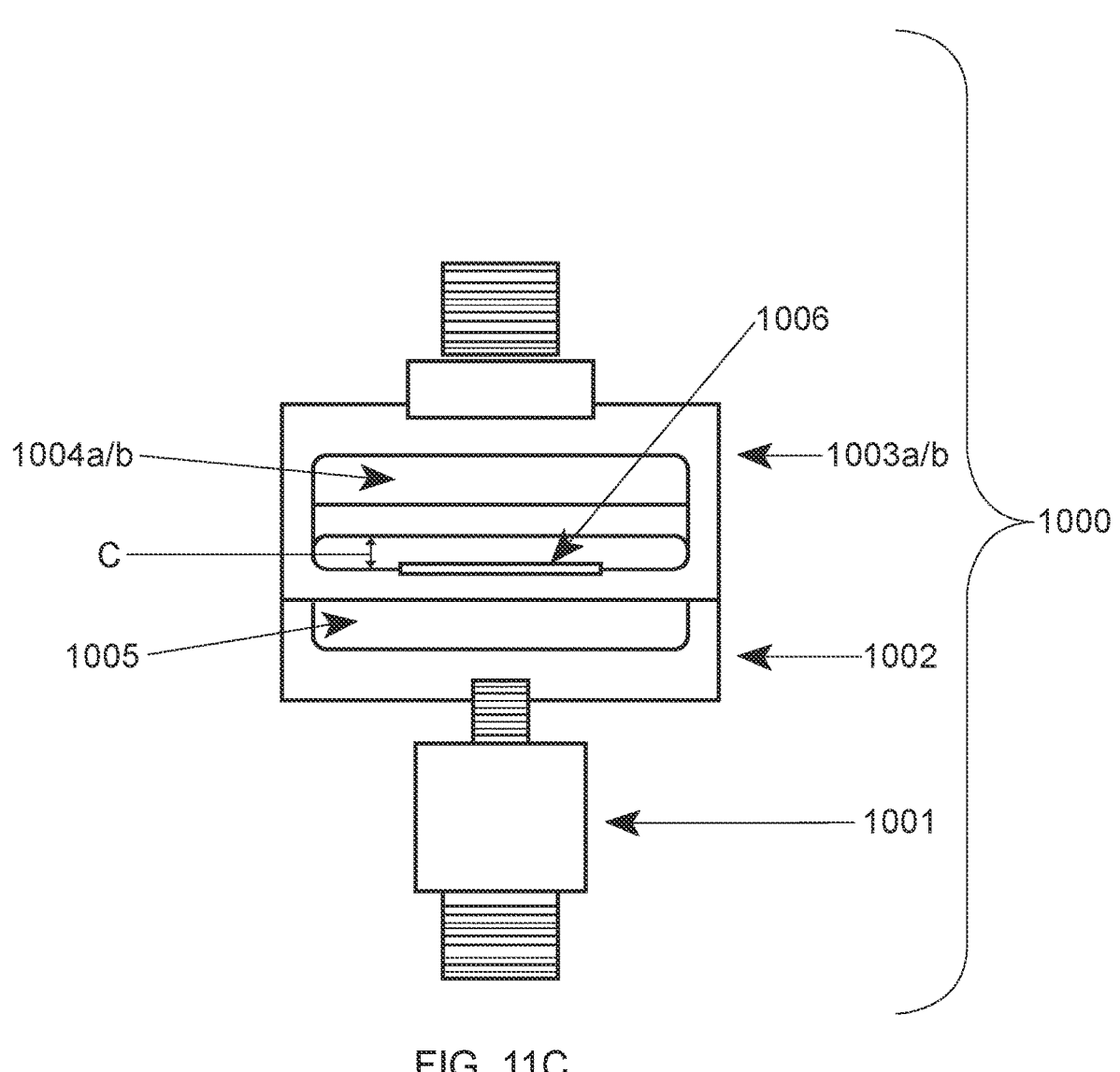

Referring to FIGS. 11A-11C, the load cell 1001 is mounted on the stationary crosshead of the universal test frame. The ultra sensitive fixture 1000 consists of three thin blades constructed of a lightweight, rigid material (such as aluminum, or equivalent). Each blade has a thickness of 1.0 mm, rounded edges and a length that is able to accommodate a bending width of 100 mm. Each of the blades has a cavity 1004a and 1004b (outside blades) and 1005 (central blade) cut out to create a height, h, of 5 mm of blade material along their horizontal edges. The two outside blades 1003a and 1003b are mounted horizontally to the moveable crosshead of the universal test frame, aligned parallel to each other, with their horizontal edges vertically aligned. The span, S, between the two outside blades 1003a and 1003b is 5 mm±0.1 mm (inside edge to inside edge). The central blade 1002 is mounted to the load cell on the stationary crosshead of the universal test frame. When in place, the central blade 1002 is parallel to the two outside blades 1003a and 1003b and centered at the midpoint between the outside blades 1003a and 1003b. The blade fixtures include integral adapters appropriate to fit the respective positions on the universal test frame and lock into position such that the horizontal edges of the blades are orthogonal to the motion of the crossbeam of the universal test frame.

The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved.

Samples are conditioned at 23° C.±3° C. and 50%±2% relative humidity two hours prior to testing. Dry test specimens are taken from an area of the sample that is free from any seams and residua of folds or wrinkles. The dry specimens are prepared for CD bending (i.e., bending normal to the lateral axis of the sample) by cutting them to a width of 50.0 mm along the CD (cross direction; parallel to the lateral axis of the sample) and a length of 100.0 mm along the MD (machine direction; parallel to the longitudinal axis of the sample), maintaining their orientation after they are cut and marking the body-facing surface (or the surface intended to face the body of a finished article). In like fashion, five replicate dry test specimens are prepared.

Wet test specimens are initially prepared in the exact manner as for the dry test specimen, followed by the addition of test fluid just prior to testing, as follows. The dry specimen is fully submersed in the test fluid for 60 seconds. After 60 seconds elapse, the specimen is removed from the test fluid and oriented vertically for 30 seconds to allow any excess fluid to drip off. After the wet test specimen is removed from the test fluid, it must be tested within 10 minutes. In like fashion, five replicate wet test specimens are prepared.

The universal test frame is programmed such that the moveable crosshead is set to move in a direction opposite of the stationary crosshead at a rate of 1.0 mm/s. Crosshead movement begins with the specimen 1006 lying flat and undeflected on the outer blades 1003a and 1003b, continues with the inner horizontal edge of cavity 1005 in the central blade 1002 coming into contact with the top surface of the specimen 1006, and further continues for an additional 4 mm of crosshead movement. The crosshead stops at 4 mm and then immediately returns to zero at a speed of 1.0 mm/s. Force (N) and displacement (mm) are collected at 50 Hz throughout.

Prior to loading the test specimen 1006, the outside blades 1003a and 1003b are moved towards and then past central blade 1002 until there is approximately a 3 mm clearance, C, between the inner horizontal edges of cavities 1004a and 1004b in the outside blades 1003a and 1003b and the inner horizontal edge of cavity 1005 in the central blade 1002 (see FIG. 11C). The specimen 1006 is placed within clearance C such that it spans the inner horizontal edges of cavities 1004a and 1004b in the outside blades 1003a and 1003b, oriented such that the MD (short side) of the specimen is perpendicular to the horizontal edges of the blades and the body-facing surface of the specimen is facing up. Center the specimen 1006 between the outside blades 1003a and 1003b. Slowly move the outside blades 1003a and 1003b in a direction opposite of the stationary crosshead until the inner horizontal edge of cavity 1005 in the central blade 1002 touches the top surface of the specimen 1006. Start the test and continuously collect force and displacement data.

Force (N) is plotted versus displacement (mm). The maximum peak force is recorded to the nearest 0.001 N. The area under the curve from load onset up to the maximum peak force is calculated and recorded as bending energy to the nearest 0.001 N–mm. The recovery energy is calculated as the area under the curve where the force is unloaded from the maximum peak to 0.0 N and recorded as recovery energy to the nearest 0.001 N–mm. In like fashion, repeat the entire test sequence for a total of five dry test specimens and five wet test specimens.

For each test specimen type (dry and wet), the arithmetic mean of the maximum peak force among like specimens is calculated to the nearest 0.001 N and recorded as Dry Peak Load and Wet Peak load, respectively. For each test specimen type (dry and wet), the arithmetic mean of bending energy among like specimens is calculated to the nearest 0.001 N–mm and reported as Dry Bending Energy and Wet Bending Energy, respectively. For each test specimen type (dry and wet), the arithmetic mean of recovery energy among like specimens is calculated to the nearest 0.001 N–mm and reported as Dry Recovery Energy and Wet Recovery Energy, respectively.

Wet and Dry Bunched Compression Method

The bunched compression test method measures the force versus displacement behavior across five cycles of load application ("compression") and load removal ("recovery") of an absorbent article test sample that has been intentionally "bunched", using a universal constant rate of extension test frame (a suitable instrument is the MTS Alliance using TestSuite software, as available from MTS Systems Corp., Eden Prairie, MN, or equivalent) equipped with a load cell for which the forces measured are within 1% to 99% of the limit of the cell. The test is executed on dry test specimens as well as wet test specimens that are dosed with a specified amount of test fluid. The intention of this method is to mimic the deformation created in the z-plane of the crotch region of an absorbent article, or components thereof, as it is worn by the wearer during sit-stand movements. All testing is performed in a room controlled at 23° C.±3° C. and 50%±2% relative humidity.

Figure 12:
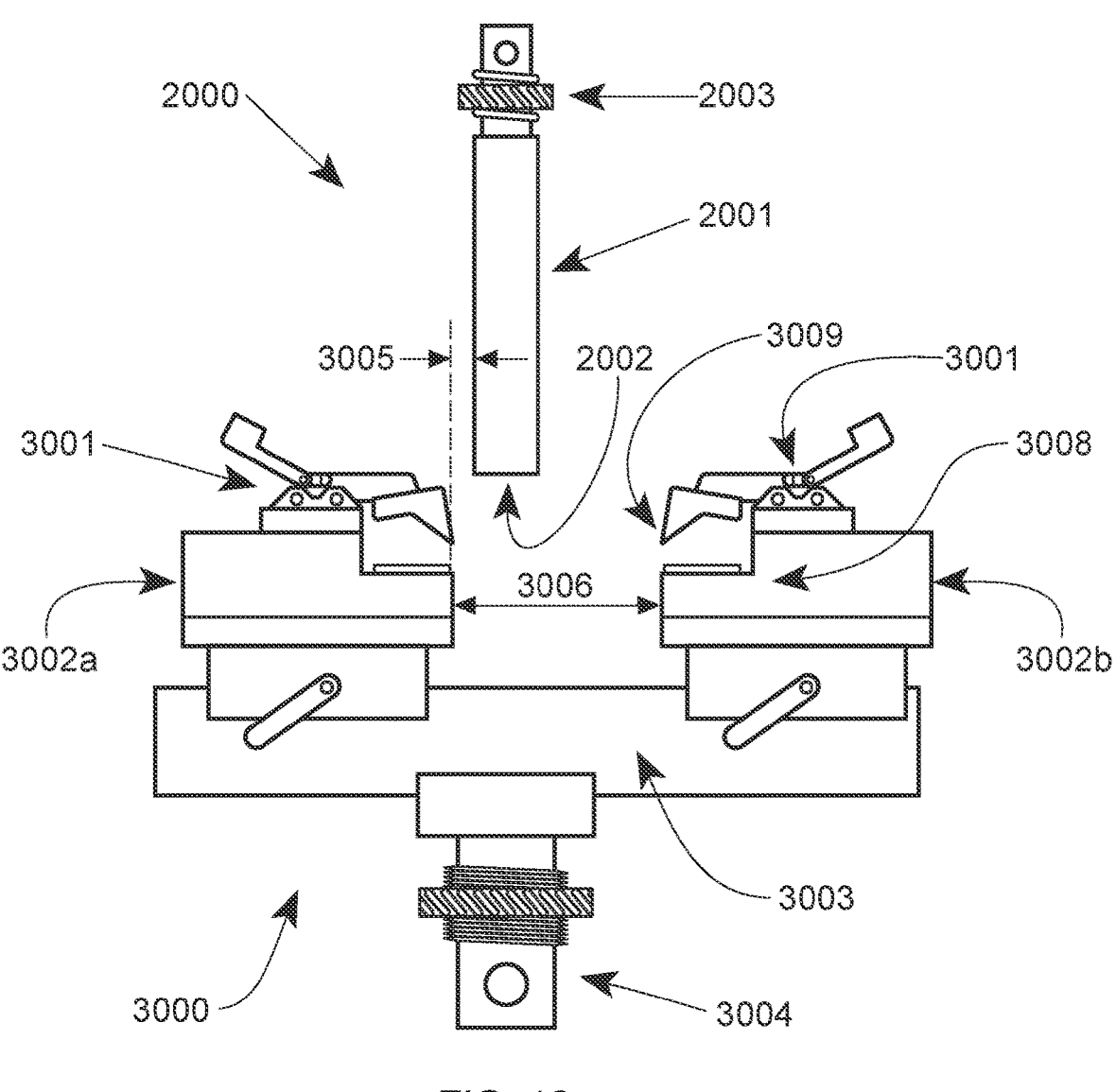
FIGS. 12, 13A, and 13B are the test method arrangement for the Wet and Dry Bunched Compression Test.
Figure 13A:
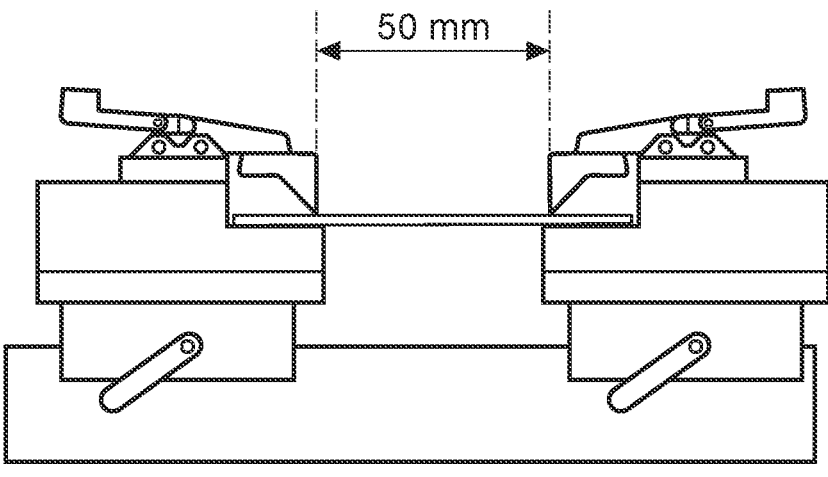
Figure 13B:
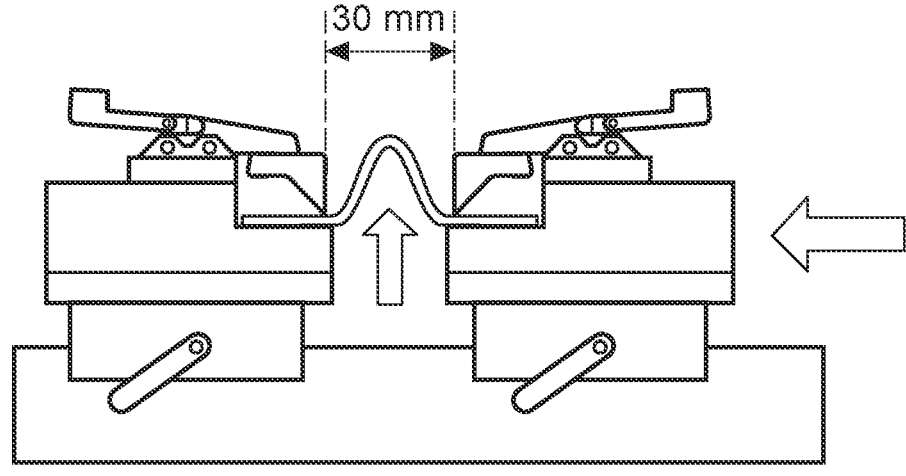

The test apparatus is depicted in FIGS. 12-13B. The bottom stationary fixture 3000 consists of two matching sample clamps 3001 each 100 mm wide, each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Test samples are conditioned at 23° C.±3° C. and 50%±2% relative humidity for at least 2 hours before testing. Prepare the test specimen as follows. When testing an intact absorbent article, remove the release paper from any panty fastening adhesive on the garment facing side of the article, if present. Lightly apply talc powder to the adhesive to mitigate any tackiness. If there are cuffs, excise them with scissors so as not to disturb the topsheet or any other underlying layers of the article. Place the article, body facing surface up, on a benchtop. On the article, mark the intersection of the longitudinal midline and the lateral midline. Using a rectangular cutting die or equivalent cutting means, cut a specimen 100 mm in the longitudinal direction by 80 mm in the lateral direction, centered at the intersection of the midlines. When testing a material layer or layered components from an absorbent article, place the material layer or layered components on a benchtop and orient as it would be integrated into a finished article, i.e., identify the body facing surface and the lateral and longitudinal axis. Using a rectangular cutting die, or equivalent cutting means, cut a specimen 100 mm in the longitudinal direction by 80 mm in the lateral direction, centered at the intersection of the midlines. Measure the mass of the specimen and record to the nearest 0.001 grams. Calculate the basis weight of the specimen by dividing the mass (g) by the area (0.008 m$^2$) and record as basis weight to the nearest 1 g/m$^2$.

The specimen can be analyzed both wet and dry. The dry specimen requires no further preparation. The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved. The wet specimen is dosed with total of 7 ml of the test solution as detailed below The liquid dose is added using a calibrated Eppendorf-type pipettor, spreading the fluid over the complete body facing surface of the specimen within a period of approximately 3 sec. The wet specimen is tested 10.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 50 Hz during all compression/decompression cycles.

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps 3001. Referring to FIG. 13A, place the dry specimen with its longitudinal edges (i.e., the 100 mm long edges) within the clamps. With the dry specimen laterally centered, securely fasten both edges in the clamps. Referring to FIG. 13B, move the right platform 3002b toward the stationary platform 3002a a distance of 20 mm so that a separation of 30.0 mm between the left and right clamps is achieved. Allow the dry specimen to bow upward as the movable platform is positioned. Now manually lower the probe 2001 until the bottom surface is approximately 1 cm above the top of the bowed specimen.

Figure 14A:
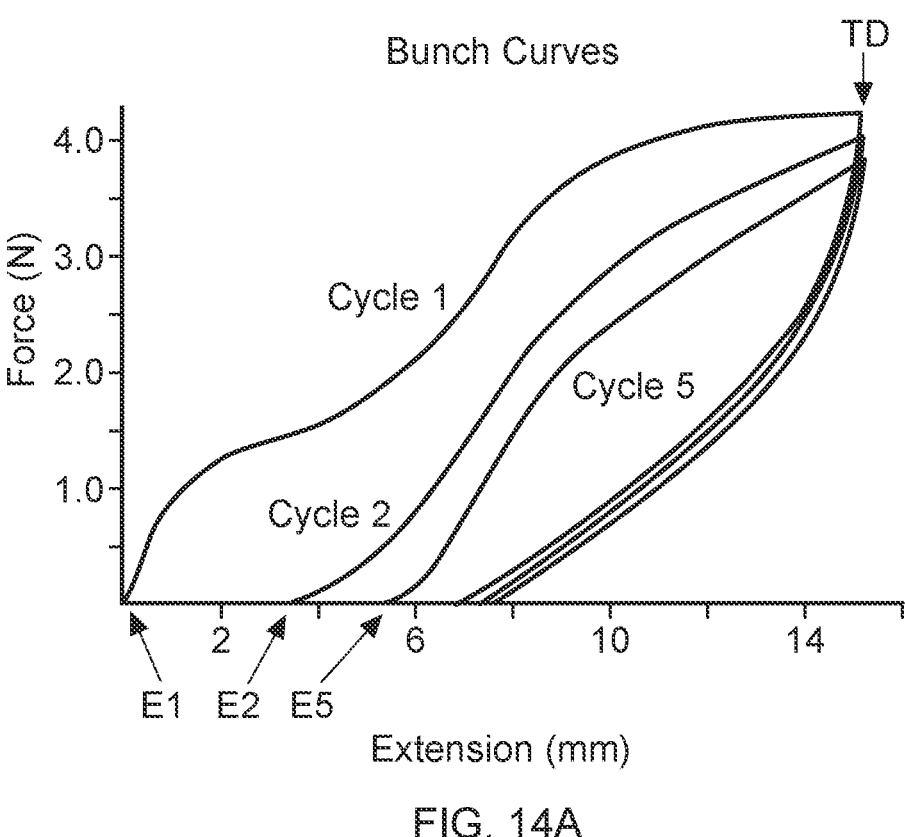
FIGS. 14A and 14B are illustrative graphs of Bunch Curves resulting from the Wet and Dry Bunched Compression Test. The graphs in FIGS. 14A and 14B are shown to illustrate how the calculations in the method may be performed and do not represent the data described herein.
Figure 14B:
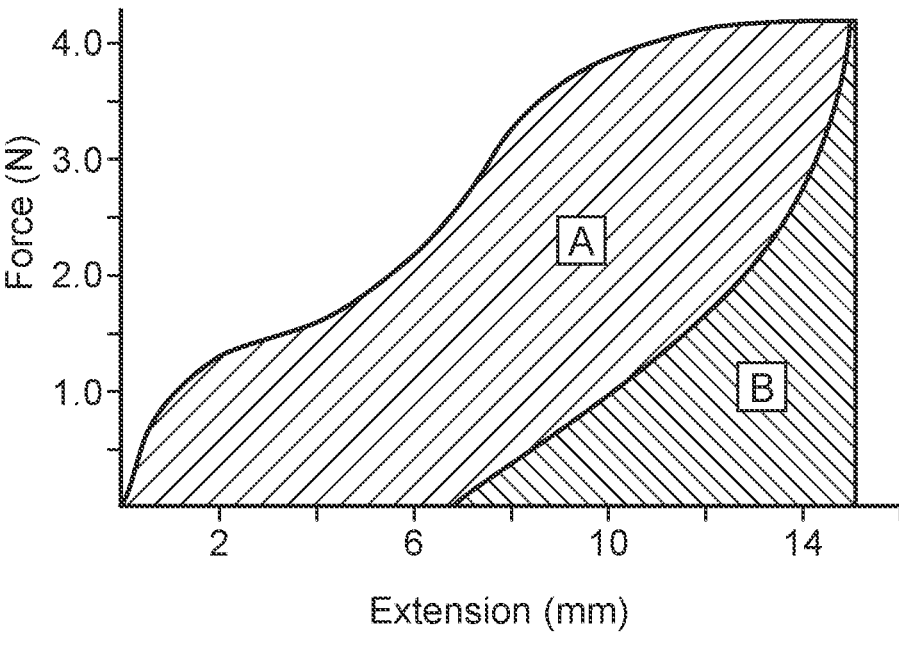

Start the test and continuously collect force (N) versus displacement (mm) data for all five cycles. Construct a graph of force (N) versus displacement (mm) separately for all cycles. A representative curve is shown in FIG. 14A. From the curve, determine the Dry Maximum Compression Force for each Cycle to the nearest 0.01 N, then multiply by 101.97 and record to the nearest 1 gram-force. Calculate the Dry % Recovery between the First and Second cycle as (TD–E2)/(TD–E1)*100 where TD is the total displacement and E2 is the extension on the second compression curve that exceeds 0.02 N, and record to the nearest 0.01%. In like fashion calculate the Dry % Recovery between the First Cycle and other cycles as (TD–E1)/(TD–E1)*100 and record to the nearest 0.01%. Referring to FIG. 14B, calculate the Dry Energy of Compression for Cycle 1 as the area under the compression curve (i.e., area A+B) and record to the nearest 0.1 N–mm. Calculate the Dry Energy Loss from Cycle 1 as the area between the compression and decompression curves (i.e., Area A) and record to the nearest 0.1 N–mm. Calculate the Dry Energy of Recovery for Cycle 1 as the area under the decompression curve (i.e., Area B) and report to the nearest 0.1 N–mm. In like fashion calculate the Dry Energy of Compression (N–mm), Dry Energy Loss (N–mm) and Dry Energy of Recovery (N–mm) for each of the other cycles and record to the nearest 0.1 N–mm. In like fashion, analyze a total of five replicate dry test specimens and report the arithmetic mean among the five dry replicates for each parameter as previously described, including basis weight.

The overall procedure is now repeated for a total of five replicate wet test specimens, reporting results for each of the five cycles as the arithmetic mean among the five wet replicates for Wet Maximum Compression Force to the nearest 1 gram-force for each cycle, Wet Energy of Compression to the nearest 0.1 N–mm for each cycle, Wet Energy Loss to the nearest 0.1 N–mm for each cycle, Wet Energy of Recovery to the nearest 0.1 N–mm for each cycle and Wet % recovery for each cycle. Of particular importance is the 5$^{th}$ cycle wet energy of recovery and 5$^{th}$ cycle wet % recovery properties from this test method.

CD Cyclic Elongation to 3% Strain

The cyclic tensile and recovery response of absorbent article specimens are measured for ten cycles of load application ("elongation") and load removal ("recovery") using a universal constant rate of extension test frame. The test specimen is cycled ten times to 3% engineering strain, then back to zero engineering strain. For each cycle, stiffness, peak load, normalized energy to peak, normalized recovery energy, strain at start of cycle, and strain at end of cycle (i.e., "permanent strain") are calculated and reported. The intention of this method is to understand the ability of samples to stretch in the x-y plane as a result of bodily forces, and then recover to their original state. All measurements are performed in a laboratory maintained at 23° C.±2° C. and 50%±2% relative humidity and test specimens are conditioned in this environment for at least 2 hours prior to testing.

A suitable universal constant rate of extension test frame is the MTS Alliance interfaced to a computer running TestSuite control software (available from MTS Systems Corp, Eden Prairie, MN), or equivalent. The universal test frame is equipped with a load cell for which forces measured are within 1% to 99% of the limit of the cell. The fixtures used to grip the test specimen are lightweight (<80 grams), vise action clamps with knife or serrated edge grip faces that are at least 40 mm wide. The fixtures are installed on the universal test frame and mounted such that they are horizontally and vertically aligned with one another.

The test specimen is prepared as follows. Obtain the test material by excising it from an absorbent article, if necessary. When excising the test material, do not impart any contamination or distortion to the material layer during the process. The test specimen is cut from an area on the test material that is free of any residual of folds or wrinkles. The test specimen is as long as the lateral length of the article (parallel to the lateral axis of the article, or the intended lateral axis of the article). When excising specimens from absorbent articles of different sizes and widths, the total specimen length ($L_{total}$) may vary from product to product, thus the results will be normalized to compensate for this variation. The test specimen has a width of 25.4 mm wide (parallel to the longitudinal axis, or intended longitudinal axis of the article). Specimen width (w)=25.4 mm. Measure and record the total specimen length ($L_{total}$) to the nearest 0.1 mm. In like fashion, five replicate test specimens are prepared.

Measure the thickness (t) of the test specimen using a manually-operated micrometer equipped with a pressure foot capable of exerting a steady pressure of 0.1 psi±0.01 psi. The manually-operated micrometer is a dead-weight type instrument with readings accurate to 0.01 mm A suitable instrument is Mitutoyo Series 543 ID-C Digimatic, available from VWR International, or equivalent. The pressure foot is a flat circular moveable face with a diameter no greater than 25.4 mm. The test specimen is supported by a horizontal flat reference platform that is larger than and parallel to the surface of the pressure foot. Zero the micrometer against the horizontal flat reference platform. Place the test specimen onto the platform, centered beneath the pressure foot. The pressure foot is lowered by hand with a descent rate of 3±1 mm/s until the full weight of the pressure is exerted onto the specimen. After 5 seconds elapse, the thickness is recorded as specimen thickness (t) to the nearest 0.01 mm.

Prepare the universal test frame as follows. Set the initial grip to grip separation distance to a nominal gage length ($L_{nominal}$) that is shorter than the total specimen length and such that the specimen can be gripped securely at both ends (i.e., $L_{nominal} < L_{total}$) Then zero the crosshead. Program the test frame to move the grips closer together by an intentional slack of 1 mm to ensure no pretension force exists on the test specimen at the onset of the test. (During this motion, the specimen will become slack between the tensile grips.) Next, the grips will move apart at a slack speed of 1 mm/s until the slack preload of 0.05 N is exceeded. At this point, the following are true. 1) The crosshead position signal (mm) is defined as the specimen slack ($L_{slack}$). 2) The initial specimen gage length ($L_0$) is calculated as the nominal gage length plus the slack $L_0 = L_{nominal} + L_{slack}$, where units are in millimeters. 3) The crosshead extension ($\Delta L$) is set to zero (0.0 mm). 4) The crosshead displacement (mm) is set To zero (0.0 mm). At this position the engineering strain is zero, 0.0. Engineering strain is calculated as the change in length ($\Delta L$) divided by the initial length ($L_0$). Engineering strain=$\Delta L/L_0$. For one test cycle, the grips move apart at the initial speed of 1 mm/s until the engineering strain endpoint of 0.03 mm/mm is exceeded, immediately followed by the grips moving toward each other at the initial speed of 1 mm/s until the crosshead signal becomes less than the crosshead return position of 0 mm. The test cycle is repeated until a total of 10 cycles is complete.

The test is executed by inserting the test specimen into the grips such that the long axis of the specimen is parallel and centered with the motion of the crosshead. Start the test and continuously collect time, force and displacement data at a data acquisition rate of 100 Hz.

Construct a graph of load (N) versus displacement for all ten cycles. For each cycle, perform the following. Record peak load to the nearest 0.01 N. Calculate the energy to peak ($E_{peak}$) as the area under the load versus displacement curve from the cycle start to the strain endpoint of mm/mm (during the loading portion of the cycle) and record to the nearest 0.01 N*mm. Calculate the return energy ($E_{return}$) as the area under the load versus displacement curve from the strain endpoint of 0.03 mm/mm to the crosshead return of 0 mm (during the unloading portion of the cycle) and record as recovery energy to the nearest 0.01 N*mm. Calculate the normalized energy to peak ($NE_{peak}$) as the energy to peak divided by the initial length, where $NE_{peak}=E_{peak}/L_0$, and record to the nearest 0.01 mN. Calculate the normalized return energy ($NE_{return}$) as the return energy divided by the initial length ($NE_{return}=E_{return}/L_0$), and record to the nearest 0.01 mN. Units of $NE_{peak}$ and $NE_{return}$ are milliNewtons (mN).

Now construct a graph of engineering stress ($\sigma$) versus engineering strain for all ten cycles, and for each cycle perform the following. Engineering stress, in units of $N/mm^2$, is the load divided by the cross sectional area of the specimen, where the cross sectional area is the specimen width (w) multiplied by the thickness (t), $\sigma=Load/(w*t)$. Determine the modulus, or slope of the stress versus strain curve for a line between the point that occurs at the minimum force and the point that occurs at the maximum force (during the loading portion of the cycle) and record as modulus to the nearest 0.01 N/mm. Calculate stiffness by multiplying the modulus by the specimen thickness and record as tensile stiffness to the nearest 0.01 N/mm. The strain of the test specimen at the beginning of the cycle is defined by the strain when the slack preload of 0.05 N is exceeded for that cycle (during the loading portion of the cycle), and is recorded as cycle initial strain to the nearest 0.01 mm/mm. The strain of the test specimen at the end of the cycle is defined by the strain when the load becomes less than the preload of 0.05 N for that cycle (during the unloading portion of the cycle), and is recorded as permanent strain to the nearest 0.01 mm/mm. In like fashion, the overall procedure is now repeated for all five replicates.

The arithmetic mean among the five replicate test specimens is calculated for each of the parameters, for each of the ten cycles, and reported as Peak Load to the nearest 0.01 N, Normalized Energy to Peak to the nearest 0.01 mN, Normalized Recovery Energy to the nearest 0.01 mN, Tensile Stiffness to the nearest 0.01 N/mm, Cycle Initial Strain to the nearest 0.01 mm/mm, and Permanent Strain to the nearest 0.01 mm/mm.

Structural Bond Sites Pattern Spacing and Area Measurement Method

The spacing between the discreet structural bond sites that are used to create a quilt-like pattern on absorbent article samples, and the overall area taken up by the sum of those elements in a specified region of the sample are measured on images of the absorbent article sample acquired using a flatbed scanner. The scanner is capable of scanning in reflectance mode at a resolution of 2400 dpi and 8 bit grayscale. A suitable scanner is an Epson Perfection V750 Pro from Epson America Inc., Long Beach CA, or equivalent. The scanner is interfaced with a computer running an image analysis program. A suitable program is ImageJ v. 1.52, National Institute of Health, USA, or equivalent. The sample images are distance calibrated against an acquired image of a ruler certified by NIST. To enable maximum contrast, the specimen is backed with an opaque, black background of uniform color prior to acquiring the image. All testing is performed in a conditioned room maintained at about 23±2° C. and about 50±2% relative humidity.

The test sample is prepared as follows. Remove the absorbent article from any wrapper present. If the article is folded, gently unfold it and smooth out any wrinkles. If wings are present, extend them but leave the release paper intact. The test samples are conditioned at about 23° C.±2° C. and about 50%±2% relative humidity for 2 hours prior to testing.

Images are obtained as follows. The ruler is placed on the scanner bed such that it is oriented parallel to the sides of the scanner glass. An image of the ruler (the calibration image) is acquired in reflectance mode at a resolution of 2400 dpi (approximately 94 pixels per mm) and in 8-bit grayscale. The calibration image is saved as an uncompressed TIFF format file. After obtaining the calibration image, the ruler is removed from the scanner glass and the test sample is scanned under the same scanning conditions as follows. Place the test sample onto the center of the scanner glass and secure, if necessary, such that it lies flat with the body-facing surface of the sample facing the scanner's glass surface. The sample is oriented in such a way that the entire sample is within the glass surface. The black background is placed on top of the specimen, the scanner lid is closed, and a scanned image of the entire sample is acquired with the same settings as used for the calibration image. The sample image is saved as an uncompressed TIFF format file.

The sample image is analyzed as follows. Open the calibration image file in the image analysis program, and calibrate the image resolution using the imaged ruler to determine the number of pixels per millimeter. Now open the sample image in the image analysis program, and set the distance scale using the image resolution determined from the calibration image. Now visually inspect the pattern of emboss elements present on the sample in the image and identify the zones of the pattern that are to be analyzed. For example the absorbent article can be divided into three equal lengths zones in the machine direction such as the front one third zone, zone 1, the central one third zone, zone 2 and the end one third zone, zone 3 as example. Use the image analysis tools to draw a shape along the outer perimeter of the first discreet zone to be analyzed. Measure the area of this first zone and record as Zone 1 Total Area to the nearest 0.01 mm$^2$. Now measure the area of each individual, discreet emboss element that lies inside of the zone 1 perimeter as follows. Draw a minimum bounding circle around an individual emboss element such that no portion of the emboss element lies outside of the bounding circle. Now measure the area of the bounding circle for that emboss element and record the emboss element area to the nearest 0.01 mm$^2$. In like fashion, measure the area of every emboss element, including portions of emboss elements, that lie inside zone 1 and record each to the nearest 0.01 mm$^2$. Now sum the areas of all of the emboss elements inside of zone 1 and record as Zone 1 Total Emboss Element Area to the nearest 0.01 mm$^2$. Divide the Zone 1 Total Emboss Element Area by the Zone 1 Total Area then multiply by 100 and record as Zone 1% Total Area Represented by Emboss Elements. The spacing between each discreet emboss element inside of zone 1 is measured as follows. Measure the distance from the center of the minimum bounding circle drawn around a discreet emboss element inside of zone 1, as described herein, to the center of the minimum bounding circle drawn around the nearest neighboring discreet emboss element inside of zone 1, and record this distance as emboss spacing to the nearest 0.01 mm. In like fashion, repeat for all neighboring emboss elements inside of zone 1, and record each distance to the nearest 0.01 mm. Now calculate the arithmetic mean among all measured emboss spacings measured between nearest neighbors inside of zone 1, and record as Zone 1 Emboss Spacing to the nearest 0.01 mm.

In like fashion, the entire procedure is repeated for each additional zone containing emboss elements that is present on the test sample and label accordingly as Zone 2, Zone 3, etc.

Light Touch Rewet Method

Light Touch Rewet method is a quantitative measure of the mass of liquid that emerges from an absorbent article test sample that has been dosed with a specified volume of Artificial Menstrual Fluid (AMF; as described herein) when a weight is applied for a specified length of time. All measurements are performed in a laboratory maintained at 23° C.±2° C. and 50%±2% relative humidity.

A syringe pump equipped with a disposable syringe is utilized to dose the test sample. A suitable pump is the Perfusor® Compact S (available from B. Braun), or equivalent, and must be able to accurately dispense the AMF at a rate of 42 ml/min. The disposable syringe is of ample volume (e.g., BD Plastipak 20 mL) and is connected to flexible tubing that has an inner diameter of ³⁄₁₆" (e.g., Original Perfusor® Line, available from Braun, or equivalent). The AMF is prepared, as described herein, and is brought to room temperature (23° C.±2° C.) prior to using for this test. Prior to the commencement of the measurement, the syringe is filled with AMF and the flexible tubing is primed with the liquid, and the dispensing rate (42 ml/min) and dosing volume (4.0 mL+0.05 mL) are verified according to the manufacturer's instructions. The flexible tubing is then mounted such that it is oriented vertically above the test sample, and the distance between the tip of the tubing and the surface of the test sample is 19 mm. To note, the AMF must be removed from the syringe and thoroughly mixed every 15 minutes.

The rewet weight assembly consists of an acrylic plate and a stainless steel weight. The acrylic plate has dimensions of 65 mm by 80 mm with a thickness of about 5 mm. The stainless steel weight along with the acrylic plate have a combined mass of 2 pounds (907.19 g), to impart a pressure of 0.25 psi beneath the surface of the acrylic plate.

For each test sample, five sheets of filter paper with dimensions of 4 inch by 4 inch are used as the rewet substrate. The filter paper is conditioned at 23° C.±2° C. and 50%±2% relative humidity for at least 2 hours prior to testing. A suitable filter paper has a basis weight of about 139 gsm, a thickness of about 700 microns with an absorption rate of about 1.7 seconds, and is available from Ahlstrom-Munksjo North America LLC, Alpharetta, GA VWR International as Ahlstrom grade 989, or equivalent.

Prepare the test sample as follows. The test samples are conditioned at 23° C.±2° C. and 50%±2% relative humidity for at least 2 hours prior to testing. Test samples are removed from all packaging using care not to press down or pull on the products while handling. Lay the test sample on a horizontally rigid flat surface and gently smooth out any folds. Determine the test location as follows. For symmetrical samples (i.e., the front of the sample is the same shape and size as the back of the sample when divided laterally along the midpoint of the longitudinal axis of the sample), the test location is the intersection of the midpoints of the longitudinal axis and lateral axis of the sample. For asymmetrical samples (i.e., the front of the sample is not the same shape and size as the back of the sample when divided laterally along the midpoint of the longitudinal axis of the sample), the test location is the intersection of the midpoint of the longitudinal axis of the sample and a lateral axis positioned at the midpoint of the sample's wings. A total of three test samples are prepared.

Place the test sample on a horizontally flat rigid surface, with the previously identified test location centered directly below the tip of the flexible tubing. Adjust the height of the tubing such that it is 19.0 mm above the surface of the test sample. Start the pump to dispense 4.0 mL+0.05 mL of AMF at a rate of 42 ml/min. As soon as the AMF has been fully dispensed, start a 10 minute timer. Now obtain the mass of 5 sheets of the filter paper and record as dry mass to the nearest grams. When 10 minutes have elapsed, place the five sheets of pre-weighed filter papers onto the test sample, centering the stack over the dosing location. Now place the acrylic plate centered over the top of the filter papers such that the long side of the plate is parallel with the longitudinal axis of the test sample. Now carefully lower the stainless steel weight centered over the acrylic plate and immediately start a 30 second timer. After 30 seconds have elapsed, gently remove the rewet weight and acrylic plate and set aside. Obtain the mass of the five sheets of filter paper and record as wet mass to the nearest 0.001 grams. Subtract the dry mass from the wet mass of the filter papers, and record as rewet to the nearest 0.001 grams. Wipe off any residual test liquid from the bottom face of the acrylic plate prior to testing the next sample. In like fashion, repeat for a total of three replicate test samples.

The arithmetic mean of the rewet among the three replicate test samples is calculated and reported as the 'Light Touch Rewet' to the nearest 0.001 g.

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity of the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1° C. and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, sterilized, available from American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5° C. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.02 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1° C.

Allow the temperature of the sheep blood and mucous component to come to 23° C.±1° C. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1° C. Any unused portion is discarded after testing is complete.

Flex Bond Channel Measurements

The flex bond embossment length, flex bond land area length between two adjacent flex bond embossments, the flex bond channel width, and the flex bond channel depth of the flex bond channel regions formed near the central portion of an absorbent article test sample are measured using optical profilometry to obtain the areal surface topography of the body facing side of the test sample. The flex bond embossment length, flex bond land area length between two adjacent embossments, and the flex bond channel width of the flex bond channel is measured at the base of the depressions, and the depth of the flex bond channel is measured relative to an adjacent, non-channeled region. Additionally, the bending resistance properties of prepared test specimens of the flex bond channel regions are measured on a universal constant rate of extension test frame. All testing is performed in a room controlled at 23° C.±3° C. and 50%±2% relative humidity, and test samples and specimens are conditioned in this environment for at least 2 hours prior to testing.

For the flex bond embossment length, length of the land area between flex bond embossments, channel width and channel depth methods, three-dimensional (3D) surface topography images of the body-facing side of the test sample are recorded using an optical 3D surface topography measurement system. A suitable optical 3D surface topography measurement system is the MikroCAD Premium instrument commercially available from LMI Technologies Inc., Vancouver, Canada, or equivalent. The system includes the following main components: a) a Digital Light Processing (DLP) projector with direct digital controlled micro-mirrors; b) a CCD camera with at least a 1600×1200 pixel resolution; c) projection optics adapted to a measuring area of at least 140 mm×105 mm; d) recording optics adapted to a measuring area of 140 mm×105 mm; e) a table tripod based on a small hard stone plate; f) a blue LED light source; g) a measuring, control, and evaluation computer running surface texture analysis software (a suitable software is MikroCAD software with MountainsMap® technology, or equivalent); and h) calibration plates for lateral (XY) and vertical (Z) calibration available from the vendor. The optical 3D surface topography measurement system measures the surface height of a sample using the digital micro-mirror pattern fringe projection technique. The result of the measurement is a 3D image of surface height (defined as the Z axis) versus displacement in the horizontal (XY) plane. The system has a field of view of 140×105 mm with an XY pixel resolution of approximately 85 microns. The height resolution is set to 0.5 micron/count, with a height range of +/−10 mm. Prior to testing, the instrument is calibrated according to manufacturer's specifications using the calibration plates for lateral (XY plane) and vertical (Z axis) available from the vendor.

Prepare the absorbent article test sample for surface topography measurements, and subsequent channel MD bending resistance measurements, as follows. Unfold the absorbent article if necessary but keep the protective covering over the panty fastening adhesive (i.e. wrapper or release paper) in place. Identify and label the front and rear of the article. Additionally, identify and label the left and right sides of the article, with respect to the wearer's left and right. If the article was previously folded, use scissors or an equivalent sharp cutting device to make a cut along the width of the article at a location that is about 1 cm inboard and parallel to the front fold line such that any residua of folded or creased material is removed and discarded from the front portion of the article. In like fashion, make a cut along the width of the article at a location that is about 1 cm inboard and parallel to the rear fold line to remove and discard any residua of folded or creased material from the rear portion of the article. After making the cuts, the remaining central portion of the absorbent article is retained as the test sample with a length of about 60 mm but not less than 40 mm. With the residua of folded material removed, the test sample will lie flat against a horizontal rigid surface. Now remove the protective covering from the panty fastening adhesive and apply a light dusting of talc powder to the adhesive to mitigate tackiness. In like fashion, prepare a total of five replicate test samples.

Acquire a 3D surface topography image of the test sample as follows. Transfer the test sample onto the MikroCAD (or equivalent) table beneath the camera. Orient the test sample such that the longitudinal axes of the left and right flex bond channel regions are perpendicular to the long axis (X axis) of the instrument's field of view. A 3D surface topography image of the test sample is collected following the instrument manufacturer's recommended measurement procedures, which may include focusing the measurement system and performing a brightness adjustment. No pre-filtering options are used. The collected height image file is saved to the evaluation computer running the surface texture analysis software.

The 3D surface topography image is opened in the surface texture analysis software. The following filtering procedure is then performed on the image: 1) removal of invalid points; 2) a 3×3 pixel median filter to remove noise; and 3) a 3×3 pixel mean filter to smooth the surface.

Figure 15:
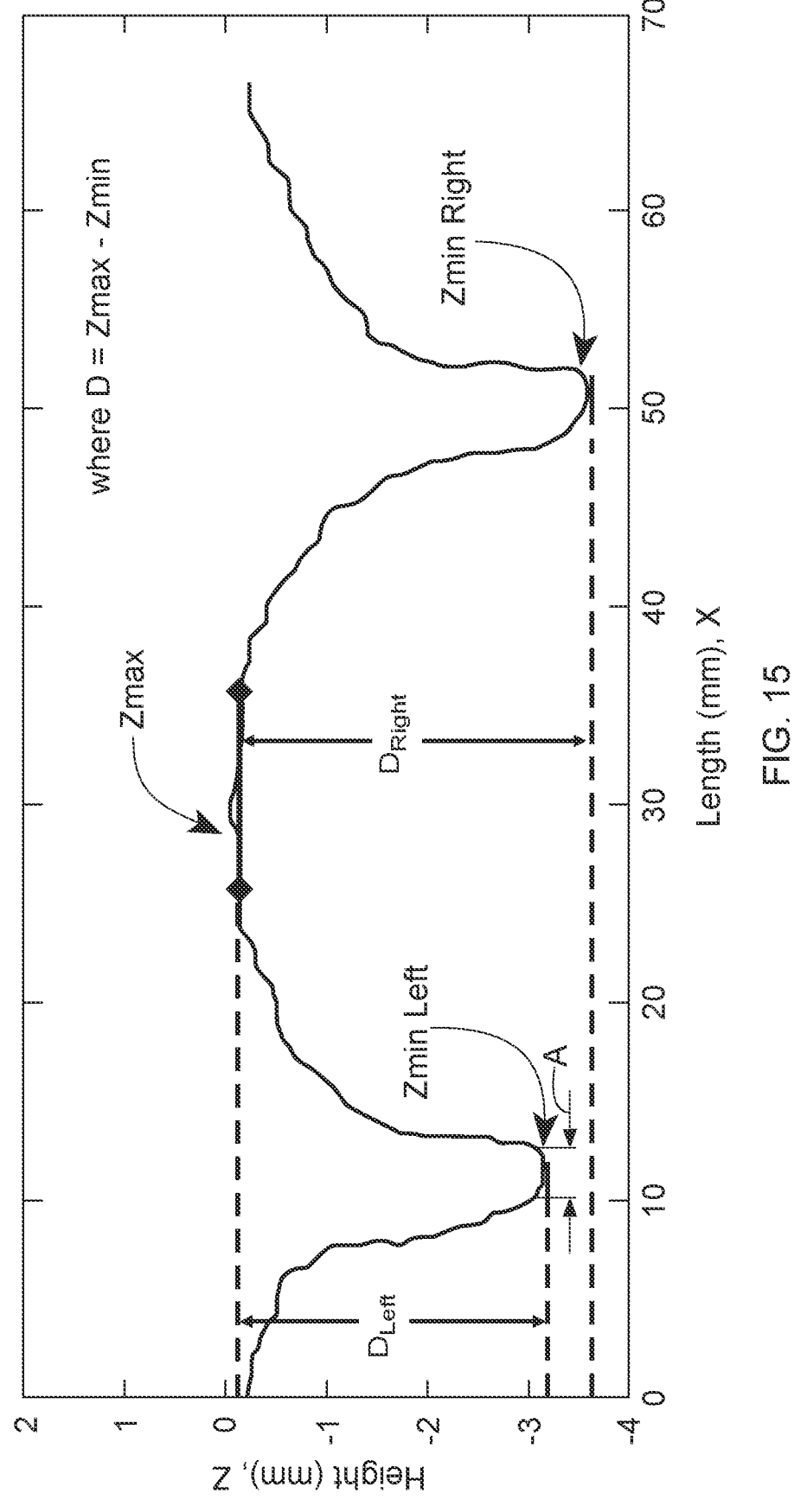
FIG. 15 is an illustrative graph of the channel depth width of the flex bond channel region relative to the non-channeled region resulting from the Flex Bond Channel Depth and Width Methods. The graph in FIG. 15 is shown to illustrate how the calculations in the method may be performed and do not represent the data described herein.

Flex Bond Embossment Length Method:

To measure the flex bond embossment length, "L", a two-dimensional (2D) line profile (a subsampling of the 3D surface image) is extracted from a location within one of the individual depressed regions within the flex bond channel regions that is perpendicular to the short side of the depression (i.e. the line traverses the longitudinal axis of the depression). This line profile extends across the entire length of the individual channel depression along its central longitudinal axis and includes non-depressed regions directly adjacent to both ends of the channel. One of skill in the art knows if the resulting line profile is not generally representative of the general contour of the flex bond channel region, owing to measurement noise or the presence of local wrinkling or a malformed channel (i.e. a channel that has a depth less than 1 mm as determined by the Flex Bond Channel Depth Method described herein), that another test location at a separate depressed region of the flex bond channel should be measured such that no such artifacts exist. Now create the height profile of the line (height (mm) versus line length (mm)). It will be obvious to one of skill in the art where the flex bond channel region (minimum Z value) and the non-channeled regions (maximum Z values adjacent to the channel) are located on the height profile, for example as depicted in FIG. 15. This line profile depicts an exemplary length of the depressed region within the flex bond channel. Determine the minimum height value (y axis) on the line profile. Now move along the line on the left side of the profile in the z-direction (y axis) from the minimum height value to a position that is 100 microns away from the minimum height value, and set a "left" marker on the line profile. In like fashion, move along the line on the right side of the profile in the z-direction (y axis) from the minimum height value to a position that is 100 microns away from the minimum height value, and set a "right" marker on the line profile. Measure the horizontal x distance between the left and right markers placed on the line profile and record as flex bond channel length to the nearest 0.1 mm. Now repeat the entire procedure until a total of five separate, individual depressed regions of the flex bond channels have been analyzed on the test sample. In like fashion, measure a total of five separate, individual depressed regions of the flex bond channels on each of the remaining four replicate test samples. Now calculate the arithmetic mean across all of the flex bond channel length values recorded across all five test sample replicates, and report as Flex Bond Embossment Length, "L", to the nearest 0.1 mm.

The five replicate test samples are retained and used for the subsequent flex bond land area length measurements.

Flex Bond Land Area Length Method:

To measure the length of the land area "S" between two individual, adjacent depressed regions (embossments) within a flex bond channel, a two-dimensional (2D) line profile (a subsampling of the 3D surface image) is extracted as follows. This line profile includes the entire lengths of two individual, adjacent channel depressions along their central longitudinal axes and additionally includes non-depressed regions directly adjacent to both the leading edge of the first depressed region and the trailing edge of the second, adjacent depressed region. One of skill in the art knows if the resulting line profile is not generally representative of the general contour of the flex bond channel region, owing to measurement noise or the presence of local wrinkling or a malformed channel (i.e. a channel that has a depth less than 1 mm as determined by the Flex Bond Channel Depth Method described herein), that another test location that includes a different set of two adjacent depressed regions of the flex bond channel should be measured such that no such artifacts exist. Now create the height profile of the line (height (mm) versus line length (mm)). It will be obvious to one of skill in the art where the flex bond channel regions (minimum Z values) and the non-channeled regions (maximum Z values adjacent to the channel) are located on the height profile, for example as depicted in FIG. 15. This line profile depicts the exemplary lengths of two, adjacent depressed regions within the flex bond channel as well as the length of the distance between them. The distance between the adjacent depressed regions is measured from the trailing end of the first depressed region to the leading end of the second depressed region as follows. Determine a first minimum height value (y axis) on the line profile within the first depressed region. Now move along the line profile in the z-direction to the right side of the first minimum height value (y axis) to a position that is 100 microns away from the first minimum height value, and set a "first" marker on the line profile. Now determine a second minimum height value (y axis) on the line profile within the second depressed region. Move along the line profile in the z-direction to the left side of the second minimum height value (y axis) to a position that is 100 microns away from the second minimum height value, and set a "second" marker on the line profile. Now measure the horizontal x distance between the first and second markers placed on the line profile and record as length of the flex bond land area, "S", to the nearest 0.1 mm. Now repeat the entire procedure until a total of five separate sets of adjacent pairs of depressed regions of the flex bond channels have been analyzed on the test sample. In like fashion, measure a total of five separate sets of adjacent pairs of depressed regions of the flex bond channels on each of the remaining four replicate test samples. Now calculate the arithmetic mean across all of the flex bond land area length values recorded across all five test sample replicates, and report as Flex Bond Land Area Length to the nearest 0.1 mm.

The five replicate test samples are retained and used for the subsequent flex bond channel width measurements.

Flex Bond Channel Width Method:

To measure the flex bond channel width, "A", a two-dimensional (2D) line profile (a subsampling of the 3D surface image) is extracted from a location within one of the individual depressed regions within the flex bond channel regions that is perpendicular to the long side of the depression (i.e. the line traverses the width of the depression). This line profile extends across the entire width of the individual channel depression along its central lateral axis and includes non-depressed regions directly adjacent to both sides of the channel. One of skill in the art knows if the resulting line profile is not generally representative of the general contour of the flex bond channel region, owing to measurement noise or the presence of local wrinkling or a malformed channel (i.e. a channel that has a depth less than 1 mm as determined by the Flex Bond Channel Depth Method described herein), that another test location at a separate depressed region of the flex bond channel should be measured such that no such artifacts exist. Now create the height profile of the line (height (mm) versus line length (mm)). It will be obvious to one of skill in the art where the flex bond channel region (minimum Z value) and the non-channeled regions (maximum Z values adjacent to the channel) are located on the height profile, for example as depicted in FIG. 15. This line profile depicts an exemplary width of the depressed region within the flex bond channel. Determine the minimum height value (y axis) on the line profile. Now move along the line on the left side of the profile in the z-direction (y axis) from the minimum height value to a position that is 200 microns away from the minimum height value, and set a "left" marker on the line profile. In like fashion, move along the line on the right side of the profile in the z-direction (y axis) from the minimum height value to a position that is 200 microns away from the minimum height value, and set a "right" marker on the line profile. Measure the horizontal x distance between the left and right markers placed on the line profile and record as flex bond channel width to the nearest 0.1 mm. Now repeat the entire procedure until a total of five separate, individual depressed regions of the flex bond channels have been analyzed on the test sample. In like fashion, measure a total of five separate, individual depressed regions of the flex bond channels on each of the remaining four replicate test samples. Now calculate the arithmetic mean across all the flex bond channel width values recorded for across all five test sample replicates, and report as Flex Bond Channel Width, "A", to the nearest 0.1 mm.

The five replicate test samples are retained and used for the subsequent flex bond channel depth measurements.

Flex Bond Channel Depth Method:

The test samples from the flex bond channel width method are further prepared for the channel depth measurement as follows. Draw a line that is roughly 35 mm long on the body facing surface of the test sample within each of the flex bond channel regions (left and right) to depict the location where the flex bond channel region depth will be measured and the test specimen for the bending resistance test will be subsequently taken. The left and right flex bond channel regions are those that have a longitudinal direction that is generally parallel to the longitudinal axis of the absorbent article. In like fashion, prepare the remaining four replicate test samples such that a total of ten flex bond channel regions (5 right and 5 left) can be analyzed. Numerically label each test sample (i.e. i-v) such that the test samples can be tracked throughout each subsequent measurement.

The thickness of the first test sample is measured at a test location defined as the non-channeled region of the test sample that lies between the left and right flex bond channel regions and excludes all portions of any flex bond channel region present. Ideally, the test location is at the center of the absorbent article (intersection of the lateral and longitudinal midpoints), and centered between the left and right flex bond channel regions. The thickness of the test sample is mechanically measured using a manually-operated micrometer equipped with a pressure foot capable of exerting a steady pressure of 0.1 psi±0.01 psi (0.69 kPa±0.07 kPa). The manually-operated micrometer is a dead-weight type instrument with readings accurate to 0.01 mm. A suitable instrument is Mitutoyo Series 543 ID-C Digimatic, available from VWR International, or equivalent. The pressure foot is a flat circular moveable face with a diameter of 25.4 mm. The test sample is supported by a horizontal flat reference platform that is larger than and parallel to the surface of the pressure foot. Zero the micrometer against the horizontal flat reference platform. Place the test sample onto the platform, with the test location centered beneath the pressure foot. Ensure that no portion of the pressure foot will make contact with any portion of any flex bond channel region present, and then lower the pressure foot by hand with a descent rate of 3±1 mm/s until the full pressure is exerted onto the sample. After 5 seconds elapse, the thickness is recorded as absorbent article thickness, Ti, to the nearest 0.01 mm. In like fashion, repeat the thickness measurement for all five replicate test samples, recording pad thickness to the nearest 0.01 mm for each (i.e. Ti-Tv). Calculate the arithmetic mean across all five replicates and report as Absorbent Article Thickness, T, to the nearest 0.01 mm.

Acquire a 3D surface topography image of the first test sample, i, as follows. Transfer the test sample onto the MikroCAD (or equivalent) table beneath the camera. Orient the test sample such that the longitudinal axes of the left and right flex bond channel regions are perpendicular to the long axis (X axis) of the instrument's field of view. A 3D surface topography image of the test sample is collected following the instrument manufacturer's recommended measurement procedures, which may include focusing the measurement system and performing a brightness adjustment. No prefiltering options are used. The collected height image file is saved to the evaluation computer running the surface texture analysis software.

The 3D surface topography image is opened in the surface texture analysis software. The following filtering procedure is then performed on the image: 1) removal of invalid points; 2) a 3×3 pixel median filter to remove noise; and 3) a 3×3 pixel mean filter to smooth the surface. A two-dimensional (2D) line profile (a subsampling of the 3D surface image) is extracted from a location that is perpendicular to the direction of the flex bond channel regions. This line profile extends across the entire width (left to right) of the test sample and intersects both the left and right flex bond channel regions on the test sample at 90 degrees. The line profile is drawn such that it intersects a portion of the channels where the 35 mm line was previously drawn during sample prep. One of skill in the art knows if the resulting line profile is not generally representative of the general contour of the flex bond channel regions, owing to measurement noise or the presence of local wrinkling or a malformed channel, that another test sample should be prepared and measured such that no such artifacts exist. Now create the height profile of the line (height (mm) versus line length (mm)). It will be obvious to one of skill in the art where the flex bond channel regions (minimum Z values) and the non-channeled region (maximum Z values between the channels) are located on the height profile, for example as depicted in FIG. 15. This line profile depicts an exemplary depth of the flex bond channel regions relative to the non-channeled region located adjacent to and between the flex bond channel regions present on the test sample. Export the line height profile raw data to .txt format.

The line height profile raw data is imported and processed in a spreadsheet program, such as Excel, or equivalent. Determine the Z minimum value for the flex bond channel region on the left side of test sample i, and record as $Zmin_{iL}$ to the nearest 0.1 mm. In like fashion, determine the Z minimum value for the flex bond channel region on the right side of test sample i, and record as $Zmin_{iR}$ to the nearest 0.1 mm. The height of the non-channeled region along the portion of the line that lies between the left and right flex bond channel regions is $Zmax_i$. $Zmax_i$ is the calculated arithmetic mean of all of the height values located along a 10 mm path length that is centered over the midpoint distance between the left and right flex bond channel regions along the line. If, however, the non-channeled region between the left and right flex bond channel regions is too narrow and thus has some level of compression due to the close proximity of the channel regions, a more suitable non-channeled region is chosen as $Zmax_i$, such that $Zmax_i$ most represents the intended height of a non-channeled region of the article within the test sample. Calculate the depth of the flex bond channel region on the left side of test sample i by subtracting $Zmin_{iL}$ from $Zmax_i$, and record as left channel depth, $D_{iL}$, to the nearest 0.1 mm. In like fashion, calculate the depth of the flex bond channel region on the right side of test sample i by subtracting $Zmin_{iR}$ from $Zmax_i$, and record as right channel depth, $D_{iR}$, to the nearest 0.1 mm. Now calculate the arithmetic mean of the $D_{iL}$ and $D_{iR}$ values measured for test sample i, and record as channel depth, Di, to the nearest 0.1 mm. In like fashion, repeat the channel depth measurement for all five replicate test samples, i-v, such that a total of ten flex bond channel regions (5 right and 5 left) are analyzed, and channel depth is recorded for each test sample to the nearest 0.01 mm (i.e. Di-Dv). Now calculate the arithmetic mean across the five channel depths (Di-Dv) calculated for the five replicate test samples, and report as Dry Channel Depth, D, to the nearest 0.01 mm.

Each numerically labeled replicate test sample is retained for the subsequent MD channel bending resistance measurement.

Flex Bond Channel MD Bending Resistance Method:

MD bending resistance of the prepared test specimens is measured on a universal constant rate of extension (CRE) test frame, such as the MTS Alliance using TestSuite Software, as available from MTS Systems Corp., Eden Prairie, MN, or equivalent. The CRE test frame is equipped with a 3 point bend fixture and a load cell for which the forces measured are within 1% to 99% of the limit of the cell (preferably a 10 N load cell). The bottom stationary fixture consists of two cylindrical bars 3.175 mm in diameter by 110 mm in length, made of polished stainless steel each mounted on each end with frictionless roller bearings. These 2 bars are mounted horizontally, aligned front to back and parallel to each other, with top radii of the bars vertically aligned and are free to rotate around the diameter of the cylinder by the frictionless bearings. Furthermore, the fixture allows for the two bars to be move horizontally away from each other on a track so that a gap can be set between them while maintaining their orientation. The top fixture consists of a third cylinder bar also 3.175 mm in diameter by 110 mm in length, made of polished stainless steel mounted on each end with frictionless roller bearings. When in place the bar of the top fixture is parallel to and aligned front to back with the bars of the bottom fixture and is centered between the bars of the bottom fixture. Both fixtures include an integral adapter appropriate to fit the respective position on the universal test frame and lock into position such that the bars are orthogonal to the motion of the crossbeam of the test frame.

Prepare the test specimens for the bending resistance measurement from the numerically labeled test samples previously prepared for the flex bond channel depth measurement as follows. Each individually prepared test specimen is 5.3 mm wide and has a length of at least 35 mm. The width of the test specimen is centered over the width of the flex bond channel region, and the length of the test specimen is parallel to the longitudinal direction of the channel. The test specimen includes the channel region where the 35 mm line was previously drawn within the channel during sample prep. From each of the numerically labeled test samples, two test specimens are prepared; one from the flex bond channel region on the left side of the test sample and one from the flex bond channel region on the right side of the test sample. Each test specimen is obtained from the same region of the flex bond channel region that was previously analyzed for channel depth, denoted by the 35 mm line drawn during sample prep. A total of ten flex bond channel region test specimens are prepared (5 left and 5 right) and numerically labeled (i.e. $i_L$-$v_L$ and $i_R$-$v_R$).

Set the gap ("span") between the bars of the lower fixture to 20 mm±0.5 mm (center of bar to center of bar) with the upper bar centered at the midpoint between the lower bars. Load the first test specimen, $i_L$, such that its long side is perpendicular to and resting on the two lower bars of the fixture, and ensure it is centered under the upper bar with the body-facing surface of the test specimen facing the upper bar. Move the vertical position of the upper bar until the bottom edge of the upper bar is 1 mm above the surface of the test specimen and then zero the crosshead position.

Program the universal test frame for a flexural bend test, to move the crosshead such that the top fixture moves down with respect to the lower fixture at a rate of 1.0 mm/sec for a total distance of 12 mm from the zero position. The crosshead is then immediately returned to the original gage at a rate of 1.0 mm/s. Force (N) and displacement (mm) data are continuously collected at 50 Hz throughout the test. The test specimen width is recorded as 5.3 mm. Start the test and continuously collect time, force and displacement data.

Construct a graph of force (N) versus displacement (mm) for test specimen $i_L$. From the graph, determine the maximum peak force and record as flex bond channel MD peak load, MD peak$_{iL}$, to the nearest 0.01 N. The slope of the initial linear portion of the curve, prior to the peak, is calculated and recorded as flex bond channel MD bending resistance$_{iL}$, to the nearest 0.005 N/mm. Calculate the energy to peak as the area under the force versus displacement curve from the initial point to the peak force and record as flex bond channel MD energy to peak, MD PE$_{iL}$, to the nearest 0.01 N*mm. In like fashion, repeat the entire procedure for test specimen $i_R$, taken from the right channel of test sample i. Now calculate the arithmetic mean for each parameter across the values obtained for the left, $i_L$, and right, $i_R$, test specimens, and record as Dry MD peak$_i$, to the nearest 0.01 N; Dry MD bending resistance$_i$, to the nearest 0.005 N/mm; and Dry MD PE$_i$, to the nearest 0.01 N*mm. In like fashion, the procedure is repeated for all ten flex bond channel region test specimens ($i_L$-$v_L$ and $i_R$-$v_R$) taken from test samples i-v. Calculate the arithmetic mean for each parameter across the values obtained for test samples i-v, and report as Dry MD Peak to the nearest 0.01 N; Dry MD Bending Resistance to the nearest 0.005 N/mm; and Dry MD Energy to Peak, PE, to the nearest 0.01 N*mm.

Flex Bond Channel CD Bending Resistance Method:

CD bending resistance of a fresh set of prepared test specimens is measured on the same universal constant rate of extension (CRE) test frame using the same 3 point bend fixture and load cell as previously described for the MD bending resistance measurement.

A fresh set of test specimens are prepared as follows. Unfold the absorbent article if necessary, then remove the protective covering over the panty fastening adhesive (i.e. wrapper or release paper). Apply a light dusting of talc powder to the adhesive to mitigate tackiness. The test specimen has a width of 25.4 mm (parallel to the longitudinal axis of the article) and a length equal to the distance from the left lateral edge to the right lateral edge of the article (about 70 mm). The test specimen is taken from a region of the article where flex bond channel regions are oriented parallel to the longitudinal axis of the article, and the selected region is otherwise free from residua of folds or wrinkles. Ideally, the test specimen is obtained from the center of the article (intersection of longitudinal and lateral midlines). A total of ten replicate test specimens are prepared. The test specimens will be mounted on the 3 point bend fixture such that five "channeled" replicates will bend along a bond channel (i.e. upper central blade will be parallel to and centered over the channel), and the other five "non-channeled" replicates will bend along a non-channeled region of the test specimen.

Set the gap ("span") between the bars of the lower fixture to 25 mm±0.5 mm (center of bar to center of bar) with the upper bar centered at the midpoint between the lower bars. Mount the first "channeled" test specimen such that it rests on the two lower bars of the fixture with the lateral, outside edges of the test specimen oriented parallel to the bars. Adjust the position the test specimen such that a bond channel is parallel to and centered beneath the upper bar with the body-facing surface of the test specimen facing the upper bar. In this position, the test specimen will be bent along a flex bond channel region. Move the vertical position of the upper bar until the bottom edge of the upper bar is 1 mm above the surface of the test specimen, and then zero the crosshead position. Program the universal test frame for a flexural bend test, to move the crosshead such that the top fixture moves down with respect to the lower fixture at a rate of 1.0 mm/sec for a total distance of 12 mm from the zero position. The crosshead is then immediately returned to the original gage at a rate of 1.0 mm/s. Force (N) and displacement (mm) data are continuously collected at 50 Hz throughout the test. The test specimen width is recorded as 25.4 mm. Start the test and continuously collect time, force and displacement data.

Construct a graph of force (N) versus displacement (mm) for the "channeled" test specimen. The slope of the initial linear portion of the curve is calculated and recorded as dry flex bond channel CD bending resistance, to the nearest 0.005 N/mm. In like fashion, repeat the entire procedure for a total of five "channeled" test specimens. Now calculate the arithmetic mean of the slope values across the five "channeled" test specimens, and report as Dry Flex Bond Channel CD Bending Resistance to the nearest 0.005 N/mm.

The "non-channeled" test specimens are tested in like fashion, with the exception of the positioning of the test specimen. The "non-channeled" test specimen is mounted on the 3 point bend fixture such that it rests on the two lower bars of the fixture with the lateral, outside edges of the test specimen oriented parallel to the bars. Adjust the position the test specimen such that a non-channeled region of the test specimen is centered beneath the upper bar with the body-facing surface of the test specimen facing the upper bar. In this position, the test specimen will be bent along a region what does not contain any portion of a flex bond channel region. Move the vertical position of the upper bar until the bottom edge of the upper bar is 1 mm above the surface of the test specimen, and then zero the crosshead position. The test is then executed as previously described, and time, force and displacement data is continuously collected.

a total of five "non-channeled" test specimens. Now calculate the arithmetic mean of the slope values across the five "non-channeled" test specimens, and report as Dry Non-Channeled CD Bending Resistance to the nearest 0.005 N/mm.

Examples/Data

The following data and examples, including comparative examples, are provided to help illustrate the upper and lower nonwoven layers, absorbent core structures and/or absorbent articles described herein. The exemplified structures are given solely for the purpose of illustration and are not to be construed as limitations of the present disclosure, as many variations thereof are possible without departing from the spirit and scope of the invention.

Nonwoven Material Test

Nonwoven layer materials are tested to assess the ability of the nonwoven material to strain (elongate) with a balanced stretch and to recover to their original state (simulating in-use physical deformation). Samples F-H are comparative examples. The test is performed according to the CD Cyclic Elongation to 3% Strain Method and the Strain to Break Method described herein. The results are shown in Table 1.

TABLE 1

Nonwoven Materials tested in the CD Cyclic Elongation to 3% Strain Method and the Strain to Break Method

| Sample | Nonwoven Material | Fiber Composition | Tensile Stiffness N/mm | Permanent Strain mm/mm | % Strain to Break % |
|---|---|---|---|---|---|
| A | 40 gsm Carded Resilient Nonwoven[1] | BiCo (PE/PET)-60% 2 dTex/ 40% 4 dTex Blend | 0.30 | 0.0060 | >10% |
| B | 55 gsm Resilient Spunlace 1[2] | 30% 10 dTex HS-PET; 20% 1.3 dTex Rayon; 50% 2.2 dTex BiCo (PE/PET) | 1.57 | 0.0064 | >10% |
| C | 50 gsm Resilient Spunlace 6[3] | 20% 1.3 dTex Rayon; 20% 3.3 dTex tri-lobal Rayon; 60% 5.8 dTex PE/PET | 1.50 | 0.0054 | >10% |
| D | 24 gsm Carded Nonwoven[4] | 100% 2 dTex BiCo (PE/PET) | 0.16 | 0.0160 | >10% |
| E | 55 gsm Resilient Spunlace 5[5] | 40% 1.7 dTex/38 mm Rayon; 40% 2.2 dTex PET; 20% 10 dTex HS PET | 0.31 | 0.0127 | >10% |
| F | 18 gsm Spunbond Nonwoven[6] | 100% 2.0 dTex PP | 0.24 | 0.0096 | >10% |
| G | 25 gsm Spunbond Nonwoven[7] | 100% 2.0 Dtex PP | 0.37 | 0.0093 | >10% |
| H | 17 gsm Tissue[8] | 100% Cellulose | 1.72 | 0.0137 | <5% |

[1]Available as ATB Z87G-40 from Xiamen Yanjan New Material Co. (China)
[2]Available as Sawasoft ® 53FC041001 from Sandler GmbH (Germany)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[7]Available as PEGZN25 BICO7030 Phobic from dPFNonwovens Czech S.R.O (Czech Republic)
[8]Available as 3028 from DunnPaper (USA)

Construct a graph of force (N) versus displacement (mm) for the "non-channeled" test specimen. The slope of the initial linear portion of the curve is calculated and recorded as dry non-channeled CD bending resistance, to the nearest 0.005 N/mm. In like fashion, repeat the entire procedure for It is found that suitable nonwoven layer materials strain (elongate) with a balanced stretch vs. recovery behavior. If the nonwoven layer material elongates plastically (i.e., stretches but does not recover) as the fluff/AGM matrix in the inner core layer elongates, there will be insufficient recovery energy to return to the initial, pre-stretched state and the nonwoven layer material will become permanently strained (stretched). The upper nonwoven layers of the present disclosure can have a Permanent Strain value of less than about 0.013. At the same time, if the nonwoven layer material is strained aggressively, for example greater than 5%, the nonwoven layer material needs to retain its integrity and not tear or break (see, for example, Sample H which tears and has a Strain to Break of less than 5%). Nonwoven layers of the present disclosure can have a Strain to Break of greater than about 10%.

The nonwoven layer materials described above are also to assess the ability of nonwoven materials to bend and deform and to recover to their original state. The test is performed according to the Wet and Dry CD Ultra Sensitive 3 Point Bending Method described herein. The results are shown in Table 2.

TABLE 2

| Nonwoven Materials Tested in the Wet and Dry CD Ultra Sensitive 3 Point Bending Method | | | |
| --- | --- | --- | --- |
| Sample | Dry Peak Load N | Dry Bending Energy N*mm | Dry Recovery Energy N*mm |
| A | 0.07 | 0.219 | 0.092 |
| B | 0.38 | 1.015 | 0.291 |
| C | 0.26 | 0.595 | 0.201 |
| D | 0.09 | 0.176 | 0.036 |
| E | 0.03 | 0.059 | 0.032 |
| F | 0.01 | 0.0216 | 0.005 |
| G | 0.03 | 0.0624 | 0.019 |
| H | 0.04 | 0.0734 | 0.031 |

During walking, an absorbent article is compressed and bent side-to-side in a cyclic pattern as the gap between her legs narrows and then expands with her leg motions. Without being limited by theory, it is believed that a nonwoven layer material having a Dry Bending Energy of less than about 2 N*mm will allow this bending compression to occur readily yet will not be so stiff as to hinder the bending compression. At the same time, following the bending compression, the nonwoven layer needs to be able to sustain sufficient dry recovery energy to return the nonwoven layer and the fluff/AGM matrix in the inner core layer back to its initial, pre-bent state. The upper nonwoven layers of the present disclosure can have a Dry Recovery Energy value of greater than about 0.03 N*mm.

Samples A-E exhibit a Dry Peak Load of from 0.03N to 0.38N and a Dry Recovery Energy of from 0.032 to 0.092 N*mm, demonstrating that these materials readily bend and have sufficient dry recovery energy to recover their initial, pre-bent state. Samples F and G, which are comparative examples, exhibit a Dry Peak Load of 0.01N and 0.03N, respectively, and a Dry Recovery Energy of 0.005 N*mm and 0.019 N*mm, respectively, demonstrating that while these materials readily bend, they do not have sufficient recovery energy to recover their initial, pre-bent state after compression. Sample H (comparative example) exhibits a Dry Peak Load of 0.04 N and a Dry Recovery Energy of 0.031 N*mm. However, it is found that Sample H tears when it becomes wet, making it insufficient to function as an upper and/or lower nonwoven layer of the present disclosure.

Without being limited by theory, it is believed that nonwoven layer materials comprising thick fibers (from about 2.0 Dtex to about 10 Dtex) that are arranged within a network structure are able to carry the mechanical load within the fiber network and return the absorbent core structure and/or absorbent article to its initial shape following bending compression. Samples F and G comprise relatively fine fibers (less than about 2.0 Dtex), while Samples A-E comprise fiber blends having a fiber thickness of from about 2.2 Dtex to about 10 Dtex.

Absorbent Core Structure Test

Absorbent cores structures are tested to assess the ability of the absorbent core structure to compress (simulating the compressions experienced between a wearer's legs) and to recover to their original state. Examples 1-3 in Table 3 illustrate absorbent core structures described herein. Comp. Ex. A-C are comparative examples. A description of Ex. 1-3 and Comp. Ex. A-C are listed in Table 3. The absorbent core structures are prepared as described hereafter. The absorbent core structures are evaluated according to the Wet and Dry Bunched Compression Method as described herein. The results are shown in Table 4.

TABLE 3

| Absorbent Core Structures | | | |
| --- | --- | --- | --- |
| Example | Upper Nonwoven Layer | Inner Core Layer | Lower Nonwoven Layer |
| Ex. 1 | 40 gsm Carded Resilient Nonwoven[1] | 175 gsm Fluff[10]/ 70 gsm AGM[9] | 18 gsm Spunbond Nonwoven[6] |
| Ex. 2 | 55 gsm Resilient Spunlace 5[5] | 175 gsm Fluff[10]/ 70 gsm AGM[9] | 18 gsm Spunbond Nonwoven[6] |
| Ex. 3 | 50 gsm Resilient Spunlace 6[3] | 175 gsm Fluff[10]/ 70 gsm AGM[9] | 40 gsm Carded Nonwoven[1] |
| Comp. Ex. A | 24 gsm Carded Nonwoven[4] | 175 gsm Fluff[10]/ 70 gsm AGM[9] | 10 gsm SMS Nonwoven[11] |
| Comp. Ex. B | 17 gsm Tissue[8] | 175 gsm Fluff[10]/ 70 gsm AGM[9] | 17 gsm Tissue[8] |
| Comp. Ex. C | 17 gsm Tissue[8] (10 × 10 bonding) | 175 gsm Fluff[10]/ 70 gsm AGM[9] | 17 gsm Tissue[8] |

[1]Available as ATB Z87G-40 from Xiamen Yanjan New Material Co. (China)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[8]Available as 3028 from DunnPaper (USA)
[9]Available as Favor SXM9745 from Evonik (Germany)
[10]Available as Item 9E3-COOSABSORB S from Resolute Alabama (USA)
[11]Available as Article 4004416 (MR 3585374) from Fitesa (Germany)

The absorbent core structures listed in Table 3 are produced as detailed within the specification. Specifically, the upper nonwoven layer is first introduced onto the forming drum within the laydown section, and under vacuum it is drawn into the 3 dimensional pocket shape. A homogeneous stream of the fluff (cellulose) and AGM material is deposited onto the upper nonwoven layer directly within the forming station. Prior to entering the forming station, the upper nonwoven is coated with a spray adhesive (Technomelt DM 9036U available from Henkel (Germany), 6 gsm continuous meltblown spirals, 50 mm wide) to provide a stronger connection of the fluff (cellulose) and AGM to the upper nonwoven layer without hindering the flow of liquid into the fluff/AGM matrix. On exiting the laydown section, the lower nonwoven web is combined with the nonwoven carrying the homogeneous blend of fluff/AGM. This lower nonwoven is precoated with adhesive (Technomelt DM 9036U available from Henkel (Germany)) to enable a perimeter seal (10 gsm meltblown spirals, 20 mm wide on the sides) and in the center with a 6 gsm, wide continuous meltblown spiral adhesive is applied (Technomelt DM 9036U available from Henkel (Germany)) to better integrate the fluff/AGM matrix.

Figure 4:
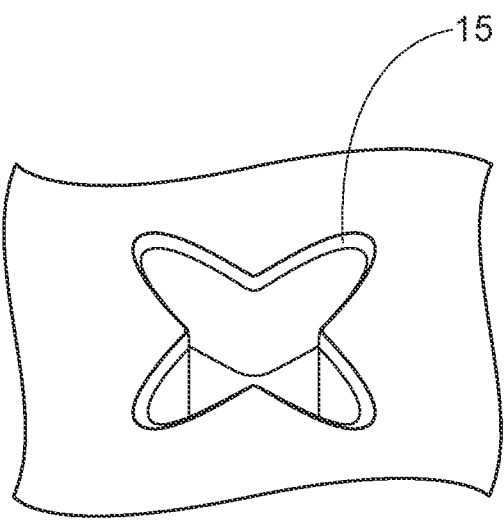
FIG. 4 is a close up illustration of a structural bond site in accordance with the present disclosure.

Ex. 1 through 3 and Comp. Ex. A and B also have the structural bonds shown in FIG. 4 with the profile shown in FIG. 5. Ex. 1-3 and Comp. Ex. A-B have a structural bond spacing of 32 mm×16 mm, thereby occupying a total structural bond site area of 1.38% of the total area of the absorbent core structure. Comp Ex. C is identical to Comp. Ex. B except the structural bond spacing is 10 mm×10 mm, thereby occupying a total structural bond site area of 6.28% of the total area of the absorbent core structure. The structural bonds are applied with a heated aluminum die to create an emboss pattern within a heated hydraulic press. The structural bond embosser plate has protrusions of an area of 3.55 mm$^2$ and about 1 mm in height as shown in FIG. 4 with the profile shown in FIG. 5. The structural bonds are spaced according to the dimensions of separation described above. The structural bond embosser plate is heated to 120° C. and set to a compression pressure of 170 kPa. The absorbent article is placed and oriented underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the structural bond pattern.

Ex. 1-3 and Comp. Ex. A-C also have flex bond channel regions applied with the pattern shown in FIG. 7A. The flex bond channel regions are applied with a heated aluminum die to create an emboss pattern within a heated hydraulic press. The flex bond channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and oriented underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the emboss pattern.

TABLE 4

Absorbent Core Structures Measured in the Wet and Dry Bunched Compression Method

| | Wet and Dry Bunched Compression Method | |
| | 5$^{th}$ Cycle Wet Maximum Compression Force (gf) | 5$^{th}$ Cycle Wet Energy of Recovery (N*mm) |
| Example | | |
| --- | --- | --- |
| Ex. 1 | 208 | 1.30 |
| Ex. 2 | 207 | 1.07 |
| Ex. 3 | 213 | 1.76 |
| Comp. Ex. A | 136 | 0.26 |
| Comp. Ex. B | 129 | 0.59 |
| Comp. Ex. C | 86 | 0.32 |

It is found that absorbent core structures comprising nonwoven layer materials that have sufficient resiliency and recovery energy are able to recover to the original, pre-compression absorbent core structure shape. Ex. 1-3 exhibit a 5$^{th}$ Cycle Wet Energy of Recovery of greater than 1.0 N*mm and a 5$^{th}$ Cycle Wet Maximum Compression Force of from 207 gf to 213 gf. These structures exhibit a low force to compress (less resistance so it feels soft and flexible), yet are still able to recover their shape as the structure is compressed and released in a cyclic fashion. However, Comp. Ex. A-C exhibit a 5$^{th}$ Cycle Wet Energy of Recovery of from 0.26 to 0.59 N*mm. Without sufficient recovery energy after five cycles of compression, Comp. Ex. A-C remain in a compressed, bunched state with insufficient force (stored energy) to recover its original, pre-compression shape.

Absorbent core structures and/or absorbent articles of the present disclosure can have a 5$^{th}$ Cycle Wet Energy of Recovery of greater than about 1.0 N*mm, or from about 1.0 to about 3.5 N*mm Absorbent core structures and/or absorbent articles of the present disclosure can have a 5$^{th}$ Cycle Wet Maximum Compression Force of greater than about 150 gf, preferably greater than about 200 gf, or from about 150 gf to about 225 gf.

It is found that while an individual nonwoven material may have sufficient % Strain to Break in the Strain to Break Method, once combined into an absorbent core structure, the nonwoven material may not be capable of providing sufficient recovery energy for the full absorbent core structure (such as, for example in Comp. Ex. A) to return to its original, pre-compression shape. For instance, in Comp. Ex. A, the basis weight and thickness of the fibers of the upper nonwoven material when combined with the thin lower nonwoven material provides a 5$^{th}$ Cycle Wet Energy of Recovery of less than 1.0 N*mm.

Finished Product Test

Absorbent articles are tested to assess the ability of a wrapped absorbent core structure to compress (simulating the compressions experienced between a wearer's legs) and to recover to their original state. Examples 4-7 illustrate absorbent articles described herein. Comp. Ex. D and E are comparative examples. Comp. Ex. F-L are in-market finished products. A description of Ex. 4-7 and Comp. Ex. D-E are listed in Table 5a. A description of Comp. Ex. F-L is listed in Tables 5b and 5c. Ex. 4-7 and Comp. Ex. D and E are prepared as described hereafter. The absorbent articles in Table 5a and 5b are evaluated according to the Wet and Dry CD and MD 3 Point Bend Method, the Wet and Dry Bunched Compression Method, and the Light Touch Rewet Method as described herein. The results are shown in in Table 6.

TABLE 5a

Absorbent Article Description

| | | Absorbent core structure | | |
| Example | Topsheet | Upper Nonwoven Layer | Inner Core Layer | Lower Nonwoven Layer |
| --- | --- | --- | --- | --- |
| Ex. 4 | Nonwoven SG$^{12}$ | 40 gsm Carded Resilient Nonwoven[1] | 175 gsm Fluff[10]/ 70 gsm AGM[9] | 18 gsm Spunbond Nonwoven[6] |
| Ex. 5 | Nonwoven SG$^{12}$ | 55 gsm Resilient Spunlace 5[5] | 175 gsm Fluff[10]/ 70 gsm AGM[9] | 18 gsm Spunbond Nonwoven[6] |
| Ex. 6 | Nonwoven SG$^{12}$ | 50 gsm Resilient Spunlace 6[3] | 175 gsm Fluff[10]/ 70 gsm AGM[9] | 18 gsm Spunbond Nonwoven[6] |
| Ex. 7 | Nonwoven SG$^{12}$ | 55 gsm Resilient Spunlace 1[2] | 175 gsm Fluff[10]/ 70 gsm AGM[9] | 18 gsm Spunbond Nonwoven[6] |
| Comp. Ex. D | Nonwoven SG$^{12}$ | 24 gsm Carded Nonwoven[4] | 175 gsm Fluff[10]/ 70 gsm AGM[9] | 18 gsm Spunbond Nonwoven[6] |
| Comp. Ex. E | Nonwoven SG$^{12}$ | 17 gsm Tissue[8] | 175 gsm Fluff[10]/ 70 gsm AGM[9] | 17 gsm Tissue[8] |

[1]Available as ATB Z87G-40 from Xiamen Yanjan New Material Co. (China)
[2]Available as Sawasoft ® 53FC041001 from Sandler GmbH (Germany)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[8]Available as 3028 from DunnPaper (USA)
[9]Available as Favor SXM9745 from Evonik (Germany)
[10]Available as Item 9E3-COOSABSORB S from Resolute Alabama (USA)
[12]The nonwoven topsheet "Nonwoven SG" is a nonwoven web according to U.S. Patent Publication No. 2019/0380887.

TABLE 5b

| In-Market Finished Products: | | | |
|---|---|---|---|
| Example | In-Market Product | Size | Where Produced |
| Comp. Ex. F | Always Ultra | Size 2 | Canada |
| Comp. Ex. G | Stayfree Ultra | Size Long | USA |
| Comp. Ex. H | U by K (Kotex Security) | Size Long | USA |
| Comp. Ex. I | Body Form | Size Long | UK |
| Comp. Ex. J | Kao Laurier F | Size Long | Japan |
| Comp. Ex. K | Unicharm Sofy Naked Feel | Size regular | Japan |
| Comp. Ex. L | Always Infinity | Size 2 | Canada |

TABLE 5c

| Materials Found in the In-Market Products (Comp. Ex. F to L) | | | | |
|---|---|---|---|---|
| In-Market Products | Topsheet | First Acquisition Layer | Fluid Storage Layer | Other |
| Comp. Ex. F | Formed Film | 55 gsm Spunlace | 163 gsm Airlaid | n/a |
| Comp. Ex. G | Spunbond Nonwoven | Airlaid Secondary Topsheet | Fluff/ AGM core densified | n/a |
| Comp. Ex. H | Spunbond Nonwoven | Airlaid Secondary Topsheet | Tissue wrapped Fluff/AGM core-densified | Additional cellulose oval element under topsheet |
| Comp. Ex. I | Spunbond Nonwoven | Airlaid Secondary Topsheet | Fluff/AGM core-densified | n/a |
| Comp. Ex. J | Carded Nonwoven | Carded Nonwoven | Tissue wrapped fluff/AGM core | n/a |
| Comp. Ex. K | Carded Nonwoven | Carded Nonwoven | Tissue wrapped fluff/AGM core | n/a |
| Comp. Ex. L | Spunbond Nonwoven | High Internal Phase Foam | High Internal Phase Foam | n/a |

Ex. 4 through 7 and Comp. Ex. D and E include structures as detailed for the Ex. 1 through 3 in Table 3 with the same adhesive designs and same 32 mm×16 mm structural bond pattern (a total structural bond site area of 1.38% of the total area of the absorbent core structure) in the absorbent core structure. Additionally, the absorbent articles include a non-woven topsheet web as detailed in US Patent Publication No. 2019/0380887 bonded to the absorbent core structure with a spray adhesive application (Technomelt DM 9036U available from Henkel (Germany), 3 gsm continuous melt-blown spirals, 50 mm wide, 150 mm long). In addition, a 12 gsm polypropylene backsheet is bonded to the outward-facing surface of the lower nonwoven with a spray adhesive application (Technomelt DM 9036U available from Henkel (German), 3 gsm continuous meltblown spirals, 50 mm wide, 150 mm long).

Ex. 4-7 and Comp. Ex. D and E also have the structural bonds shown in FIG. 4 with the profile shown in FIG. 5. The structural bonds are applied with a heated aluminum die to create an emboss pattern within a heated hydraulic press. The structural bond embosser plate has protrusions of an area of 3.55 mm$^2$ and about 1 mm in height as shown in FIG. 4 with the profile shown in FIG. 5. The structural bonds are spaced according to the dimensions of separation described above. The structural bond embosser plate is heated to 120° C. and set to a compression pressure of 170 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the structural bond pattern.

Prior to bonding the backsheet, flex bond channel regions are applied to Ex. 4-7 and Comp. Ex. D and E with the pattern shown in FIG. 7A. The flex bond channel regions are applied with a heated aluminum die to create an emboss pattern within a heated hydraulic press. The flex bond channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the emboss pattern

TABLE 6

| Absorbent Articles and In-Market Finished Products Tested in the Wet and Dry CD and MD 3 Point Bend Method, the Wet and Dry Bunched Compression Method, and the Light Touch Rewet Method | | | | | |
|---|---|---|---|---|---|
| | Wet & Dry CD & MD 3 Point Bend Method | | | Wet and Dry Bunched Compression Method | | Light Touch |
| Example | Caliper (mm) | CD Dry Modulus (N/mm$^2$) | CD Dry Bending Stiffness (N · mm$^2$) | 5$^{th}$ Cycle Wet Energy of Recovery (N · mm) | 5$^{th}$ Cycle Wet % Recovery % | Rewet Method Light Touch Rewet (g) |
| Ex. 4 | 2.61 | 0.21 | 14.9 | 2.76 | 36 | 0.070 |
| Ex. 5 | 3.35 | 0.09 | 13.5 | 1.68 | 29 | 0.075 |
| Ex. 6 | 3.53 | 0.07 | 13.0 | 1.50 | 31 | 0.047 |
| Ex. 7 | 2.74 | 0.22 | 18.7 | 3.15 | 34 | 0.10 |
| Comp. Ex. D | 3.76 | 0.06 | 13.0 | 1.70 | 27 | 0.17 |
| Comp. Ex. E | 3.44 | 0.08 | 9.1 | 1.29 | 24 | 0.31 |
| Comp. Ex. F | 2.13 | 1.39 | 54.5 | 0.7 | 43 | n/a |
| Comp. Ex. G | 3.05 | 0.41 | 47.5 | 3.1 | 24 | n/a |
| Comp. Ex. H | 2.66 | 0.43 | 30.8 | 2.0 | 28 | n/a |
| Comp. Ex. I | 2.62 | 0.52 | 39.4 | 3.0 | 27 | n/a |
| Comp. Ex. J | 4.84 | 0.10 | 49.4 | 4.8 | 35 | n/a |
| Comp. Ex. K | 3.11 | 0.25 | 30.6 | 1.3 | 26 | n/a |
| Comp. Ex. L | 2.80 | 0.30 | 29 | 2.5 | 73 | n/a |

It is believed that in order to provide high bodily conformability, the absorbent article of the present disclosure can exhibit a low CD Dry Bending Stiffness (i.e., high flexibility) of from about 10 to about 30 N·mm$^2$, or from about 10 to about 25 N·mm$^2$. Also, it is believed that in order to provide an absorbent article that can compress with bodily motion and recover to its original, pre-compressed state against the user's body, the absorbent article of the present disclosure can have a 5$^{th}$ Cycle Wet Energy of Recovery of strongly to the flat shape when it is first applied to the wearer's panty as opposed to the shape against her body.

Structural Bond Test

Absorbent cores structures are tested to assess the impact of structural bond areas on flexibility and bending stiffness. Ex. 8 does not feature any structural bonds within the absorbent core structure. Ex. 9 and Ex. 10 have the structural bonds shown in FIG. 4 with the profile shown in FIG. 5. Ex. 8-10 are prepared as described hereafter. Results of the Wet and Dry MD 3 Point Bend Method are shown in Table 7.

TABLE 7

Absorbent Core Structures according to the invention with different Structural Bond Areas Tested in the Wet and Dry CD and MD 3 Point Bend Method.

| Example | Upper Nonwoven Layer | Inner Core Layer | Lower Nonwoven Layer | Structural Bond Spacing | MD Dry Bending Stiffness (N · mm$^2$) |
|---|---|---|---|---|---|
| Ex. 8 | 50 gsm Resilient Spunlace 6[3] | 175 gsm Fluff[10]/ 70 gsm AGM[9] | 10 gsm SMS Nonwoven[13] | Non-Structural Bonds | 9.8 |
| Ex. 9 | 50 gsm Resilient Spunlace 6[3] | 175 gsm Fluff[10]/ 70 gsm AGM[9] | 10 gsm SMS Nonwoven[13] | 32 mm × 16 mm | 19.2 |
| Ex. 10 | 50 gsm Resilient Spunlace 6[3] | 175 gsm Fluff[10]/ 70 gsm AGM[9] | 10 gsm SMS Nonwoven[13] | 16 mm × 16 mm | 29.6 |

[3]Available as Sawasoft ® 553FC041005 (option 82) from Sandler GmbH (Germany)
[9]Available as Favor SXM9745 from Evonik (Germany)
[10]Available as Item 9E3-COOSABSORB S from Resolute Alabama (USA)
[13]Available as 10 SMS PHILIC from Union Industries SpA. (Italy)

from about 1.0 to about 3.5 N·mm and/or a 5$^{th}$ Cycle Wet % Recovery of from about 29% to about 40%. Absorbent articles of the present disclosure can also maintain good fluid handling that delivers a low light touch rewet of from about 0 to about g.

Ex. 4-7 exhibit a CD Dry Bending Stiffness of from 13.0 to 18.7 N·mm$^2$ and a 5$^{th}$ Cycle Wet % Recovery in the Wet and Dry Bunched Compression Method of from 29 to 36%, demonstrating that these structures will be able to sustain their shape in use. Comp. Ex. D and E exhibit a CD Dry Bending Stiffness of 9.1 and 13.0 N·mm$^2$, respectively. However, Comp. Ex. D and E exhibit a 5$^{th}$ Cycle Wet % Recovery in the Wet and Dry Bunched Compression Method that is less than 29%, demonstrating that these structures will be unable to sustain their shape in use and will remain bunched. Comp. Ex. F-L, which are in-market finished products, exhibit a CD Dry Bending Stiffness of 29 to 47.5 N·mm$^2$, demonstrating that the structures are less flexible and less able to conform.

Figure 5:
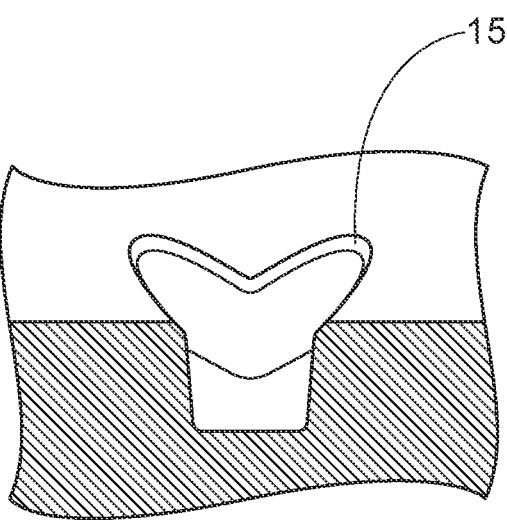
FIG. 5 is a cross section of the structural bond site of FIG. 4.

Without being limited by theory, it is believed that in order to sustain a comfortable shape recovery after compression, sufficient recovery energy is needed to push the absorbent article on the panty back to its pre-compression shape. At the same time, the absorbent article (via the absorbent core structure) needs to recover along the same path as the compression to return to its pre-compression location. If the 5$^{th}$ Cycle Wet Energy of Recovery is less than about 1.0 N·mm the absorbent article may not have the recovery energy needed to recover its shape. If the 5$^{th}$ Cycle Wet Energy of Recovery value is too high, the recovery may be too forceful, leaving the wearer to feel like the absorbent article is not staying in place. If the 5th Cycle Wet % Recovery value is low (less than about 29%), the absorbent article may not return to its pre-compression shape and may remain deformed and bunched. If the 5$^{th}$ Cycle Wet % Recovery value is excessively high (greater than about 40%), it suggests that the absorbent article may recover too Table 7 demonstrates the impact of the total structural bond site area and spacing amount. The asymmetric structural bond shape as shown in FIG. 4 and the profile as shown in FIG. 5 has a maximum area of 3.55 mm$^2$. It is found that the MD Dry Bending Stiffness increases with the structural bond area. Ex. 8, which has non-structural bonds, exhibits an MD Dry Bending Stiffness of 9.8 N·mm$^2$. Ex. 9, which has a structural bond spacing of 32 mm×16 mm (a total structural bond site area of 1.38% of the total area of the absorbent core structure), exhibits an MD Dry Bending Stiffness of 19.2 N·mm$^2$. Ex. 10, which has a structural bond spacing of 16 mm×16 mm (a total structural bond site area of 3.96% of the total area of the absorbent core structure), exhibits an MD Dry Bending Stiffness of 29.6 N·mm$^2$. It is believed that in order to maintain a flexible and conformable absorbent core structure and/or an absorbent article in the front to back (MD) direction of wearing, the absorbent core structure and/or absorbent article can have an MD Dry Bending Stiffness of from about 10 to about 30 N·mm$^2$.

The absorbent core structures listed in Table 7 are produced as detailed within the specification. Specifically, the 50 gsm Resilient Spunlace 6 upper nonwoven is first introduced onto the forming drum within the laydown section, and under vacuum, it is drawn into the 3 dimensional pocket shape. A homogeneous stream of the fluff (cellulose) and AGM material is deposited onto the upper nonwoven material directly within the forming station. Prior to entering the forming station, the upper nonwoven is coated with a spray adhesive (Technomelt DM 9036U available from Henkel (Germany), 6 gsm continuous meltblown spirals, 50 mm wide) to provide a stronger connection of the fluff (cellulose) and AGM to the upper nonwoven layer without hindering the flow of liquid into the fluff/AGM mass. On exiting the laydown section, the 10 gsm SMS lower nonwoven web is combined with the nonwoven carrying the homogeneous blend of fluff (cellulose) and AGM layer. This lower nonwoven is precoated with adhesive (Technomelt DM 9036U available from Henkel (Germany)) to enable a perimeter seal (10 gsm meltblown spirals, 20 mm wide on the sides) and in the center with a 6 gsm, 50 mm wide continuous meltblown spiral adhesive is applied (Technomelt DM 9036U available from Henkel (Germany)) to better integrate the fluff/AGM mass. Structural bonds as shown in FIG. 4 with the profile shown in FIG. 5 are applied to Ex. 9 and 10. The structural bonds of Ex. 9 have a spacing of 32 mm×16 mm, thereby occupying a total structural bond site area of 1.38% of the total area of the absorbent core structure. The structural bonds of Ex. 10 have a spacing of 16 mm×16 mm, thereby occupying a total structural bond site area of 3.96% of the total area of the absorbent core structure with this structural bond profile. The total area of the absorbent core structure is measured according to the Structural Bond Sites Pattern Spacing and Area Measurement Method. The structural bonds are applied with the same method as described above for Ex. 1-3 and Comp. Ex. A-B.

Flex Bond Channel Region Test

Absorbent articles are tested to assess the impact of flex bond channel regions on MD and CD dry bending resistance. In particular, the absorbent articles are tested to assess the ability of the flex bond channel region to bend in the MD, that is longitudinal (or front to back) direction (See Table 9) and to also bend in the CD (side to side) direction (See Table 10). Ex. 11 illustrates an absorbent article described herein. Comp. Ex. M-Q are in-market finished products which have embossed channels. A description of Ex. 11 is listed in Table 8a. A description of Comp. Ex. M-Q is listed in Tables 8b and 8c. Ex. 11 is prepared as described for Ex. 4 in Table 5a above. Ex. 11 and Comp. Ex. M-Q are evaluated according to the Flex Bond Channel Depth Method and Flex Bond Channel MD Bending Resistance Method, with the results shown in Table 9. Ex. 11 was also evaluated according to the Flex Bond Channel CD Bending Resistance Method, with the results shown in Table 10.

TABLE 8a

Absorbent Article Description

| | | Absorbent core structure | | |
|---|---|---|---|---|
| Example | Topsheet | Upper Nonwoven Layer | Inner Core Layer | Lower Nonwoven Layer |
| Ex. 11 | Nonwoven SG[12] | 40 gsm Carded Resilient Nonwoven[1] | 175 gsm Fluff[10]/ 70 gsm AGM[9] | 18 gsm Spunbond Nonwoven[6] |

[1]Available as ATB Z87G-40 from Xiamen Yanjan New Material Co. (China)
[6]Available as PFNZN 18G BICO8020 PHI 6 from dPFNonwovens Czech S.R.O (Czech Republic)
[9]Available as Favor SXM9745 from Evonik (Germany)
[10]Available as Item 9E3-COOSABSORB S from Resolute Alabama (USA)
[12]The nonwoven topsheet "Nonwoven SG" is a nonwoven web according to U.S. Patent Publication No. 2019/0380887.

TABLE 8b

In-Market Finished Products

| Example | In-Market Product | Size | Where Produced |
|---|---|---|---|
| Comp. Ex. M | Stayfree Ultra | Size Long | USA |
| Comp. Ex. N | U by K (Kotex Security) | Size Long | USA |
| Comp. Ex. O | Unicharm Sofy Naked Feel | Size regular | Japan |
| Comp. Ex. P | Walgreens Overnight | Size 4 | USA |
| Comp. Ex. Q | Always Maxi | Size 4 | Mexico |

TABLE 8c

Materials Found in the In-Market Products (Comp. Ex. M to Q)

| In-Market Products | Topsheet | First Acquisition Layer | Fluid Storage Layer |
|---|---|---|---|
| Comp. Ex. M | Spunbond Nonwoven | Airlaid Secondary Topsheet | Fluff/AGM core densified |
| Comp. Ex. N | Spunbond Nonwoven | Airlaid Secondary Topsheet | Tissue wrapped Fluff/AGM core-densified |
| Comp. Ex. O | Carded Nonwoven | Carded Nonwoven | Tissue wrapped fluff/AGM core |
| Comp. Ex. P | Laminated film-Nonwoven Structure | None | Fluff-densified |
| Comp. Ex. Q | Vacuum formed Film | Spunlace | Fluff-densified |

TABLE 9

Absorbent Article and In-Market Finished Products Tested in the Flex Bond Channel Depth Method and the Flex Bond Channel MD Bending Resistance Method

| | Flex Bond Channel Depth Method | | | | Flex Bond Channel MD Bending Resistance Method |
|---|---|---|---|---|---|
| Example | Absorbent Article (AA) Thickness (mm) | Dry Channel Depth (mm) | Channel Depth/AA Thickness (%) | Peak Load (N) | Dry MD Bending Resistance N/mm |
| Ex. 11 | 3.6 | 2.5 | 69% | 0.0969 | 0.0244 |
| Comp. Ex. M | 8.4 | 4.2 | 50% | 0.2323 | 0.0528 |
| Comp. Ex. N | 7.4 | 3.3 | 45% | 0.2074 | 0.0459 |

TABLE 9-continued

Absorbent Article and In-Market Finished Products Tested in the Flex Bond Channel Depth Method and the Flex Bond Channel MD Bending Resistance Method

| | Flex Bond Channel Depth Method | | | | Flex Bond Channel MD Bending Resistance Method |
|---|---|---|---|---|---|
| Example | Absorbent Article (AA) Thickness (mm) | Dry Channel Depth (mm) | Channel Depth/AA Thickness (%) | Peak Load (N) | Dry MD Bending Resistance N/mm |
| Comp. Ex. O | 6.2 | 4.1 | 66% | 0.2277 | 0.0552 |

TABLE 9-continued

Absorbent Article and In-Market Finished Products Tested in the Flex Bond Channel Depth Method and the Flex Bond Channel MD Bending Resistance Method

| Example | Flex Bond Channel Depth Method | | | | Flex Bond Channel MD Bending Resistance |
| | Absorbent Article (AA) Thickness (mm) | Dry Channel Depth (mm) | Channel Depth/AA Thickness (%) | Peak Load (N) | Method Dry MD Bending Resistance N/mm |
| --- | --- | --- | --- | --- | --- |
| Comp. Ex. P | 10.1 | 3.3 | 33% | 0.4167 | 0.0836 |
| Comp. Ex. Q | 9.5 | 3.6 | 38% | 0.518 | 0.1305 |

It is found that Ex. 11 has a well defined flex bond channel region that exhibits a depth to thickness ratio of 69% yet requires less force to bend at only 0.0969 N and a Dry MD Bending Resistance of only 0.0244 N/mm. In contrast, Comp. Ex. M-Q, have a depth to thickness ratio of between 33% to 66% and require a force of 0.2074N to 0.518N to bend. Comp. Ex. M-Q also exhibit a Dry MD Bending Resistance of from 0.0459 to 0.1305, demonstrating that the channel-like structures in these products have a higher resistance to bending (i.e., are less flexible). Without being limited by theory, it is believed that a consumer wearing the absorbent article depicted in Ex. 11 will experience the product conforming to her body with less resistance and pressure on her body, and as a result, will experience a closer more comfortable conforming absorbent article.

TABLE 10

Absorbent Article Tested in the Flex Bond Channel CD Bending Resistance Method

| Example | Flex Bond Channel CD Bending Resistance Method | | |
| | Dry Flex Bond CD Bending Resistance N/mm | Dry Non-Channeled CD Bending Resistance N/mm | CD Bending Resistance Index |
| --- | --- | --- | --- |
| Ex. 11 | 0.010 | 0.017 | 1.7 |

It is found that the Dry Flex Bond CD Bending Resistance in the flex bond channel region is lower than in the non-channeled region adjacent to the flex bond channel region. Ex. 11 exhibits a CD Bending Resistance Index (a ratio of Dry Non-Channeled CD Bending Resistance to Dry Flex Bond CD Bending Resistance) of 1.7. This confirms that the flex bond channel region can readily bend at the channel with lower CD Bending Resistance. Looking at Tables 9 and 10 together, it is found that the Dry CD Bending Resistance and Dry MD Bending Resistance values of Ex. 11 are comparable and significantly lower than Comp. Ex. M-Q. Ex. 11 demonstrates low resistance to bending in both the MD and CD direction, and as such, it is believed that Ex. 11 will be able to closely and comfortably conform to a wide-range of anatomical body shapes.

Combinations/Examples

Paragraph A. A disposable absorbent article comprising: a front end region, a back end region, and a middle region disposed between the front end region and the back end region; a topsheet; a backsheet; an absorbent core structure disposed between the topsheet and the backsheet, wherein the absorbent core structure comprises: (a) an upper nonwoven layer comprising polymer fibers; (b) a lower nonwoven layer comprising polymer fibers; and (c) an inner core layer disposed between the upper nonwoven layer and the lower nonwoven layer, wherein the inner core layer comprises cellulosic fibers and superabsorbent particles; and a flex bond channel region formed in at least the middle region, wherein the flex bond channel region has a dry channel depth of at least 1.0 mm and a channel width of from about 1.0 mm to about 3.0 mm; and wherein the flex bond channel region has a CD Bending Resistance Index of from about 1.1 to about 3.0, and a Dry MD Bending Resistance of less than about 0.04 N/mm, preferably from about 0.005 to about 0.035 N/mm, as measured according to Flex Bond Channel MD Bending Resistance Method.

Paragraph B. The disposable absorbent article according to paragraph A, wherein the flex bond channel region has a minimum channel length of at least about 50 mm.

Paragraph C. The disposable absorbent article according to paragraph A or B, wherein the flex bond channel region comprises one or more flex bond embossments and one or more flex bond land areas disposed between each of the flex bond embossments.

Paragraph D. The disposable absorbent article according to paragraph C, wherein the thickness "T2" of each of the flex bond land areas may be between about 50% to about 70% of an absorbent article thickness "T".

Paragraph E. The disposable absorbent article according to paragraphs C-D, wherein the flex bond embossments have an embossment area and the flex bond channel region has a channel area, wherein the embossment area is from 22% to 65% of the channel area.

Paragraph F. The disposable absorbent article according to any of paragraphs C-E, wherein the flex bond embossments have an embossment length of from about 1.0 mm to about 4.0 mm.

Paragraph G. The disposable absorbent article according to any of paragraphs C-F, wherein each of the flex bond land areas have a length of from about 0.5 mm to about 4 mm.

Paragraph H. The disposable absorbent article according to any of paragraphs A-G, wherein the absorbent article comprises an inner flex bond channel region and an outer flex bond channel region.

Paragraph I. The disposable absorbent article of according to any of paragraphs A-H, wherein the absorbent article has an average density of between about 0.045 g/cm3 and about 0.15 g/cm3.

Paragraph J. The disposable absorbent article according to any of paragraphs A-I, wherein the upper nonwoven has a basis weight of from about 35 gsm to about 85 gsm.

Paragraph K. The disposable absorbent article according to any of paragraphs A-J, wherein the lower nonwoven has a basis weight of from about 10 gsm to about 40 gsm.

Paragraph L. The disposable absorbent article according to any of paragraphs A-K, wherein the inner core layer comprises from about 125 to about 400 gsm cellulosic fibers.

Paragraph M. The disposable absorbent article according to any of paragraphs A-L, wherein the inner core layer comprises from about 50% to about 85% cellulosic fibers, by weight of the inner core layer, and from about 15% to about 50% superabsorbent particles, by weight of the inner core layer.

Paragraph N. The disposable absorbent article according to any of paragraphs A-M, wherein the absorbent article has a CD Dry Bending Stiffness between about 10 N·mm2 to about 30 N·mm2 as measured according to the Wet and Dry CD and MD 3 Point Bend Method, and a 5th Cycle Wet % Recovery of between about 29% and about 40% as measured according to the Wet and Dry Bunched Compression Method.

Paragraph O. The disposable absorbent article according to any of paragraphs A-N, wherein the flex bond channel region has a channel density of from 0.05 g/cm³ to 0.3 g/cm³.

Paragraph P. The disposable absorbent article according to any of paragraphs A-O, wherein the absorbent article further comprises structural bond sites; wherein the structural bond sites have a bond area of from about 2 mm² to about 5 mm².

Paragraph Q. A disposable absorbent article comprising: a topsheet; a backsheet; an absorbent core structure disposed between the topsheet and the backsheet; wherein the topsheet forms a wearer facing surface of the absorbent article and the backsheet forms an outward facing surface of the absorbent article; wherein the absorbent core structure comprises: (a) an upper nonwoven layer comprising polymer fibers; (b) a lower nonwoven layer comprising polymer fibers; and (c) an inner core layer disposed between the upper nonwoven layer and the lower nonwoven layer; wherein the inner core layer comprises cellulosic fibers and superabsorbent particles; wherein the inner core layer comprises from about 125 to about 400 gsm cellulosic fibers; wherein the wearer facing surface of the absorbent article comprises a flex bond channel region having a Dry MD Bending Resistance of less than about 0.04 N/mm as measured according to Flex Bond Channel MD Bending Resistance Method and a channel density of from about 0.05 g/cm³ to about 0.3 g/cm³.

Paragraph R. The disposable absorbent article according to paragraph Q, wherein the flex bond channel region has a channel depth of at least 1 mm.

Paragraph S. The disposable absorbent article according to any of paragraphs Q-R, wherein the flex bond channel region has a channel width of from about 1.0 mm to about 3.0 mm.

Paragraph T. The disposable absorbent article according to any of paragraphs Q-S, wherein the flex bond channel region has a minimum channel length of about 50 mm.

Paragraph U. The disposable absorbent article according to any of paragraphs Q-T, wherein the absorbent article has a thickness, and wherein the flex bond channel region has an average channel depth of about 20% to about 80% the thickness of the absorbent article.

Paragraph V. The disposable absorbent article according to any of paragraphs Q-U, wherein the outward facing surface comprises one or more flex bond depressions.

Paragraph W. A disposable absorbent article comprising: a topsheet; a backsheet; an absorbent core structure disposed between the topsheet and the backsheet, wherein the absorbent core structure comprises an upper nonwoven layer comprising polymer fibers and an inner core layer comprising from about 125 gsm to about 400 gsm cellulosic fibers; wherein the inner core layer has a wearer facing surface and an outward facing surface and the upper nonwoven layer is in direct contact with the wearer facing surface of the inner core layer; and a flex bond channel region comprising one or more flex bond embossments having an embossment length of from about 1.0 mm to about 4.0 mm; wherein the flex bond channel region has a channel depth of at least 1.0 mm and a channel width of from about 1.0 mm to about 3.0 mm; wherein the flex bond channel region has a Dry MD Bending Resistance of less than about 0.04 N/mm as measured according to Flex Bond Channel MD Bending Resistance Method.

Paragraph Y. The disposable absorbent article according paragraph W, wherein the absorbent core structure further comprises a lower nonwoven layer comprising polymer fibers and is in direct contact with the outward facing surface of the inner core layer.

Paragraph X. The disposable absorbent article according to paragraphs W-Y, wherein the area of the one or more flex bond embossments may be between about 22% to about 65% of the flex bond channel region area.

Paragraph Z. The disposable absorbent article according to paragraphs W-X, wherein the one or more flex bond channel regions has a channel density of from about 0.05 g/cm³ to about 0.3 g/cm³.

Paragraph A1. The disposable absorbent article according to paragraphs A-Z, wherein the inner core layer is contained within the nonwoven layers by substantially sealing at least a left side region and a right side region of the upper nonwoven layer and the lower nonwoven.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a front end region, a back end region, and a middle region disposed between the front end region and back end region;
a topsheet;
a backsheet;
an absorbent core structure disposed between the topsheet and the backsheet, wherein the absorbent core structure comprises:
a. an upper nonwoven layer comprising polymer fibers;

b. a lower nonwoven layer comprising polymer fibers; and c. an inner core layer disposed between the upper nonwoven layer and the lower nonwoven layer, wherein the inner core layer comprises cellulosic fibers and superabsorbent particles; and a flex bond channel region formed in at least the middle region, wherein the flex bond channel region has a dry channel depth of at least 1.0 mm and a channel width of from about 1.0 mm to about 3.0 mm; and wherein the flex bond channel region has a CD Bending Resistance Index of from about 1.1 to about 3.0, and a Dry MD Bending Resistance of less than about 0.04 N/mm as measured according to the Flex Bond Channel MD Bending Resistance Method;

wherein the flex bond channel region comprises one or more flex bond embossments and a flex bond land area disposed between each of the one or more flex bond embossments, and wherein each of the flex bond land areas have a length of from about 0.5 mm to about 4 mm.

2. The disposable absorbent article of claim 1, wherein the flex bond channel region has a minimum channel length of at least about 50 mm.

3. The disposable absorbent article of claim 1, wherein the flex bond embossments have an embossment length of from about 1.0 mm to about 4.0 mm.

4. The disposable absorbent article of claim 1, wherein the absorbent article comprises an inner flex bond channel region and an outer flex bond channel region.

5. The disposable absorbent article of claim 1, wherein the absorbent article has an average density of between about 0.045 g/cm³ and about 0.15 g/cm³.

6. The disposable absorbent article of claim 1, wherein the upper nonwoven has a basis weight of from about 35 gsm to about 85 gsm.

7. The disposable absorbent article of claim 1, wherein the lower nonwoven has a basis weight of from about 10 gsm to about 40 gsm.

8. The disposable absorbent article of claim 1, wherein the inner core layer comprises from about 125 to about 400 gsm cellulosic fibers.

9. The disposable absorbent article of claim 1, wherein the inner core layer comprises from about 50% to about 85% cellulosic fibers, by weight of the inner core layer, and from about 15% to about 50% superabsorbent particles, by weight of the inner core layer.

10. The disposable absorbent article of claim 1, wherein the absorbent article has a CD Dry Bending Stiffness between about 10 N·mm2 to about 30 N·mm2 as measured according to the Wet and Dry CD and MD 3 Point Bend Method, and a 5th Cycle Wet % Recovery of between about 29% and about 40% as measured according to the Wet and Dry Bunched Compression Method.

11. A disposable absorbent article comprising:

a topsheet;

a backsheet;

an absorbent core structure disposed between the topsheet and the backsheet; wherein the topsheet forms a wearer facing surface of the absorbent article and the backsheet forms an outward facing surface of the absorbent article;

wherein the absorbent core structure comprises:

a. an upper nonwoven layer comprising polymer fibers;

b. a lower nonwoven layer comprising polymer fibers; and c. an inner core layer disposed between the upper nonwoven layer and the lower nonwoven layer; wherein the inner core layer comprises cellulosic fibers and superabsorbent particles; wherein the inner core layer comprises from about 125 to about 400 gsm cellulosic fibers;

wherein the wearer facing surface of the absorbent article comprises a flex bond channel region having a Dry MD Bending Resistance of less than about 0.04 N/mm as measured according to Flex Bond Channel MD Bending Resistance Method and a channel density of from about 0.05 g/cm³ to about 0.3 g/cm³.

12. The disposable absorbent article of claim 11, wherein the flex bond channel region has a channel depth of at least 1 mm.

13. The disposable absorbent article of claim 12, wherein the flex bond channel region has a channel width of from about 1.0 mm to about 3.0 mm.

14. The disposable absorbent article of claim 13, wherein the flex bond channel region has a minimum channel length of about 50 mm.

15. The disposable absorbent article of claim 11, wherein the absorbent article has a thickness, and wherein the flex bond channel region has an average channel depth of about 20% to about 80% the thickness of the absorbent article.

16. The disposable absorbent article of claim 11, wherein the outward facing surface comprises one or more flex bond depressions.

17. A disposable absorbent article comprising:

a topsheet;

a backsheet;

an absorbent core structure disposed between the topsheet and the backsheet, wherein the absorbent core structure comprises an upper nonwoven layer comprising polymer fibers and an inner core layer comprising from about 125 gsm to about 400 gsm cellulosic fibers; wherein the inner core layer has a wearer facing surface and an outward facing surface and the upper nonwoven layer is in direct contact with the wearer facing surface of the inner core layer; and a flex bond channel region comprising one or more flex bond embossments having an embossment length of from about 1.0 mm to about 3.0 mm; wherein the flex bond channel region has a channel depth of at least 1.0 mm and a channel width of from about 1.0 mm to about 4.0 mm; wherein the flex bond channel region has a Dry MD Bending Resistance of less than about 0.04 N/mm as measured according to Flex Bond Channel MD Bending Resistance Method, wherein the flex bond channel region has a channel density of from about 0.05 g/cm³ to about 0.3 g/cm³.

18. The disposable absorbent article of claim 17, wherein the absorbent core structure further comprises a lower nonwoven layer comprising polymer fibers and is in direct contact with the outward facing surface of the inner core layer.

* * * * *